(12) United States Patent
Hood et al.

(10) Patent No.: US 10,434,065 B2
(45) Date of Patent: Oct. 8, 2019

(54) MICROFLUIDIC LIPOSOME SYNTHESIS, PURIFICATION AND ACTIVE DRUG LOADING

(71) Applicants: Renee Hood, Baltimore, MD (US); Donald Lad DeVoe, Bethesda, MD (US)

(72) Inventors: Renee Hood, Baltimore, MD (US); Donald Lad DeVoe, Bethesda, MD (US)

(73) Assignee: University of Maryland, College Park, College Park, MD (US)

( * ) Notice: Subject to any disclaimer, the term of this patent is extended or adjusted under 35 U.S.C. 154(b) by 50 days.

(21) Appl. No.: 15/456,111

(22) Filed: Mar. 10, 2017

(65) Prior Publication Data

US 2017/0181972 A1 Jun. 29, 2017

Related U.S. Application Data

(62) Division of application No. 14/524,797, filed on Oct. 27, 2014, now Pat. No. 9,592,198.

(60) Provisional application No. 61/896,204, filed on Oct. 28, 2013.

(51) Int. Cl.
| | |
|---|---|
| *A61K 9/127* | (2006.01) |
| *B01J 13/08* | (2006.01) |
| *B01J 19/00* | (2006.01) |
| *A61K 31/704* | (2006.01) |
| *A61K 31/00* | (2006.01) |
| *A61K 31/5415* | (2006.01) |

(Continued)

(52) U.S. Cl.
CPC .......... *A61K 9/1277* (2013.01); *A61K 9/1278* (2013.01); *A61K 31/00* (2013.01); *A61K 31/5415* (2013.01); *A61K 31/704* (2013.01); *A61K 31/7048* (2013.01); *A61K 31/7068* (2013.01); *B01J 13/08* (2013.01); *B01J 19/0093* (2013.01); *B01J 2219/0086* (2013.01); *B01J 2219/00894* (2013.01)

(58) Field of Classification Search
None
See application file for complete search history.

(56) References Cited

U.S. PATENT DOCUMENTS

| | | | | |
|---|---|---|---|---|
| 9,878,325 | B2 * | 1/2018 | Weitz | B01F 5/0646 |
| 2007/0116753 | A1 * | 5/2007 | Hong | A61K 9/0019 |
| | | | | 424/450 |
| 2010/0316696 | A1 * | 12/2010 | Wiggenhorn | A61K 9/1277 |
| | | | | 424/450 |

OTHER PUBLICATIONS

Abraham S et al. (2005) "The liposomal formulation of doxorubicin," Methods Enzymol. 391:71-97.

(Continued)

*Primary Examiner* — Jeffrey D Washville
(74) *Attorney, Agent, or Firm* — William C. Schrot; AuerbachSchrot LLC

(57) ABSTRACT

Microfluidic methods and systems are provided for continuous flow synthesis and active loading of liposomes, which include a liposome formation region configured to form a population of liposomes and a microdialysis region downstream from the liposome formation region and configured to form a transmembrane gradient for active drug loading of the liposomes. Microfluidic methods and systems for high throughput production of liposomes are also provided featuring high aspect ratio microchannels.

20 Claims, 21 Drawing Sheets
(1 of 21 Drawing Sheet(s) Filed in Color)

(51) Int. Cl.
A61K 31/7048 (2006.01)
A61K 31/7068 (2006.01)

(56) References Cited

OTHER PUBLICATIONS

Ahsan, E. et al. (2002) "Targeting to macrophages: role of physicochemical properties of particulate carriers—liposomes and microspheres—on the phagocytosis by macrophages," J. Controlled Release 79:29-40.
Allen, T. M. et al. (2002) "Use of the post-insertion method for the formation of ligand-coupled liposomes," Cell. & Mol. Biol. Letters 7:217-219.
Allen, T.M. & Cullis, P.R. (2013) "Liposomal drug delivery systems: From concept to clinical applications," Adv. Drug Delivery Rev. 65:36-48.
Allen, T.M. & Martin, F.J. (2004) "Advantages of liposomal delivery systems for anthracyclines," Semin. Oncol. 31:5-15.
Andar, A.U. et al. (2014) "Microfluidic Preparation of Liposomes to Determine Particle Size Influence on Cellular Uptake Mechanisms" Pharm. Res. 31:401-13.
Andresen, T.L. et al. (2005) "Advanced strategies in liposomal cancer therapy: Problems and prospects of active and tumor specific drug release," Prog. Lipid Res. 44:68-97.
Barenholz, Y. (2001) "Liposome application: problems and prospects," Current Opinion in Colloid Interface Sci., 6:66-77.
Barenholz, Y. C. (2012) "Doxil®—The First FDA Approved Nano-Drug: Lessons Learned," J. Controlled Release 160:117-134.
Becker, H. & Heim, U. (2000) "Hot embossing as a method for the fabrication of polymer high aspect ratio structures," Sensors Actuators A Phys. 83:130-135.
Berger, N. et al. (2001) "Filter extrusion of liposomes using different devices: comparison of liposome size, encapsulation efficiency, and process characteristics," International Journal of Pharmaceutics 223:55-68.
Brannon-Peppas, L. & Blanchette, J.O. (2012) "Nanoparticle and targeted systems for cancer therapy," Adv. Drug Deliv. Rev. 64:206-212.
Brodeur, G. M. et al. (2003) "Neuroblastoma: biological insights into a clinical enigma," Nature Review Cancer 3:203-216.
Chakrabarti, I. et al. (2012) "Reversible adaptive plasticity: a mechanism for neuroblastoma cell heterogeneity and chemoresistance," Frontiers in Oncology 2:1-14.
Chana, H. I. & Yeh M.K. (2012) "Clinical development of liposome-based drugs: formulation, characterization, and therapeutic efficacy," International J. of Nanomedicine 7:49-60.
Chen, C. et al. (2010) "An overview of liposome lyophilization and its future potential," J. Controlled Release 142:299-311.
Chen, D. et al. (2012) "Rapid discovery of potent siRNA-containing lipid nanoparticles enables by controlled microfluidic formulation," J. Am. Chem. Soc. 134(16)6948-51.
Chen, H. et al. (2010) "Construction of supported lipid membrane modified piezoelectric biosensor for sensitive assay of cholera toxin based on surface-agglutination of ganglioside-bearing liposomes," Anal. Chim. Acta, 657(2):204-209.
Chithrani, B. D. et al. (2006) "Determining the Size and Shape Dependence of Gold Nanoparticle Uptake into Mammalian Cells," Nano Letters 6:662-668.
Cho, E. C. et al. (2011) "The effect of sedimentation and diffusion on cellular uptake of gold nanoparticles," Nature Nanotechnology 6:385-391.
Cho, K. et al. (2008) "Therapeutic nanoparticles for drug delivery in cancer," Clin. Cancer Research 14:1310-1316.
Clerc, S. & Barenholz, Y. (1995) "Loading of amphipathic weak acids into liposomes in response to transmembrane calcium acetate gradients," Biochim. Biophys. Acta, Biomembr., 1240:257-265.
Clerc, S. & Barenholz, Y. (1998) "A quantitative model for using acridine orange as a transmembrane pH gradient probe," Anal. Biochem., 259:104-111.
Cool, S.K. et al. (2013) "Coupling of drug containing liposomes to microbubbles improves ultrasound/ triggered drug delivery in mice," J. Controlled Release 172:885-893.
Cuia, J. et al. (2007) "Direct comparison of two pegylated liposomal doxorubicin formulations: is AUC predictive for toxicity and efficacy?" J. Controlled Release 118:204-215.
Cullis, P.R. et al. (1989) "Generation and Loading of Liposomal Systems for Drug Delivery Applications," Adv. Drug Delivery Rev. 3:267-282.
De Bernardi, B. et al. (2003) "Disseminated neuroblastoma in children older than one year at diagnosis: comparable results with three consecutive high-dose protocols adopted by the Italian Co-Operative Group for Neuroblastoma," J. Clinical Oncology 21:1592-1601.
Deamer, D. W. et al. (1972) "The response of fluorescent amines to pH gradients across liposome membranes," Biochim. Biophys. Acta, 274(2):323-335.
Drummond, D.C. et al. (1999) "Optimizing liposomes for delivery of chemotherapeutic agents to solid tumors," Pharmacol. Rev., 51:691-743.
Du, Y. et al. (2010) "A simplified design of the staggered herringbone micromixer for practical applications," Biomicrofluidics 4:1-13.
Duncan, R. & Richardson, S. C. W. (2012) "Endocytosis and Intracellular Trafficking as Gateways for Nanomedicine Delivery: Opportunities and Challenges," Mol. Pharmaceutics 9:2380-2402.
Ebrahim, S et al. (2005) "Applications of liposomes in ophthalmology," Surv. Ophthalmol 50:167-82.
Epstein-Barash, H. et al. (2010) "Physicochemical parameters affecting liposomal bisphosphonates bioactivity for restenosis therapy: internalization, cell inhibition, activation of cytokines and complement, and mechanism or cell death," J. Controlled Release 146:182-195.
Fenske, D. B. et al. (2008) "Liposomal nanomedicines: an emerging field," Toxicologic Pathology 36:21-29.
Fritze, A. et al. (2006) "Remote loading of doxorubicin into liposomes driven by a transmembrane phosphate gradient," Biochimica et biophysica acta 1758(10):1633-40.
Gabizon, A. & Martin, F. (1997) "Polyethylene glycol-coated (pegylated) liposomal doxorubicin. Rationale for use in solid tumors." Drugs 54:15-21.
Garin-Chesa, P. et al. (1993) "Trophoblast and ovarian cancer antigen LK26, Sensitivity and specificity in immunopathology and molecular identification as a folate-binding protein," Am. J. Pathol. 142:557-567.
Glück, R. (1995) "Liposomal presentation of antigens for human vaccines," Pharm. Biotechnol. 6:325-45.
Grabielle-Madelmont, C. (2003) "Characterization of loaded liposomes by size exclusion chromatography," J. Biochemical and Biophysical Methods 56:189-217.
Gu, F. X. et al. (2007) "Targeted nanoparticles for cancer therapy," Nano Today 2:14-21.
Gurney. J. G. et al. (1992) "Infant cancer in the U.S.: histology-specific incidence and trends, 1973 to 1992," J. American Society of Pediatric Hematology Oncology 19:428-432.
Haran, G. et al. (1993) "Transmembrane ammonium sulfate gradients in liposomes produce efficient and stable entrapment of amphipathic weak bases," Biochemica et biophysica acta 1151(2):201-15.
Harrigan, P.R. et al. (1993) "Accumulation of doxorubicin and other lipophilic amines into large unilamellar vesicles in response to transmembrane pH gradients," Biochim. Biophys. Acta, 1149(2):329-338.
Hertzog, D.E. et al. (2004) "Femtomole mixer for microsecond kinetic studies of protein folding," Anal. Chem. 76:7169-78.
Hillaireau, H. & Couvreur, P. (2009) "Nanocarriers' entry into the cell: relevance to drug delivery," Cellular and molecular life sciences: CMLS 66:2873-2896.
Hitchcock, K.E. (2010) "Ultrasound-enhanced delivery of targeted echogenic liposomes in a novel ex vivo mouse aorta model," J. Controlled Release, 144:288-295.
Holzer, M. et al. (2009) "Preparative size exclusion chromatography combined with detergent removal as a versatile tool to prepare

(56) References Cited

OTHER PUBLICATIONS unilamellar and spherical liposomes of highly uniform size distribution," J. Chromatography A 1216:5838-5848.

Hong, K. et al. (1985) "Interaction of clathrin with liposomes: pH-dependent fusion or phospholipid membranes induced by clathrin," FEBS letters 191:17-23.

Hood, R.R. et al. (2013) "Microfluidic Synthesis of PEG- and Folate-Conjugated Liposomes for One-step Formation of Targeted Stealth Nanocarriers," Pharm. Res. 30:1597-607.

Hood, R.R. et al. (2014) "A facile route to the synthesis of monodisperse nanoscale liposomes using 3D microfluidic hydrodynamic focusing in a concentric capillary array," Lab Chip 14:2403-2409.

Hood, R.R. et al. (2014) "Microfluidic remote loading for rapid single-step liposomal drug preparation," Lab Chip 14:3359-67.

Hood, R.R. et al. (2014) "Microfluidic-Enabled Liposomes Elucidate Size-Dependent Transdermal Transport," PLoS One 9:e92978.

Hortobágyi, G.N. (1997) "Anthracyclines in the treatment of cancer. An overview." Drugs, 54:1-7.

Huang, J. et al. (2010) "Effects of nanoparticle size on cellular uptake and liver MRI with polyvinylpyrrolidone-coated iron oxide nanoparticles," ACS nano 4:7151-7160.

Hung, P. J. et al. (2005) "A novel high aspect ratio microfluidic design to provide a stable and uniform microenvironment for cell growth in a high throughput mammalian cell culture array," Lab Chip, 5:44-8.

Immordino, M.L. et al. (2006) "Stealth liposomes: review of the basic science, rationale, and clinical applications, existing and potential," International J. Nanomedicine, 1(3):297-315.

Ishida, T. et al. (1999) "A combinatorial approach to producing sterically stabilized (Stealth) immunoliposomal drugs," FEBS letters 460:129-133.

Ishida, T. et al. (2002) "Liposome Clearance," Bioscience Reports 22:197-224.

Ismagilov, R.F. et al. (2000) "Experimental and theoretical scaling laws for transverse diffusive broadening in two-phase laminar flows in microchannels," Appl. Phys. Lett., 2000, 76:2376-2378.

Ito, H. (2005) "Chemical amplification resists for microlithography," Adv Polym Sci 172:37-245.

Iversen, T. et al. (2011) "Endocytosis and intracellular transport of nanoparticles; Present knowledge and need for future studies," Nano Today 6:176-185.

Jahn, A. et al. (2004) "Controlled Vesicle Self-Assembly in Microfluidic Channels with Hydrodynamic Focusing," J. Am.Chem. Soc. 126:2674-2675.

Jahn, A. et al. (2007) "Microfluidic Directed Formation of Liposomes of Controlled Size," Langmuir 23:6289-6293.

Jahn, A. et al. (2008) "Preparation of nanoparticles by continuous-flow microfluidics," J. Nanoparticle Res. 10:925-934.

Jahn, A. et al. (2010) "Microfluidic mixing and the formation of nanoscale lipid vesicles," ACS nano 4:2077-2087.

Jesorka, A. & Orwar, O. (2008) "Liposomes: technologies and analytical applications" Annu. Rev. Anal. Chem. (Palo Alto. Calif.) 1:801-32.

Jin, H. et al. (2009) "Size-dependent cellular uptake and expulsion of single-walled carbon nanotubes: single particle tracking and a generic uptake model for nanoparticles," ACS nano 3:149-158.

Jiskoot, W. et al. (1986) "Preparation of liposomes via detergent removal from mixed micelles by dilution. The effect of bilayer composition and process parameters on liposome characteristics," Pharmaceutisch Weekblad Scientific Edition 8:259-265.

Kamps, J. & Scherphof, G. (1998) "Receptor versus non-receptor mediated clearance of liposomes," Advanced drug delivery reviews 32:81-97.

Kano, K. & Fendler, J. H. (1978) "Pyranine as a sensitive pH probe for liposome interiors and surfaces. pH gradients across phospholipid vesicles" Biochim. Biophys. Acta, 509(2):289-299.

Kelly, C. et al. (2011) "Targeted Liposomal Drug De livery to Monocytes and Macrophages," J. Drug Delivery 2011,727241.

Kikuchi, H. et al. (1999) "Gene delivery using liposome technology," J. Conto. Rel. 62:269-277.

Kim, Y. et al. (2012) "Mass production and size control of lipid-polymer hybrid nanoparticles through controlled microvortices," Nano Lett. 12(7):3587-91.

Krishna, R. & Mayer, L.D. (1997) "Liposomal doxorubicin circumvents PSC 833-free drug interactions, resulting in effective therapy of multidrug resistant solid tumors," Cancer Res. 57:5246-53.

Kumar, S. et al. (2012) "Size Dependent Interaction of Silica Nanoparticles with Different Surfactants in Aqueous Solution," Langmuir 28(25):9288-9297.

Kuribayashi, K. et al. (2006) "Elecfroformation of giant liposomes in microfluidic channels," Measurement Science and Technology 17:3121.

Lasic, D.D. (1998) "Novel applications of liposomes," Trends in Biotechnology 16:307-321.

Lasic, D.D. et al. (1995) "Transmembrane gradient driven phase transitions within vesicles: lessons for drug delivery," Biochim. Biophys. Acta, 1239:145-156.

Leaist, D.G & Hao, L. (1992) "Diffusion with molecular association in chloroform + friethylamine and chloroform + dioxane mixtures," J. Solution Chem. 21:345-350.

Lee. R. J. & Low, P. S. (1994) "Delivery of liposomes into cultured KB cells via folate receptormediated endocytosis," J. Biol. Chem. 269:3198-3204.

Lewrick, F. & Suss, R. (2010) "Remote loading of anthracyclines into liposomes," Methods Mol. Biol., 605:139-145.

Li, X. et al. (1998) "Doxorubicin physical state in solution and inside liposomes loaded via a pH gradient," Biochim. Biophys. Acta, Biomembr., 1415:23-40.

Lim, J.-M. et al. (2014) "Parallel microfluidic synthesis of size-tunable polymeric nanoparticles using 3D flow focusing towards in vivo study," Nanomedicine 10:401-9.

Lim, J.-M. et al. (2014) "Ultra-High Throughput Synthesis of Nanoparticles with Homogeneous Size Distribution Using a Coaxial Turbulent Jet Mixer," ACS Nano 8:6056-65.

Litzinger, D. C. et al. (1994) "Effect of liposome size on the circulation time and intraorgan distribution of amphipathic poly-(ethylene glycol)-containing liposomes," Biochim. Biophys. Acta 1190:99-107.

Liu, Y. et al. (2007) "Nanomedicine for drug delivery and imaging: a promising avenue for cancer therapy and diagnosis using targeted functional nanoparticles," International J. Cancer 120:2527-2537.

Madden, T.D. et al. (1990) "Incorporation of amphotericin B into large unilamellar vesicles composed of phosphatidylcholine and phosphatidylglycerol," Chem. Phys. Lipids, 52:189-198.

Maeda, H. (2010) "Tumor-selective delivery of macromolecular drugs via the EPR effect: background and future prospects," Bioconjugate Chemistry 21:797-802.

Maeda, H. (2012) "Macromolecular therapeutics in cancer treatment: the EPR effect and beyond," J. Controlled Release 164:138-144.

Maguire, L. A. et al. (2003) "Preparation of small unilamellar vesicles (SUV) and biophysical characterization of their complexes with poly-1 -lysine-condensed plasmid DNA," Biotechnology and Applied Biochemistry 37:73-81.

Maris, J.M. (2010) "Recent Advances in Neuroblastoma," N Engl J Med. 362: 2202-2211.

Matsumura, Y. & Maeda. H. (1986) "A new concept for macromolecular therapeutics in cancer chemotherapy: mechanism of tumoritropic accumulation of proteins and the antitumor agent SMANCS," Cancer Res 6:193-210.

Matthay, K. K. et al. (1999) "Treatment of high-risk neuroblastoma with intensive chemotherapy. radiotherapy. autologous bone marrow transplantation, and 13-cis-retinoic acid," Children's Cancer Group. N Engl J. Medicine 341:1165-1173.

Mayer, L.D. et al. (1986) "Uptake of Adriamycin into large unilamellar vesicles in response to a pH gradient," Biochim. Biophys. Acta, Biomembr., 857:123-126.

Mayer, L.D. et al. (1989) "Influence of Vesicle Size, Lipid Composition, and Drug-to-Lipid Ratio on the Biological Activity of Liposomal Doxorubicin in Mice" Cancer Res. 49:5922-5930.

(56) References Cited

OTHER PUBLICATIONS

Mayer, L.D. et al. (1990) "Characterization of liposomal systems containing doxorubicin entrapped in response to pH gradient," Biochim. Biophys. Acta 1025:143-151.

McMillan, J. et al. (2011) "Cell delivery of therapeutic nanoparticles," Progress in molecular biology and translational science 104:563-601.

Meure, I.A. et al. (2008) "Conventional and Dense Gas Techniques for the Production of Liposomes: A Review," AAPS Pharmscitech 9:798-809.

Minotti, G. et al. (2004) "Anthracyclines: molecular advances and pharmacologic developments in antitumor activity and cardiotoxicity." Pharmacol. Rev., 56(2):185-229.

Moghimi, S.M. & Szebeni, J. (2003) "Stealth liposomes and long circulating nanoparticles: critical issues in pharmacokinetics, opsonization and protein-binding properties," Prog. Lipid Res. 42:463-478.

Moses, M. A., Brem. H. & Langer. R. (2003) "Advancing the field of drug delivery: taking aim at cancer," Cancer Cell 4:337-341.

Nagayasu, A. et al. (1999) "The size of liposomes: a factor which affects their targeting efficiency to tumors and therapeutic activity or liposomal antitumor drugs," Advanced Drug Delivery Reviews 40:75-87.

Nichols, J.W. & Deamer, D.W. (1976) "Catecholamine uptake and concentration by liposomes maintaining pH gradients," Biochim. Biophys. Acta, 455:269-271.

Nii, T. & Ishii, F. (2005) "Encapsulation efficiency of water-soluble and insoluble drugs in liposomes prepared by the microencapsulation vesicle method," International J. Pharmaceutics 298:198-205.

O'Shaughnessy, J. (2003) "Liposomal Anthracyclines for Breast Cancer: Overview," Oncologist 8:1-2.

Otake. K. et al. (2006) "Preparation of liposomes using an improved supercritical reverse phase evaporation method," Langmuir The ACS Journal of Surfaces and Colloids 22:2543-2550.

Park, J. W. et al. (2002) "Future directions of liposome- and immunoliposome-based cancer therapeutics," Semin. Oncol. 31:196-205.

Patri, A.K. et al. (2002) "Dendritic polymer macromolecular carriers for drug delivery," Current Opinion in Chemical Biology 6:466-471.

Pollock, S. et al. (2010) "Uptake and trafficking of liposomes to the endoplasmic reticulum," The FASEB 24:1866-1878.

Ramachandran, S. et al. (2006) "Cisplatin Nanoliposomes for Cancer Therapy: AFM and Fluorescence imaging of Cisplatin Encapsulation, Stability, Cellular Uptake and Toxicity," Langmuir 22:8156-8162.

Sabnis, N. et al. (2012) "Enhanced solubility and functionality of valrubicin (AD-32) against cancer cells upon encapsulation into biocompatible nanoparticles," International J. Nanomedicine 7:975-83.

Schreier, H. et al. (1993) "Pulmonary delivery of liposomes," J. Control. Release 24:209-223.

Shan, Y. et al. (2009) "Size-dependent endocytosis of single gold nanoparticles," Chemical Communications 47:8091-8093.

Stephan, K. et al. (2007) "Fast prototyping using a dry film photoresist: microfabrication of soft-lithogrpahy masters for microfluidic structures," J. Micromech. Microeng., 17:N69-N74.

Straubinger, R. M. et al. (1983) "Endocytosis of liposomes and intracellular fate of encapsulated molecules: Encounter with a low pH compartment after internalization in coated vesicles," Cell 32:1069-1079.

Szoka, F. & Papahadjopoulos, D. (1978) "Procedure for preparation of liposomes with large internal aqueous space and high capture by reverse phase evaporation," Proceedings of the National Academy of Sciences of the United States of America 75:4194-4198.

Tajiri, T. et al. (2001) "Clinical and biologic characteristics for recurring neuroblastoma at mass screening cases in Japan," Cancer 92:349-353.

Takano, S. et al. (2003) "Physicochemical properties of liposomes affecting apoptosis induced by cationic liposomes in macrophages," Pharmaceutical Research 20:962-968.

Tazina, E.V. et al. (2011) "Qualitative and quantitative analysis of thermosensitive liposomes loaded with doxorubicin," Pharm. Chem. J. 46:54-59.

Tazina, E.V. et al. (2011) "Specific features of drug encapsulation in liposomes (A review)," Pharm. Chem. J. 45(8):481-490.

Templeton et al. (1997) "Improved DNA: Liposome complexes for increased systemic delivery and gene expression," Nat. Biotechnol. 15:647-652.

Toffoli. G. et al. (1997) "Overexpression of folate binding protein in ovarian cancers," International J. Cancer 74:193-198.

Uhumwangho, M.U. & Okor, R.S. (2005) "Current trends in the production and biomedical applications of liposomes: a review," Sciences New York 4:9-21.

Venditto, V.J. & Szoka, F.C. (2013) "Cancer nanomedicines: so many papers and so few drugs!" Adv. Drug Deliv. Rev. 65:80-8.

Wagner, A. et al. (2002) "The crossflow injection technique: An improvement of the ethanol injection method," J. Liposome Res 12:259-270.

Wagner, V. et al. (2006) "The emerging nanomedicine landscape," Nat. Biotechnol. 24:1211-7.

Wang, A.Z. et al. (2012) "Nanoparticle Delivery of Cancer Drugs," Annu. Rev. Med. 63:185-98.

Woods, W. G. et al. (2002) "Screening of infants and mortality due to neuroblastoma," N Engl. J. Med 346:1041-1046.

Xia, Y. & Whitesides, G.M. (1998) "Soft Lithography," Annu. Rev. Mater. Sci. 28:153-184.

Yalcin, B. et al. (2010) "High-dose chemotherapy and autologous haematopoietic stem cell rescue for children with high-risk neuroblastoma," Cochrane database of systematic reviews Online 5.CD006301.

Yoshida, T. et al. (2006) "Induction of cancer cell-specific apoptosis by folate-labeled cationic liposomes," J. Controlled Release 111:325-332.

Zamboni, W.C. (2005) "Liposomal, Nanoparticle, and Conjugated Formulations of Anticancer Agents," Clin. Cancer Res. 11:8230-8234.

Zhang, S. et al. (2009) "Size-Dependent Endocytosis of Nanoparticles," Advanced materials Deerfield Beach Fla 21:419-424.

Zook, J.M. & Vreeland, W.N. (2010) "Effects of temperatures, acyl chain length, and flow-rate ratio on lipsome formation and size in a microfluidic hydrodynamic focusing device," Soft Matter, 6:1352-1360.

Zucker, D. et al. (2009) "Liposome drugs loading efficiency: a working model based on loading conditions and drug's physiochemical properties," J. Controlled Release, 139:73-80.

\* cited by examiner

MICROFLUIDIC LIPOSOME SYNTHESIS, PURIFICATION AND ACTIVE DRUG LOADING

CROSS-REFERENCE TO RELATED APPLICATIONS

This application is a divisional of U.S. patent application Ser. No. 14/524,797, filed Oct. 27, 2014, which application is based on U.S. Provisional Patent Application Ser. No. 61/896,204, filed Oct. 28, 2013, which applications are incorporated herein by reference in their entireties and to which priority is claimed.

STATEMENT REGARDING FEDERALLY SPONSORED RESEARCH OR DEVELOPMENT

This work was supported by the National Science Foundation (NSF) under CBET0966407 grant. The US government has certain rights in this invention.

FIELD OF THE INVENTION

The present invention relates to microfluidic methods and systems for continuous flow synthesis of nanoparticles, and in particular microfluidic systems for preparing drug-loaded liposomes as well as microfluidic systems for high throughput production of liposomes.

BACKGROUND OF THE INVENTION

Liposomes are lipid bilayer vesicle nanoparticles which have attracted great interest as drug delivery vehicles (Kikuchi, H. et al. (1999) "*Gene delivery using liposome technology,*" J. Conto. Rel. 62:269-277; Templeton et al. (1997) "*Improved DNA: Liposome complexes for increased systemic delivery and gene expression,*" Nat. Biotechnol. 15:647-652; Abraham. S. et al. (2005) "*The liposomal formulation of doxorubicin,*" Methods Enzymol. 391:71-97; Andresen, T. L. et al. (2005) "*Advanced strategies in liposomal cancer therapy: Problems and prospects of active and tumor specific drug release,*" Prog. Lipid Res. 44:68-97; Ramachandran, S. et al. (2006) "*Nanoliposomes for Cancer Therapy: AFM and Fluorescence imaging of Cisplatin Encapsulation, Stability, Cellular Uptake and Toxicity,*" Langmuir 22:8156-8162; Zamboni, W. C. (2005) "*Liposomal Nanoparticle, and Conjugated Formulations of Anticancer Agents,*" Clin. Cancer Res. 11:8230-8234). Encompassing the ability to encapsulate aqueous solutions within their core, isolate lipophilic compounds within their lipid bilayer, and support tailored surface chemistries for targeted delivery, liposomes are versatile, multifunctional nanoparticles with numerous applications including drug delivery for cancer treatment, antibiotics, and anesthetic compounds (Allen, T. M. & Cullis, P. R. (2013) "*Liposomal drug delivery systems: From concept to clinical applications,*" Adv. Drug Delivery Rev. 65:36-48; Fenske, D. B. et al. (2008) "*Liposomal nanomedicines: an emerging field,*" Toxicologic Pathology 36:21-29).

Due to their ability to increase the drug loading capacity by an order of magnitude or more compared to other delivery methods (Gu, F. X. et al. (2007) "*Targeted nanoparticles for cancer therapy,*" Nano Today 2:14-21) and protect their payloads from metabolic activity and early excretion, liposomal drugs provide increased therapeutic indices while minimalizing the damaging side effects of their non-encapsulated counterparts (Immordino, M. L. et al. (2006) "*Stealth liposomes: review of the basic science, rationale, and clinical applications, existing and potential,*" International J. Nanomedicine, 1(3):297-315). As such, liposome encapsulated drugs have had an immense impact in oncology, with long circulating liposomes providing preferential extravasation from tumor vessels (Park, J. W. et al. (2002) "*Future directions of liposome- and immunoliposome-based cancer therapeutics,*" Semin. Oncol. 31:196-205).

Liposome-encapsulated drugs have exhibited potent activity against a wide range of cancers including breast, ovarian, uterine, and other solid tumors (Gu, F. X. et al. (2007) "*Targeted nanoparticles for cancer therapy,*" Nano Today 2:14-21; Patri, A. K. et al. (2002) "*Dendritic polymer macromolecular carriers for drug delivery,*" Current Opinion in Chemical Biology 6:466-471; Wang, A. Z. et al. (2012) "*Nanoparticle Delivery of Cancer Drugs,*" Annu. Rev. Med. 63:185-98; Brannon-Peppas, L. & Blanchette, J. O. (2012) "*Nanoparticle and targeted systems for cancer therapy,*" Adv. Drug Deliv. Rev. 64:206-212; Gabizon, A. & Martin, F. (1997) "*Polyethylene glycol-coated (pegylated) liposomal doxorubicin. Rationale for use in solid tumors.*" Drugs 54:15-21; Krishna, R. & Mayer, L. D. (1997) "*Liposomal doxorubicin circumvents PSC 833-free drug interactions, resulting in effective therapy of multidrug resistant solid tumors,*" Cancer Res. 57:5246-53). Liposome delivery systems have also had an impact in vaccinology (Glück, R. (1995) "*Liposomal presentation of antigens for human vaccines,*" Pharm. Biotechnol. 6:325-45), ophthalmology (Ebrahim, S. et al. (2005) "*Applications of liposomes in ophthalmology,*" Surv. Ophthalmol. 50:167-82), pulmonology (Schreier, H. et al. (1993) "*Pulmonary delivery of liposomes,*" J. Control. Release 24:209-223), and numerous other pathologies (Moghimi, S. M. & Szebeni, J. (2003) "*Stealth liposomes and long circulating nanoparticles: critical issues in pharmacokinetics, opsonization and protein-binding properties,*" Prog. Lipid Res. 42:463-478; Tazina, E. V. et al. (2011) "*Qualitative and quantitative analysis of thermosensitive liposomes loaded with doxorubicin,*" Pharm. Chem. J. 46:54-59).

Tumor microvasculature is porous, with pore diameters large enough to allow nanoparticles smaller than several hundred nanometers to migrate into the extravascular space, providing a mechanism for liposome-encapsulated drugs to concentrate within tumors (Abraham. S. et al. (2005) "*The liposomal formulation of doxorubicin,*" Methods Enzymol. 391:71-97). Using this feature, liposomal anthracyclines have shown reduced toxicity compared with conventional delivery methods, while providing efficacies comparable with their conventional counterparts (O'Shaughnessy, J. (2003) "*Liposomal Anthracyclines for Breast Cancer: Overview,*" Oncologist 8:1-2). For example, Doxil®, the first FDA-approved nanoparticle drug, comprising the anthracycline antibiotic doxorubicin in PEGylated ~100 nm liposomes (Barenholz, Y. C. (2012) "*Doxil®—The First FDA-Approved Nano-Drug: Lessons Learned,*" J. Controlled Release 160:117-134), is widely used as a chemotherapeutic for treatment of a range of recurrent cancers, and there are various other liposomal drugs approved for clinical use (Chang, H. I. & Yeh, M. K. (2012) "*Clinical development or liposome-based drugs: formulation, characterization, and therapeutic efficacy,*" International J. of Nanomedicine 7:49-60; Wagner, V. et al. (2006) Nat. Biotechnol. 24:1211-7), with many more formulations in clinical trials.

Vesicle size and polydispersity are key parameters impacting the therapeutic index of liposomal drugs. Smaller liposomes are known to exhibit slower blood clearance rates, thereby increasing drug bioavailability (Chang, H. I. & Yeh, M. K. (2012) "*Clinical development or liposome-based drugs: formulation, characterization, and therapeutic efficacy,*" International J. of Nanomedicine 7:49-60; Litzinger, D. C. et al. (1994) "*Effect of liposome size on the circulation time and intraorgan distribution of amphipathic poly(ethylene glycol)-containing liposomes,*" Biochim. Biophys. Acta 1190:99-107). Various attempts have been made to investigate the impact of liposome size on cell uptake, intracellular transport and fate, and overall biodistribution for vesicles in the ~100 to ~1,000 nm range (Ramachandran, S. et al. (2006) "*Nanoliposomes for Cancer Thereapy: AFM and Fluorescence imaging of Cisplatin Encapsulation, Stability, Cellular Uptake and Toxicity,*" Langmuir 22:8156-8162; Kelly, C. et al. (2011) "*Targeted Liposomal Drug Delivery to Monocytes and Macrophages,*" J. Drug Delivery 2011, 727241; Ahsan, E. et al. (2002) "*Targeting to macrophages: role of physiochemical properties of particulate carriers—liposomes and microspheres—on the phagocytosis by macrophages,*" J. Controlled Release 79:29-40; Epstein-Barash, H. et al. (2010) "*Physicochemical parameters affecting liposomal bisphosphonates bioactivity for restenosis therapy: internalization, cell inhibition, activation of cytokines and complement, and mechanism or cell death,*" J. Controlled Release 146:182-195; Takano, S. et al. (2003) "*Physicochemical properties of liposomes affecting apoptosis induced by cationic liposomes in macrophages,*" Pharmaceutical Research 20:962-968; Pollock, S. et al. (2010) "*Uptake and trafficking of liposomes to the endoplasmic reticulum,*" The FASEB 24:1866-1878). In some studies, liposomes larger than 300 nm were not effectively taken up by cells in vitro, while smaller 100 nm liposomes exhibited rapid endocytosis (Ramachandran, S. et al. (2006) "*Nanoliposomes for Cancer Therapy: AFM and Fluorescence imaging of Cisplatin Encapsulation, Stability, Cellular Uptake and Toxicity,*" Langmuir 22:8156-8162). In other studies, 100 nm liposomes were found to maximize uptake into monocytes and macrophages compared with larger vesicles (Kelly, C. et al. (2011) "*Targeted Liposomal Drug Delivery to Monocytes and Macrophages,*" J. Drug Delivery 2011, 727241; Ahsan, E. et al. (2002) "*Targeting to macrophages: role of physicochemical properties of particulate carriers—liposomes and microspheres—on the phagocytosis by macrophages,*" J. Controlled Release 79:29-40; Epstein-Barash, H. et al. (2010) "*Physicochemical parameters affecting liposomal bisphosphonates bioactivity for restenosis therapy: internalization, cell inhibition, activation of cytokines and complement, and mechanism or cell death,*" J. Controlled Release 146:182-195; Takano, S. et al. (2003) "*Physicochemical properties of liposomes affecting apoptosis induced by cationic liposomes in macrophages,*" Pharmaceutical Research 20:962-968). In the case of liposomal doxorubicin, higher tumor uptake has been observed together with significantly lower uptake by healthy tissues when the mean vesicle size was reduced from 100 nm to 75 nm (Cuia, J. et al. (2007) "*Direct comparison of two pegylated liposomal doxorubicin formulations: is AUC predictive for toxicity and efficacy?*" J. Controlled Release 118:204-215). As such, questions remain about the impact of liposome size on cell uptake and internalization for vesicles smaller than about 100 nm, in part due to limitations imposed by most existing liposome preparation techniques.

Thus, a challenge to liposomal drug delivery technologies has been the effective control over vesicle size during synthesis. The ideal size for cancer-targeting liposomal nanomedicines is commonly believed to be about 100 nm, which is thought to be large enough to provide a high drug payload volume while small enough to pass through leaky endothelial junctions in tumor tissues (Fenske, D. B. et al. (2008) "*Liposomal nanomedicines: an emerging field,*" Toxicologic Pathology 36:21-29). However, such view ignores the increasing use of liposomes for lipophilic drug encapsulation within the vesicle membrane where loading efficiency scales inversely with liposome size, and also ignores the impact of vesicle size on key parameters affecting drug efficacy and safety, including cellular uptake, cellular fate, and overall biodistribution. Relationships between such key characteristics and liposome size are not fully understood for nanoparticles below 100 nm, in large part because many conventional bulk synthesis techniques yield relatively large and polydisperse liposome populations that render detailed size-dependent studies difficult.

Another challenge hampering liposomal delivery systems has been the development of effective methods for loading high concentrations of therapeutic agent(s) or drug into lipid vesicles. Increased drug-to-lipid ratio (D/L) is a highly desirable attribute for liposome delivery systems, given in vivo toxicity is inversely related to D/L (Mayer, L. D. et al. (1989) "*Influence of Vesicle Size, Lipid Composition, and Drug-to-Lipid Ratio on the Biological Activity of Liposomal Doxorubicin in Mice*" Cancer Res. 49:5922-5930). For example, nanoparticle delivery systems can enhance the therapeutic index of anti-cancer agents by increasing drug concentration in tumor cells. The increased drug concentration facilitated by nanoparticle delivery is the result of enhanced nanoparticle permeability and retention in tumor tissues (Matsumura, Y. & Maeda. H. (1986) "*A new concept for macromolecular therapeutics in cancer chemotherapy: mechanism of tumoritropic accumulation of proteins and the antitumor agent SMANCS,*" Cancer Res 6:193-210; Maeda, H. (2010) "*Tumor-selective delivery of macromolecular drugs via the EPR effect: background and future prospects,*" Bioconjugate Chemistry 21:797-802), together with the use of molecular targeting strategies that enhance tumor cell uptake (Moses, M. A., Brem. H. & Langer. R. (2003) "*Advancing the field of drug delivery: taking aim at cancer,*" Cancer Cell 4:337-341; Liu, Y. et al. (2007) "*Nanomedicine for drug delivery and imaging: a promising avenue for cancer therapy and diagnosis using targeted functional nanoparticles,*" International J. Cancer 120:2527-2537; Cho, K. et al. (2008) "*Therapeutic nanoparticles for drug delivery in cancer,*" Clin. Cancer Research 14:1310-1316).

A variety of liposomal drug synthesis techniques have been reported (Otake. K. et al. (2006) "*Preparation of liposomes using an improved supercritical reverse phase evaporation method,*" Langmuir The ACS Journal of Surfaces and Colloids 22:2543-2550; Uhumwangho, M. U. & Okor, R. S. (2005) "*Current trends in the production and biomedical applications of liposomes: a review,*" Sciences New York 4:9-21; Jiskoot, W. et al. (1986) "*Preparation of liposomes via detergent removal from mixed micelles by dilution. The effect of bilayer composition and process parameters on liposome characteristics,*" Pharmaceutisch Weekblad Scientific Edition 8:259-265; Szoka, F. & Papahadjopoulos, D. (1978) "*Procedure for preparation of liposomes with large internal aqueous space and high capture by reverse phase evaporation,*" Proceedings of the National Academy of Sciences of the United States of America 75:4194-4198; Meure, I. A. et al. (2008) "*Conventional and Dense Gas Techniques for the Production of Liposomes: A Review,*" Aaps Pharmscitech 9:798-809).

Conventional liposome preparation is based on demanding bulk-scale processes which include a variety of traditional methods including ethanol injection, reverse-phase evaporation, detergent depletion, emulsification, supercritical phase formation, membrane extrusion, thin-film hydration, rapid solvent exchange, which all require post-processing steps such as sonication or membrane extrusion to regulate the size and reduce the polydispersity of the final population of liposomes (Jesorka, A. & Orwar, O. (2008) "*Liposomes: technologies and analytical applications*" Annu. Rev. Anal. Chem. (Palo Alto. Calif. 1:801-32). In addition, such techniques require further processing steps for drug encapsulation, membrane functionalization, purification, and concentration. Conventional bulk methods are therefore cumbersome, time consuming, and labor intensive, and result in liposomal nanomedicines with limited shelf life due to drug leakage and lipid degradation. Moreover, even after repeated processing steps utilizing bulk techniques, such as sequential membrane extrusion or size exclusion chromatography, the resulting vesicles tend to be relatively large (>100 nm) and polydisperse. For example, when performing 6-step membrane extrusion to reduce liposome size and polydispersity, relative standard deviations above 50% are observed (Berger, N. et al. 2001) "*Filter extrusion of liposomes using different devices: comparison of liposome size, encapsulation efficiency, and process characteristics,*" International Journal of Pharmaceutics 223:55-68). In addition, conventional bulk synthesis and encapsulation methods often lead to significant agent loss with waste that can approach 98% for hydrophilic drug compounds (Lasic, D. D. (1998) "*Novel applications of liposomes,*" Trends in Biotechnology 16:307-321; Nagayasu, A. et al. 1999) "*The size of liposomes: a factor which affects their targeting efficiency to tumors and therapeutic activity or liposomal antitumor drugs,*" Advanced Drug Delivery Reviews 40:75-87).

Because conventional bulk synthesis yields relatively large and polydisperse liposomes, detailed size-dependent behaviors for smaller vesicles have proven difficult or impossible to study. As a result, studies of size-dependent behaviors have largely focused on the use of inorganic nanoparticles such as gold (Chithrani, B. D. et al. (2006) "*Size and Shape Dependence of Nanoparticles on Cellular Uptake,*" Nano 668:662-668; Shan, Y. et al. (2009) "*Size-dependent endocytosis of single gold nanoparticles,*" Chemical Communications 47:8091-8093; Zhang, S. et al. (2009) "*Size-Dependent Endocytosis of Nanoparticles,*" Advanced materials Deerfield Beach Fla. 21:419-424; Cho, E. C. et al. (2011) "*Cellular uptake of gold nanoparticles,*" Cancer Cell 6:385-391), carbon (Jin, H. et al. (2009) "*Size-dependent cellular uptake and expulsion of single-walled carbon nanotubes: single particle tracking and a generic uptake model for nanoparticles,*" ACS nano 3:149-158), iron oxide (Huang, J. et al. (2010) "*Effects of nanoparticle size on cellular uptake and liver MRI with polyvinylpyrrolidone-coated iron oxide nanoparticles,*" ACS nano 4:7151-7160), and silica (Kumar, S. et al. (2012) "*Size Dependent Interaction of Silica Nanoparticles with Different Surfactants in Aqueous Solution,*" Langmuir 28(25):9288-9297, which materials can be synthesized with relatively tight control over size and with low polydispersity. However, because surface properties of such inorganic nanoparticles are entirely different from liposomes, which closely mimic the native cell walls across which endocytosis occurs, the results of such studies cannot be translated and is thus not relevant to liposomal drug delivery.

Microfluidic technologies have been attempted to alleviate some of the shortcomings of conventional bulk-scale liposome production methods (Andar, A. U. et al. (2014) "*Microfluidic Preparation of Liposomes to Determine Particle Size Influence on Cellular Uptake Mechanisms*" Pharm. Res. 31:401-13; Hood, R. R. et al. (2014) "*Microfluidic-Enabled Liposomes Elucidate Size-Dependent Transdermal Transport,*" PLoS One 9:e92978). Controlled liposome formation utilizing a microfluidic hydrodynamic flow-focusing (MHF) technique substantially decreases size variance, with fewer processing steps. Compared to conventional bulk-scale techniques, traditional MHF methods provide nanoparticles with enhanced properties including adjustable, narrowly distributed diameters (Jahn, A. et al. (2004) "*Controlled Vesicle Self-Assembly in Microfluidic Channels with Hydrodynamic Focusing,*" J. Am. Chem. Soc. 126:2674-2675; Jahn, A. et al. (2007) "*Microfluidic Directed Self-Assembly of Liposomes of Controlled Size,*" Langmuir 23:6289-6293; Jahn, A. et al. (2008) "*Preparation of nanoparticles by continuous-flow microfluidics,*" J. Nanoparticle Res. 10:925-934; Jahn, A. et al. (2010) "*Microfluidic mixing and the formation of nanoscale lipid vesicles,*" ACS nano 4:2077-2087), and tunable physiochemical properties (Hood, R. et al. (2013) "*Microfluidic synthesis of PEGylated and folate receptor-targeted liposomes,*" Pharm. Res. 30:1597-607). However, realtively low throughput has been achieved by traditional microfluidic systems, which has constrained MHF methods for use in bulk production (e.g., such as for large scale in vivo studies and preclinical trials where larger volumes and higher concentrations are required). Thus, sufficient throughput and nanoparticle concentration have not been achieved utilizing traditional microfluidic techniques.

Accordingly, there is a need for microfluidic methodologies and systems that overcome some or all of the above-noted limitations and/or disadvantages.

SUMMARY OF THE INVENTION

The present invention relates to microfluidic devices, systems and methods for on-demand formation of agent-loaded liposomal nanoparticles, with clinically useful doses prepared in minutes rather than hours or days. The disclosed systems and methods provide for sequential liposome formation, purification, vesicle functionalization for tissue targeting, and active drug loading. In accordance with disclosed embodiments, a microfluidic system combines liposome formation with in-line sample purification and remote drug loading for single step, continuous-flow synthesis of nanoscale vesicles containing high concentrations of stably loaded drug compounds and/or other therapeutic or diagnostic agents. Using an on-chip microdialysis element, the system enables rapid formation of large transmembrane pH or ion gradients, followed by immediate introduction of amphipathic drug for real-time remote loading into the liposomes. Thus, the liposomes may be loaded efficiently and effectively in a continuous flow process enabled by steep transmembrane ion gradients, which decrease over time. The microfluidic process enables in-line formation of drug-laden liposomes with drug:lipid molar ratios of up to 1.3 or more, and a total on-chip residence time of approximately 10 minutes or less, representing a significant improvement over conventional bulk-scale methods which require hours to days for combined liposome synthesis and remote drug loading. The microfluidic platform may be utilized to support real-time generation of purified liposomal drug formulations with high concentrations of drugs and minimal reagent waste for effective liposomal drug preparation at or near the point of care. Prior methods have failed to provide active drug encapsulation as part of an on-line liposome synthesis process.

The present invention also relates to microfluidic systems, devices and methods that enable high throughput synthesis of nanoscale liposomes utilizing high aspect ratio hydrodynamic flow-focusing (HAR-MHF) methods. HAR-MHF systems feature high aspect ratio microchannels in which one cross-sectional dimension of the focusing channel (e.g., width) is significantly greater than a second cross-sectional dimension (e.g., height), as compared to conventional microfluidic devices. The use of high aspect ratio channels enables high throughput production of nanoparticles while also preserving size control and low levels of polydispersity (comparable to or exceeding that exhibited by traditional MHF systems). Such microfluidic-generated liposomes may be produced at speeds which render it feasible for large scale in vivo experiments, preclinical studies, pilot-scale nanoparticle production, etc.

A microfluidic system for continuous flow synthesis and active loading of liposomes in accordance an embodiment of the present invention comprises a substrate having a sample flow channel having a liposome formation region, a transmembrane gradient formation region, and an agent loading region. In some embodiments, the substrate is comprised of a thermoplastic material. The liposome formation region comprises an inlet through which a lipid solution flows and inlets through which a buffer solution flows. The lipid solution and the buffer solution interact within the sample flow channel and form a population of liposomes in a sample buffer solution. The transmembrane gradient formation region is configured to establish a liposome transmembrane gradient. The agent loading region comprises an inlet through which a first agent flows and in fluid connection with the sample flow channel. The first agent is mixed with the liposomes received from the transmembrane gradient formation region, and actively loaded within intravesicular spaces of the liposomes.

In some embodiments, the transmembrane gradient formation region is a microdialysis region. In some implementations, the microdialysis region is a counterflow microdialysis region. The microdialysis region may comprise a counterflow channel adjacent to the sample flow channel, and a membrane in between or intermediate the sample flow channel and the counterflow channel. The membrane permits buffer exchange between the sample flow channel and the counterflow channel and establishes a transmembrane ion gradient.

In some embodiments, the formed liposomes have a median diameter of between about 20 nm and about 500 nm, and in some implementations between about 20 nm and about 100 nm. In some embodiments, the liposomes have a percent polydispersity of less than about 10%, and in some implementations less than about 5%.

In some embodiments, the liposome formation region also comprises an inlet through which a second agent flows, whereby the second agent is passively entrapped within or conjugated to the liposomes during formation.

In some embodiments, the population of liposomes are formed and actively loaded in the microfluidic system in less than 1 hour. In some implementations, the transmembrane gradient formation region effectuates a shift of pH of said sample buffer solution sufficient to enable active loading of the first agent within the liposomes and in less than about 5 minutes. In some implementations, the first agent is selected from the group consisting of an anthracycline, an amphotericin, cytarabine, and chlorpromazine. In some implementations, the first agent is an amphipathic peptide or protein. In some embodiments, the liposomes loaded with the first agent exhibit a drug-to-lipid molar ratio of greater than 0.5, in some implementations greater than 2.0.

A microfluidic system having a sample flow channel for continuous flow synthesis and active loading of liposomes according to an embodiment of the present invention comprises a liposome formation region configured to receive a lipid solution and buffer solution, and form a population of liposomes in a sample buffer solution, and a microdialysis region downstream from and in fluid connection with said liposome formation region and configured to form a liposome transmembrane ion gradient. In some embodiments, the system further comprises a drug-loading region downstream from and in fluid connection with the microdialysis region and configured to entrap an agent within the liposomes.

In some implementations, the microdialysis region comprises a counterflow channel adjacent to the sample flow channel, and a membrane between the sample flow channel and the counterflow channel. The membrane permits buffer exchange between the sample flow channel and the counterflow channel for enabling removal of free ions from the sample buffer solution. In some implementations, the membrane prevents selected particles or molecules from passing between the sample flow channel and the counterflow channel.

The present invention also relates to a method for continuous flow synthesis and active drug loading of liposomes, comprising the steps of: forming a population of liposomes within a buffer solution in a microfluidic channel; establishing a transmembrane pH gradient between an intravesicular space within the liposomes and the buffer solution; and entrapping an agent into the intravesicular space via directed ion exchange to form agent-loaded liposomes. In some implementations, the liposomes are formed and loaded in less than about 1 hour. In some implementations, the liposomes are formed and loaded in less than about 10 minutes.

The present invention is also directed to a microfluidic device for synthesis of liposomes. The device comprises a sample flow channel, a first inlet channel in fluid communication with the sample flow channel, and second and third inlet channels in fluid communication with the sample flow channel. The first, second and third inlet channels converge at a flow focusing region within the sample flow channel, wherein the sample flow channel has an aspect ratio (height:width) exceeding 20:1 at the flow focusing region. In some implementations, the aspect ratio is 50:1 or greater. In some implementations, the aspect ratio is 100:1 or greater. The first, second and third inlet channels are preferably vertically oriented relative to each other.

BRIEF DESCRIPTION OF THE DRAWINGS

The file of this patent contains at least one drawing/photograph executed in color and that copies of this patent with color drawing(s)/photograph(s) will be provided by the Office upon request and payment of the necessary fee.

FIG. 10, panel a depicts the ammonium sulfate concentration throughout the microdialysis segment of the device (channel length scaled by a factor of 10 for more rapid computation). FIG. 10, panel b depicts concentration profile of ammonium sulfate along the sample channel, RC membrane, and counterflow channel at the exit of the dialysis region for flow velocities varying from 0.3 cm s$^{-1}$ to 0.6 cm s$^{-1}$.

FIG. 13, panel b is a photograph of an actual HAR-MHF device consisting of COC plaques and thin (50 µm) films produced using simple fabrication techniques.

DETAILED DESCRIPTION OF THE INVENTION

The present invention relates to systems, devices and methods for sequential liposome formation, purification, and active drug loading based on the use of a transmembrane pH or ion concentration gradient established using an on-chip microdialysis membrane. The microfluidic system provides single-step continuous-flow synthesis of vesicles encapsulating both lipophilic and amphipathic drugs with minimal reagent waste. The liposomes may have a selected size, for example having vesicle diameters of about 20 nm to about 300 nm, with the selected population size exhibiting extremely low levels of polydispersity. In accordance with some disclosed embodiments, systems and methods are provided that enable high throughput synthesis of nanoscale liposomes.

Figure 1:
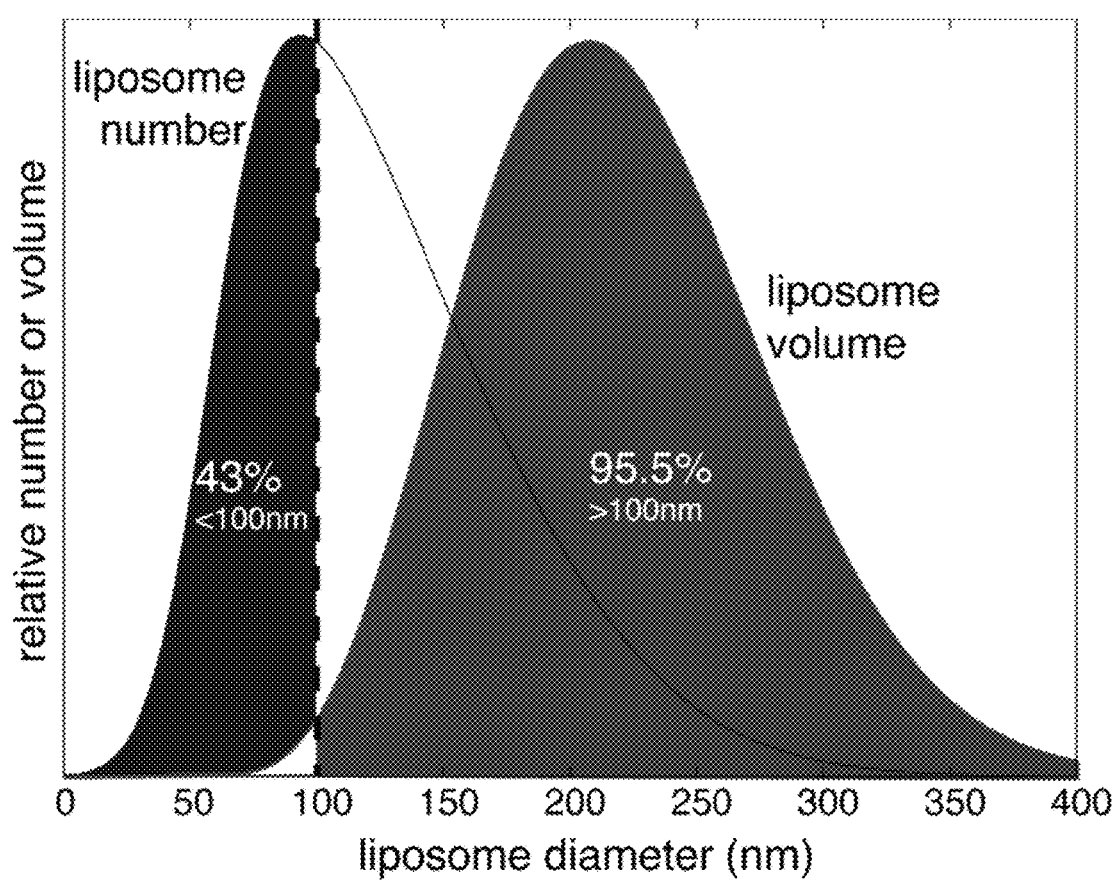
FIG. 1 is a graphical representation of liposome size distribution and resulting volume distribution for a population prepared by a conventional membrane extrusion method. While nearly half of the liposomes are below 100 nm in diameter, these smaller liposomes represent less than 0.5% of the total volume of the sample.

Disclosed methods and systems enable controllable formation of small and uniform liposomes, thereby allowing for an accurate determination of the impact of relatively small liposomes (e.g., with vesicles less than 100 nm, and as small as 20 nm) for drug delivery applications. Large size variability of liposome populations can have a significant negative impact on toxicity. As noted above, liposomal drugs prepared by traditional methods exhibit skew normal size distributions with large variance, even after multiple processing steps (e.g., membrane extrusion or gel filtration) to improve size homogeneity (see Maguire, L. A. et al. (2003) "*Preparation of small unilamellar vesicles (SUV) and biophysical characterization of their complexes with poly-1-lysine-condensed plasmid DNA,*" Biotechnology and Applied Biochemistry 37:73-81). For example, size variation data in a liposome population prepared by a conventional 5-step extrusion process is shown in FIG. 1. The left-hand curve presents the distribution of measured liposome diameters, while the right-hand curve reflects the resulting liposome volume distribution. While 43% of the measured liposomes are below 100 nm in diameter, liposomes larger than 100 nm account for more than 99.5% of the total volume (drug dose). Similarly, although the mode of the size distribution is 95 nm in measured liposomes, the mode of the volume distribution is 204 nm in total volume. Thus, as demonstrated in FIG. 1, a fundamental problem with liposomal carriers prepared by traditional bulk synthesis methods is large size variance. Even moderate variance in liposome size results in a large amount of encapsulated drug being introduced by vesicles outside of the desired size range, necessitating the delivery of a larger total drug amount to achieve a given therapeutic index from vesicles within the optimal range, thus resulting in potential increase in toxicity and degraded safety profiles.

Controlled liposome formation utilizing microfluidic hydrodynamic flow-focusing (MHF) substantially decreases size variance (Jahn, A. et al. (2004) "*Controlled Vesicle Self-Assembly in Microfluidic Channels with Hydrodynamic Focusing,*" J. Am. Chem. Soc. 126:2674-2675; Jahn, A. et al. (2007) "*Microfluidic Directed Self-Assembly of Liposomes of Controlled Size,*" Langmuir 23:6289-6293). A much higher percentage of vesicles within a selected and optimal range may be achieved, thereby lowering total drug amount required for the same therapeutic index and significantly improving safety profiles. In MHF techniques, liposomes are formed by a diffusively driven process wherein a stream of lipid solvated in an alcohol is hydrodynamically sheathed between two oblique aqueous streams within a microfluidic channel. The lipid stream is focused into a narrow sheet with a thickness varying from a few micrometers to several hundred nanometers, depending on the lipid:buffer flow rate ratio. The laminar flow conditions facilitate highly controllable diffusive mixing at the two miscible liquid interfaces, diluting the alcohol concentration below the lipid solubility limit and initiating lipid self-assembly into small unilamellar vesicles. For example, a central stream of phospholipids dissolved in 2-propanol (IPA) may be focused by outer streams containing a narrow inner sheath of green carboxyfluorescein dye as a model encapsulant, with an outer sheath of aqueous buffer used to define the degree of focusing.

In contrast to other microfluidic techniques based on electroformation (e.g., see Kuribayashi, K. et al. (2006) "*Electroformation of giant liposomes in microfluidic channels,*" Measurement Science and Technology 3212 (2006) or crossflow injection (Wagner, A. et al. (2002) "*The crossflow injection technique: An improvement of the ethanol injection method,*" J. Liposome Res 12:259-270), MHF techniques generate a large, controllable, and spatially-varying solvent gradient, which is believed to be responsible for the formation of highly uniform vesicles with average diameters that can be adjusted by simply modifying the flow rate ratio. Liposome populations with average liposome diameters ranging from about 50 nm to 150 nm have been achieved with relative standard deviations of about 10-15% utilizing traditional MHF methods (see Jahn, A. et al. (2007) "*Microfluidic Directed Self-Assembly of Liposomes of Controlled Size,*" Langmuir 23:6289-6293).

Disclosed embodiments of microfluidic flow focusing systems of the present invention further extend the selected vesicle size range from about 20 nm to about 500 nm, while dramatically reducing polydispersity in the resulting liposome populations to less than about 10%, more preferably less than about 5%. The disclosed methodologies and systems therefore allow for precise comparisons of in vitro and in vivo performance over a wide vesicle size range without the confounding influence of high polydispersity.

Early microfluidic flow-focusing chips were fabricated using a cumbersome silicon/glass process. In contrast, embodiments of the present invention provide for a robust thermoplastic microfabrication method that supports rapid prototyping of different device designs, improves vesicle size range and greatly reduces polydispersity. A fully integrated liposomal drug synthesis process is provided, which includes vesicle formation, lipophilic and amphipathic drug encapsulation, vesicle functionalization for molecular targeting, vesicle concentration, and liposomal drug purification. The thermoplastic microfabrication method supports low-cost scale-up of the technology for producing clinically-acceptable volumes of targeted liposomal drugs in a single continuous-flow process. Thus, a fully integrated pharmacy-on-a-chip platform is achieved, enabling production of a new generation of size-optimized, targeted and multi-agent liposomal drugs.

The microfluidic process of the present invention may be implemented for facile production of custom liposomal drugs for preclinical or clinical research applications, scaled up as part of a larger scale production pipeline, or implemented for point-of-care applications. Liposomes dispersed in aqueous solution are subject to physical and chemical instabilities during long-term storage, including lipid hydrolysis and oxidation, liposome aggregation, and liposome fusion (see Chen, C. et al. (2010) "*An overview of liposome lyophilization and its future potential,*" J. Controlled Release 142:299-311). Loss of encapsulated drugs due to membrane leakage (e.g., such as during long-term storage) reduces the therapeutic efficiency of liposomal drugs over time. For example, storage of siRNA-loaded liposomes at 4° C. for one month has been observed to result in significant encapsulant leakage and an 80% decrease in gene silencing efficiency (Chang, H. I. & Yeh, M. K. (2012) "*Clinical development or liposome-based drugs: formulation, characterization, and therapeutic efficacy,*" International J. of Nanomedicine 7:49-60). As such, conventional liposomal drug suspensions are typically stated as having shelf lives ranging from 12 to 20 months, with lipid species selected for enhanced stability rather than for their therapeutic efficacy. Even in the case of Doxil®, which is subject to minimal leakage since the majority of the encapsulated doxorubicin is stored in a crystallized state, up to 10% of the encapsulated drug can leak from the vesicles during storage over its 20 month shelf life.

Furthermore, the size distributions of stored liposomal drugs change over time due to vesicle fusion. While lyophilization of liposomes can avoid this latter concern and further extend storage times, the freeze drying process itself results in significant drug leakage and vesicle fusion (Chen, C. et al. (2010) "*An overview of liposome lyophilization and its future potential,*" J. Controlled Release 142:299-311). The microfluidic process of the present invention offers an innovative approach to preparing on-demand nanoliposome drugs for almost immediate use in experimental or point-of-care settings. As such, lipid compositions and bioactive agents tailored for optimal performance may be utilized without regard for long-term stability. Point-of-care liposomal drugs may be prepared in accordance with the disclosed systems and methodologies, with targeting ligands customized to a patient's specific disease profile.

The microfluidic liposome formation process of the present invention provides for dynamic control over vesicle size. The microfluidic flow-focusing technique is optimized to produce smaller and more uniform liposome populations compared to those achievable using prior bulk or traditional microfluidic methods. Using a high aspect ratio microchannel fabrication method, the formation of nearly-monodisperse liposome populations with a selected size within a wider size range and with lower size variance is achieved.

In prior preparation methods utilizing a bulk alcohol injection process, a stream of lipids in alcohol is injected into a vortexed aqueous buffer under high Reynolds number flows. However, the bulk alcohol injection process does not allow for controlled mixing conditions or solvent gradients, and is sensitive to perturbations in the mixing conditions which result in large shifts in mean liposome diameter and size variance. In contrast, the techniques disclosed herein afford exquisite control over the local flow conditions, and enable the formation of small liposomes with tightly controlled distributions.

Based on the disclosed studies of the present invention, liposome size is believed to be inversely related to the aqueous:alcohol flow rate ratio, and remains independent of the total flow rate. The interpretation of this relationship is that at higher flow rate ratios the focused lipid stream is narrowed, resulting in a more rapid decrease in alcohol concentration within the focused stream. As a result, the time scale between initial formation of single lipid layers, or lipid "leaflets," and the collapse of leaflets into closed and fully assembled liposomes is reduced, resulting in reduced leaflet growth and thus smaller vesicles. Maintaining uniform focusing of the lipid stream at each channel cross-section thus achieves uniform liposome populations, since variations in the stream width lead to variations in diffusion time scales and thus wider liposome size distributions.

Early flow-focusing chips fabricated in etched silicon substrates had channel aspect ratios (height:width) that were substantially uniform (i.e., ~1). Due to the parabolic flow profile associated with pressure-driven microchannel flow in such early chips, with no-slip conditions imposed at the channel walls, the lipid stream at the upper and lower surfaces of the focusing channel is not focused by the aqueous sheath flows, and thus contributes to unwanted variance in the size distribution. Furthermore, differences in focused stream width increase with the flow rate ratio, leading to higher variance for smaller liposomes and placing a limit on the minimum vesicle size that can be generated using such early techniques. For example, by using a silicone elastomer soft lithography process supporting a 4:1 channel aspect ratio, a wider range of liposome sizes ranging from about 40 nm to about 277 nm was achieved with variance below 8% over the full size range.

In accordance with embodiments of the present invention, vesicle size control is further improved by implementing a dry film photoresist thermoplastic microfabrication process capable of providing significantly higher aspect ratio channels than those previously attempted. Thermoplastic cyclic olefin copolymer (COC) is a preferred substrate material for the flow-focusing chip due to its low material cost, compatibility with patterning by rapid replication methods such as roll-to-roll hot embossing, excellent solvent compatibility, and capabilities for heterogeneous material integration. While thermoplastic microchannels are typically limited to low aspect ratios, this limitation has been overcome through the use of a multi-layer dry film photoresist patterning process.

Dry film resists (DFRs) are thick sheets of photopatternable epoxy-based resist sometimes employed for circuit board patterning, but which have not previously been utilized in nanoparticle synthesis. Unlike photopatterned molds fabricated from thick spin-coated photoresists (e.g., SU-8), the continuous DFR sheets are applied by lamination and thus multiple layers can be applied even after patterning the underlying films. Furthermore, unlike silicon molds, the tough DFR molds do not readily fracture during the embossing process. This combination of features makes DFR molds preferred for replica molding of high aspect ratio thermoplastic chips. For example, individual 30 μm thick DFR layers can be patterned with about 10 μm to about 15 μm lateral features for an aspect ratio of at least 2:1. The photolithography process may be further optimized for sequentially processing 5 or more DFR layers for an overall aspect ratio of 10:1 or greater. Using this process, a wider range of liposome sizes may be achieved, for example ranging from about 20 nm to about 500 nm, more preferably from about 20 nm to about 300 nm, more preferably from about 20 nm to about 100 nm, and with low size variation, preferably less than about 10%, more preferably less than about 5%. Thus, the disclosed methodologies represent an order-of-magnitude reduction in polydispersity over prior bulk membrane extrusion processes (e.g., see Berger, N. et al. 2001) "*Filter extrusion of liposomes using different devices: comparison of liposome size, encapsulation efficiency, and process characteristics,*" International Journal of Pharmaceutics 223:55-68). Moreover, the relationships between liposome size distributions and system-level parameters that are accessible to the chip designer may be optimized as desired, including channel width, channel aspect ratio, and flow-focusing intersection geometry.

The flow-focusing process has also been extended to a wider range of lipids and lipid formation conditions than previously attempted. In previous methods, liposomes were formed using the neutral lipid dimyristoyl phosphatidylcholine (DMPC), combined with cholesterol and dihexadecyl phosphate (DCP) in a molar ratio of 5:4:1 (Kuribayashi, K. et al. (2006) "*Electroformation of giant liposomes in microfluidic channels,*" Measurement Science and Technology 17:3121; Jahn, A. et al. (2010) "*Microfluidic mixing and the formation of nanoscale lipid vesicles,*" ACS nano 4:2077-2087; Hood, R. et al. (2013) "*Microfluidic Synthesis of PEG- and Folate-Conjugated Liposomes for One-step Formation of Targeted Stealth Nanocarriers,*" Pharm. Res. 30:1597-1607). In the present invention, the flow-focusing process may be utilized with other neutral lipids with different fatty acid chain lengths (DOPC and DLPC), as well as an anionic lipid (DOPC).

In accordance with embodiments of the present invention, a microfluidic system is provided that enables rapid and efficient active or remote loading of an agent(s) or drug(s) into nanoscale liposomes, combining liposome synthesis and remote drug loading in a continuous integrated process. Conventional bulk methods for remote drug loading require a series of discrete manual operations using large fluid volumes. In addition, prior microfluidic methods, although providing some advantages over conventional bulk preparation methods, have been limited to passive drug encapsulation and require off-chip sample purification to remove residual solvents or non-encapsulated reagents. During passive loading, the desired drug is added to the lipid mixture prior to vesicle formation, whereby the drug becomes sequestered within the liposomes during the self-assembly process. However, passive encapsulation is inefficient, with less than 10% encapsulation efficiencies typically achieved for hydrophilic compounds, resulting in significant waste of valuable drug. In addition, the maximum attainable D/L ratio during passive loading is limited by drug solubility (Cullis, P. R. et al. (1989) Adv. Drug Delivery Rev. 3:267-282), constraining the total amount of drug that can be encapsulated. Further, in the case of amphipathic drugs that possess both hydrophilic and hydrophobic regions, drug encapsulated by prior methods ultimately migrates out of the vesicles, resulting in varying concentration levels over time (Abraham, S. A. et al. (2005) Methods Enzymol., 391:71-97).

In contrast, liposome formation and drug-loading techniques in accordance with disclosed embodiments provide for a counterflow microdialysis element, which enables steep transmembrane pH or ion gradients to be formed immediately prior to active or remote drug loading of the formed liposomes. In some embodiments, a microfluidic device includes a sample flow channel including a continuous flow path that proceeds from a liposome formation region to a microdialysis region, and then to a drug-loading region (e.g., see FIG. 7, panel a). The liposome formation region may include an inlet through which a lipid solution is injected, as well as inlets through which buffer solutions are injected, followed by and in fluid communication with a liposome stabilization channel. In some implementations, a first agent or drug may be introduced in the liposome formation region for passive encapsulation during the assembly process (e.g., see FIG. 3).

The formed liposomes in sample buffer solution then proceed through a membrane dialysis or buffer exchange region. A counterflow channel is provided in the membrane dialysis region, through which a dialysis buffer solution flows in a direction opposite to or against the direction of flow of the sample buffer solution (e.g., see FIG. 7, panel b). The pH of the sample buffer solution is less than the pH of the dialysis or counterflow buffer solution. A membrane is disposed between the sample flow channel and the counterflow channel, permitting buffer exchange between the sample flow channel and the counterflow channel and thus establishing a liposomal transmembrane pH gradient.

Figure 7:
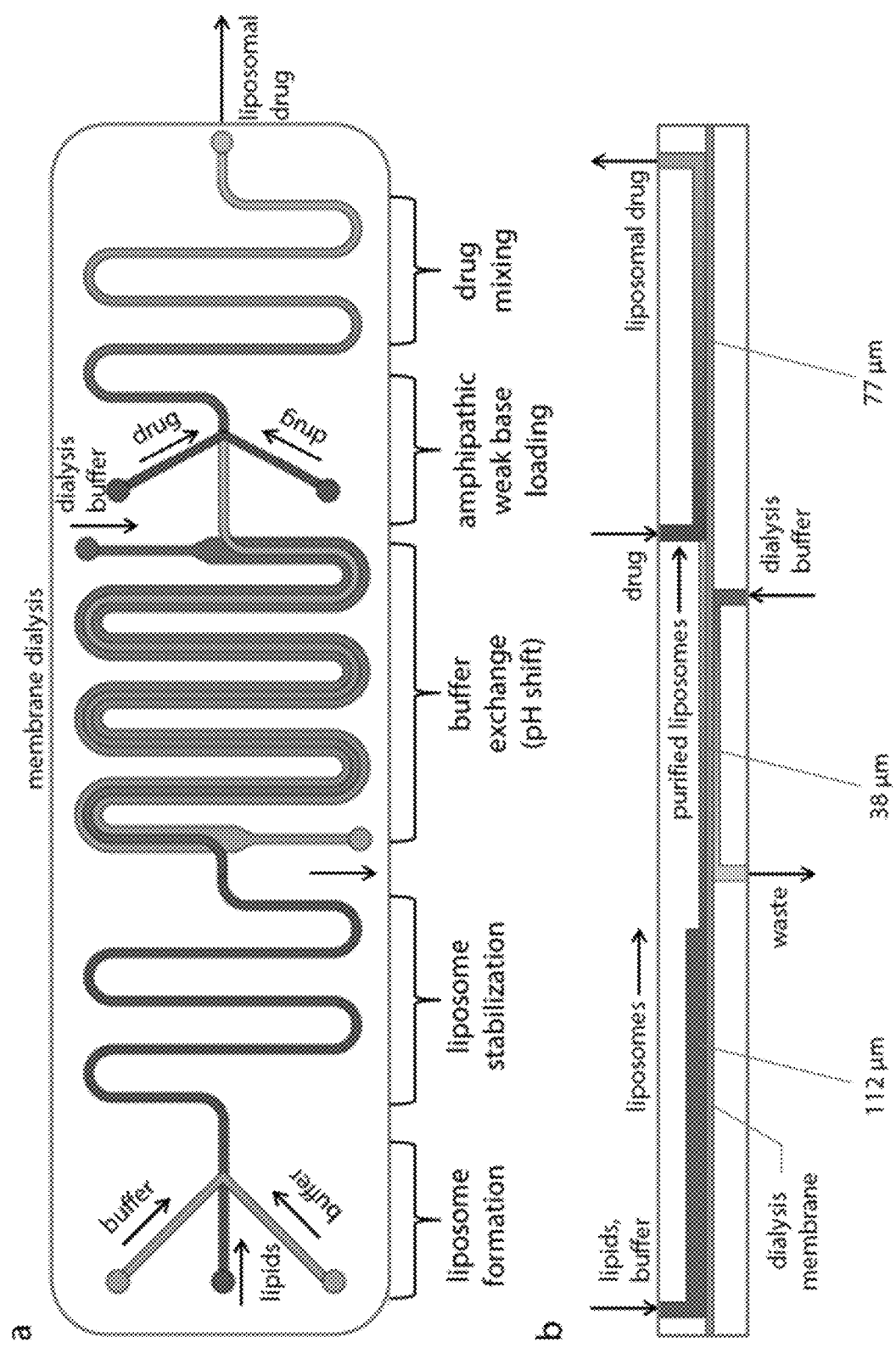
FIG. 7 illustrates schematic representations of a fully-integrated microfluidic device in accordance with an embodiment of the present invention for remote loading of liposomal therapeutic nanomedicines in-line with liposome synthesis and buffer exchange via microdialysis for rapid generation of nearly monodisperse, functionalized liposomes with tunable diameters containing high concentrations of stably loaded compounds (FIG. 7, panel a). A cross-sectional view of the microfluidic system is shown in FIG. 7, panel b, revealing the differing channel heights supporting each process step.

Immediately after formation of the transmembrane gradient, the liposomes flow into the drug loading region where an agent or drug is introduced and encapsulated (see FIG. 7, panel a). Drug encapsulation via active or remote loading takes advantage of the transmembrane chemical gradients to entrap the agent from the surrounding environment (i.e., the extravesicular spaces) into the already formed liposomes (i.e. within the intravesicular spaces). During the remote loading process, the agent or drug (e.g., amphipathic drug) diffuses through the bilayer lipid membrane into the intravesicular space within the liposome. Once inside the liposome, a chemical modification of the drug occurs, preventing membrane repermeation and thereby resulting in the accumulation of drug within the liposomes.

Some embodiments of microfluidic devices or chips provide for active or remote drug loading using a pH gradient to encapsulate the drug (e.g., amphipathic weak bases). In this approach, liposomes are initially formed in an acidic environment. After vesicle self-assembly, the interior of the liposome remains acidic while the extravesicular pH level is adjusted to physiological conditions. Incubation with uncharged drug allows molecules to diffuse into the liposomal intravesicular cavity, where the drug molecules then become protonated. The positively charged drug molecules can no longer traverse the bilayer membrane and are thus effectively trapped inside the liposomes.

Other chip embodiments provide for remote loading using a transmembrane ion gradient, for example for loading of amphipathic weak bases and/or acids. In this approach, liposomes are formed with a high concentration of a suitable ionic species selected to act as a counterion to the amphipathic drug. As the drug crosses the liposome membrane, it is rapidly formed into an insoluble salt through ionization, resulting in the formation of an insoluble salt which cannot diffuse back into the extravesicular environment, resulting in exceptionally high loading levels and improved liposome stability during storage and circulation.

Other chip embodiments provide for a combination of passive and active loading in a continuous flow process. An integrated microfluidic chip is provided for vesicle formation, PEGylation, targeting molecule attachment, and multi-agent encapsulation of amphipathic and lipophilic drugs, with a first agent entrapped during liposome formation via passive loading, and additional and/or a second agent entrapped within the formed liposomes via active loading. For passive loading, tertiary channels may be provided through which solvated compounds are injected for encapsulation during liposome formation. The differential solubility of lipophilic drugs directs diffusion toward the center of the stream where vesicle formation occurs.

Any of the disclosed systems and methods may be scaled up for large-volume and/or on-demand production, such as for point-of-care and clinical dosing levels. In accordance with embodiments of the present invention, a high aspect ratio microfluidic hydrodynamic flow-focusing (HAR-MHF) system is provided featuring high aspect ratio microchannels composed of extremely wide channel widths and relatively narrow channel heights, enabling high throughput production of nanoparticles while preserving size control and low polydispersity. In some implementations, liposomal synthesis techniques are carried out utilizing devices having microchannels with unique flow focusing axis orientation. Due to the orientation of the flow focusing axis, HAR-MHF combines the advantages of traditional MHF with the benefits of also providing extremely high aspect ratios for exceedingly uniform flow profiles and amplified production rates. Governed by the same physics as MHF for controlled liposome self-assembly, HAR-MHF reduces the necessary amount of parallelization, thus further increasing sample homogeneity and ease of operation. Nearly monodisperse liposomes of tunable size may be generated at unprecedented rates, thereby providing microfluidic liposome production suitable for large scale in vivo and preclinical applications.

Embodiments of the present invention also provide for functionalization of liposomes, such as via PEGylation. Conventional chemotherapeutics exhibit poor specificity in reaching tumor tissues. The location and extent of metastatic tumors limit their accessibility, requiring systemic administration which increases drug toxicity. Targeted delivery of nanoparticle-based drugs may be utilized using a variety of tumor-selective ligands including antibodies, aptamers, and peptides conjugated to the nanoparticle surfaces (e.g., see Gu, F. X. et al. (2007) "*Targeted nanoparticles for cancer therapy,*" Nano Today 2:14-21). While these targeting agents can offer high specificity, they are complex and expensive to manufacture using conventional methods, with hydrodynamic radii that can be of the same order of magnitude as the nanoparticles themselves, thus limiting the number of molecules that can be attached for targeted delivery and affecting in vivo behavior.

An alternative small molecule ligand for tumor targeting is folate (Yoshida, T. et al. (2006) "*Induction of cancer cell-specific apoptosis by folate-labeled cationic liposomes,*" J. Controlled Release 111:325-332). Folate receptors are highly-overexpressed in a wide range of cancers, including tumors of the ovary, brain, kidney, lung and breast (Garin-Chesa, P. et al. (1993) "*Trophoblast and ovarian cancer antigen LK26, Sensitivity and specificity in immunopathology and molecular identification as a folate-binding protein,*" Am. J. Pathol. 142:557-567), with up-regulation levels that tend to correlate with tumor stage (Toffoli. G. et al. (1997) "*Overexpression of folate binding protein in ovarian cancers,*" International J. Cancer 74:193-198). Folate binds to these receptors with exceptionally high affinity (Lee. R. J. & Low, P. S. (1994) "*Delivery of Liposomes into cultured KB cells via folate receptor-mediated endocytosis,*" J. Biol. Chem. 269:3198-3204), making it an excellent candidate for targeted delivery. Folate may be readily conjugated with liposomes using polyethyleneglycol (PEG) linkers without affecting its activity (Lee. R. J. & Low, P. S. (1994) "*Delivery of liposomes into cultured KB cells via folate receptor-mediated endocytosis,*" J. Biol. Chem. 269:3198-3204).

Figure 2:
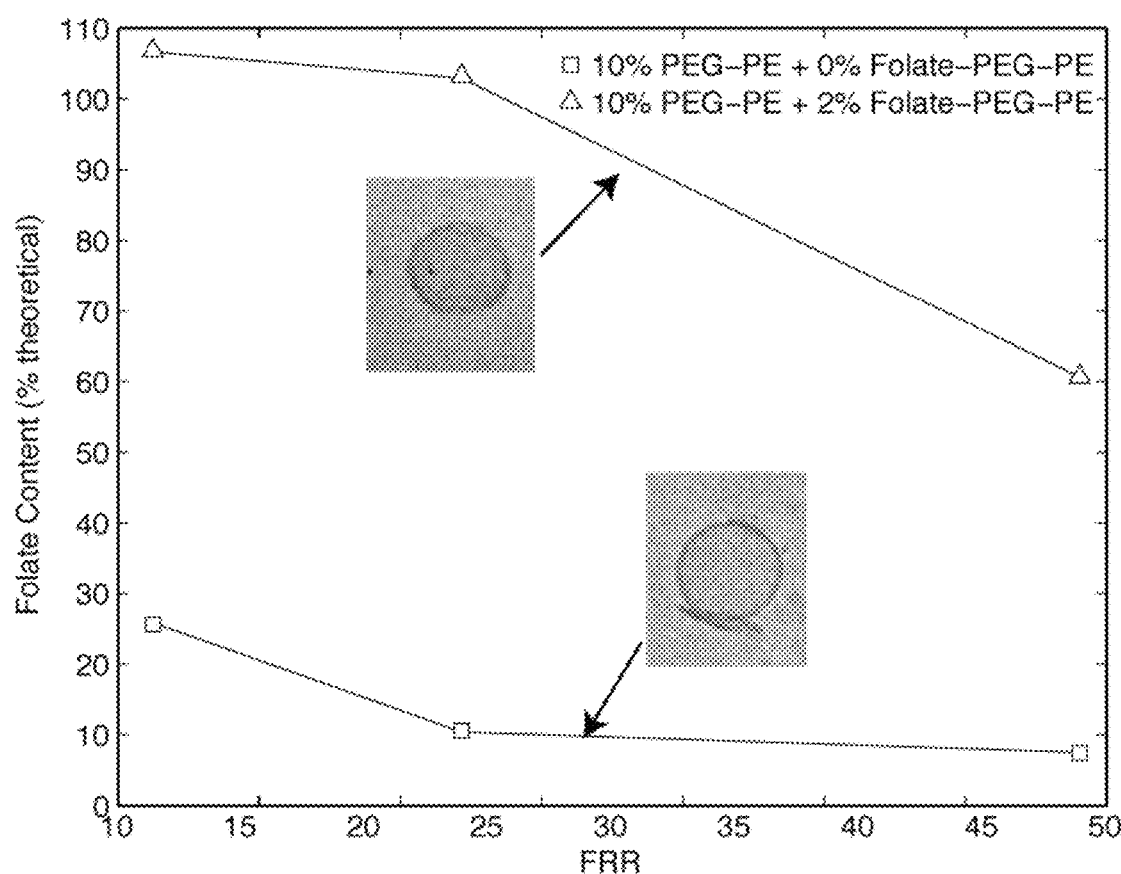
FIG. 2 illustrates graphically measured folate content of liposomes formed with both 10% PEG-PE and 2% folate-PEG-PE added to the lipid mixture prior to flow-focusing. Cryo-TEM images of vesicles formed with and without the added folate are shown inset. Efficient liposome PEGylation was confirmed through separate measurements.

Conventional methods for bulk preparation of folate-functionalized liposomes is normally performed by adding a defined concentration of folate-polyethylene glycol (PEG)-lipid conjugates to an initial lipid solution prior to vortexing and filtration to form the liposomes. In accordance with methods of the present invention, phosphoethanolamine (PE)-containing lipids conjugated with PEGs000 are added to a DMPC lipid mixture. Little variation in liposome diameter was observed when PEG-PE was added to the lipid solution, despite the large size of the PEGs000 molecules. Next, 2 mol % folate-PEG-DSPE (1,2-distearoyl-sn-glycero-3-phosphoethanolamine-N-(folate(polyethylene glycol)$_{2000}$)) is added to the lipid solution. FIG. 2 reveals successful incorporation of folate into the resulting liposomes, as determined by UV/vis absorption measurements from the purified liposomes. Thus, both PEGylated and folate-functionalized liposomes may be successfully produced in the microfluidic platform.

Figure 3:
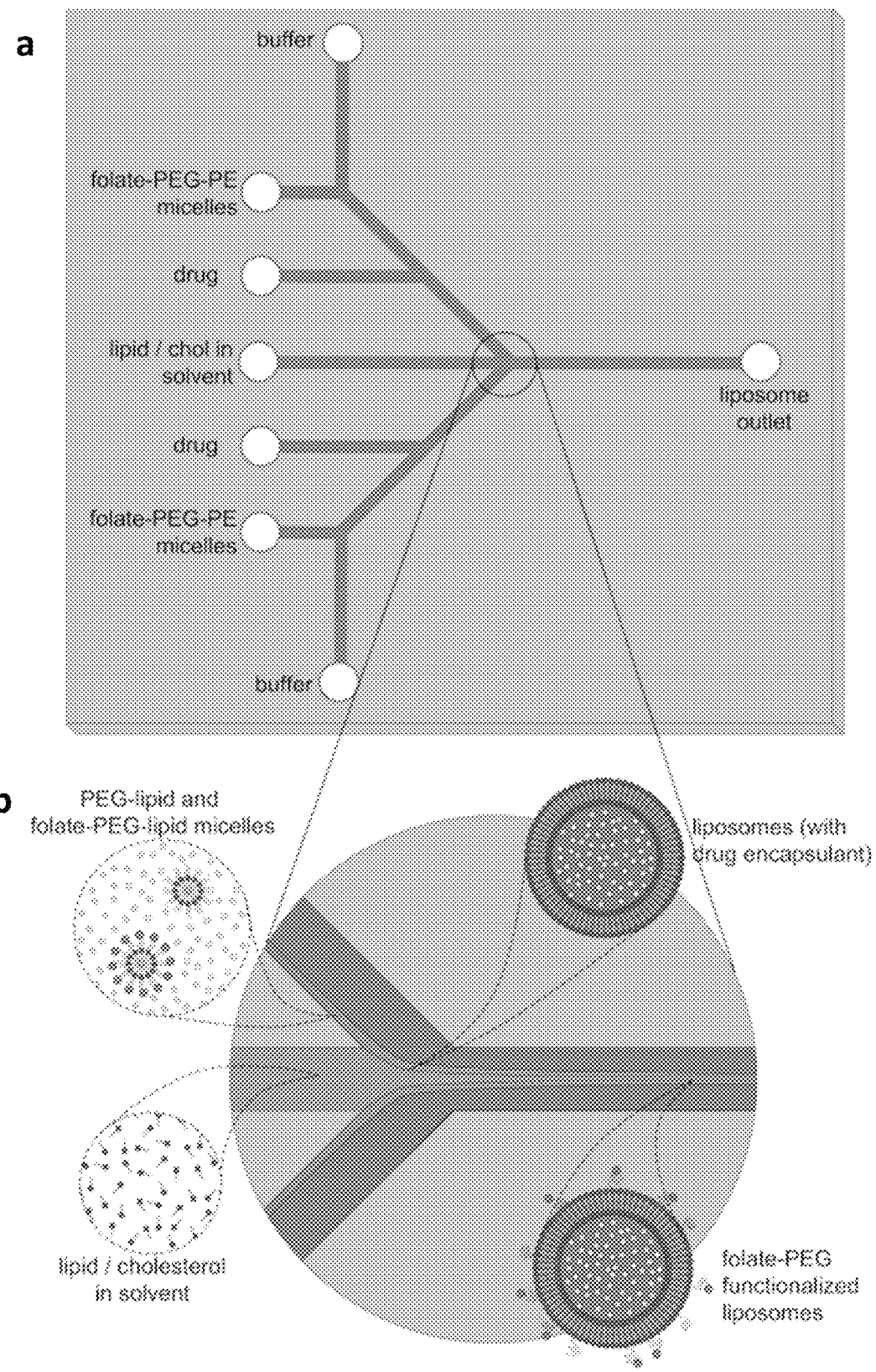
FIG. 3 is a schematic representation of an embodiment of a microfluidic device (FIG. 3, panel a) providing PEG-lipid and folate-PEG-lipid micelle injection for rapid introduction of exogenous ligands into liposomes (hydrophilic drug encapsulation shown). An exploded view of the circled portion of FIG. 3, panel a is shown in FIG. 3, panel b.

While pre-insertion methods offer a simple procedure for producing folate receptor-targeted liposomal drugs, a disadvantage of this approach is that the resulting liposomes present PEG and folate on both inner and outer lipid leaflets. This is a particular concern when forming smaller liposomes, since the large PEG molecules on the inner leaflet limit the internal volume available for drug encapsulation. To avoid this concern, a post-insertion route to folate functionalization may be utilized. As shown in FIG. 3, PEG-lipid and folate-PEG-lipid conjugates are introduced through parallel side channels at concentrations above their critical micelle count, with hydrophilic or lipophilic drug injection channels positioned between the main lipid channel and micelle injection channel. The small drug molecules rapidly diffuse into the liposome formation region and become encapsulated, while the larger micelles with a longer diffusion length scale reach the preformed liposomes downstream of the initial lipid mixing region. In some implementations, a thermoelectric heating element is integrated into the chip to provide local temperature control, and raise the liposomes above the lipid phase transition temperature to encourage the insertion of PEG and folate-PEG into the outer monolayer of the vesicles.

To increase the residence time of interacting micelles and liposomes, a long and wide serpentine outlet channel may be provided. However, due to the short diffusion length scales on the order of several hundred nanometers, equilibrium surface ligand concentrations are rapidly reached within the flow system. Thus, the kinetics of PEG and folate-PEG incorporation may be further optimized by varying channel geometries, flow conditions, and micelle concentrations.

Membrane Dialysis and Active Amphipathic Drug Loading

Following liposome synthesis, the nanoparticles may be purified to remove free lipophilic drug not encapsulated into the vesicles. For conventional bulk liposome preparation, size exclusion chromatography (gel filtration) is the preferred method for vesicle purification (see Holzer, M. et al. (2009) "*Preparative size exclusion chromatography combined with detergent removal as a versatile tool to prepare unilamellar and spherical liposomes of highly uniform size distribution,*" J. Chromatography A 1216:5838-5848). However, implementation of this approach in a continuous flow-through system is not feasible since separate loading and elution buffers must be sequentially applied to the chromatography column. Furthermore, the use of a packed bed of gel chromatography media introduces high hydrodynamic resistance that is incompatible with the flow rates required for liposome formation. Gel filtration also results in vesicle dilution, a significant disadvantage for pharmacy-on-a-chip applications.

In accordance with embodiments of the present invention, the continuous flow system of the present invention utilizes an on-chip membrane dialysis element. The membrane dialysis technique achieves efficient and rapid liposome purification and buffer exchange in a compact flow-through format, and without any vesicle dilution. In some implementations, a nanoporous cellulose membrane is permanently sealed by solvent bonding between two polymer substrates containing microchannels. The ion-permeable membrane allows buffer exchange between the liposome sample flow injected through the top channel and a counterflow buffer injected through the bottom channel in opposition to the liposome sample flow, thereby maximizing average solute gradients.

In addition to providing a simple flow-through method for liposome purification that is directly compatible with the flow-focusing technique, the on-chip membrane dialysis element enables highly efficient and continuous-flow active loading of an agent or drug into the preformed liposomes. Any desired agent or drug suitable for liposomal encapsulation may be utilized, including but not limited to anthracyclines (doxorubicin, daunorubicin, aciacinomycin, etc.), amphotericin, cytarabine, chlorpromazine, and/or amphipathic peptide or protein drugs (with both hydrophobic and hydrophilic groups, which are soluble in water but also traverse the lipid bilayer into the liposome core).

As a result of the buffer exchange, a transmembrane pH gradient is established, so that amphipathic weak acids and bases are actively loaded into preformed vesicles via directed ion exchange. The active loading enables high drug concentrations to be entrapped within the vesicles with excellent long-term stability. In comparison to conventional active loading methods that require hours or days for incubation at elevated temperatures, utilization of the membrane dialysis element in the disclosed systems quickly shift the pH of the liposome buffer and thereafter actively load the liposomes in minutes (e.g., less than 30 minutes, more preferably less than 10 minutes, more preferably less than 5 minutes, more preferably less than 3 minutes). For example, in some implementations, the pH of the liposome buffer is increased by 3 pH units, such as from an initial level of pH ~6 to a shifted level of pH ~9. The high transmembrane pH gradient allows a selected agent (e.g., such as doxorubicin, an amphipathic weak base, pKa 8.3) to be rapidly driven into the aqueous liposome core.

Figure 4:
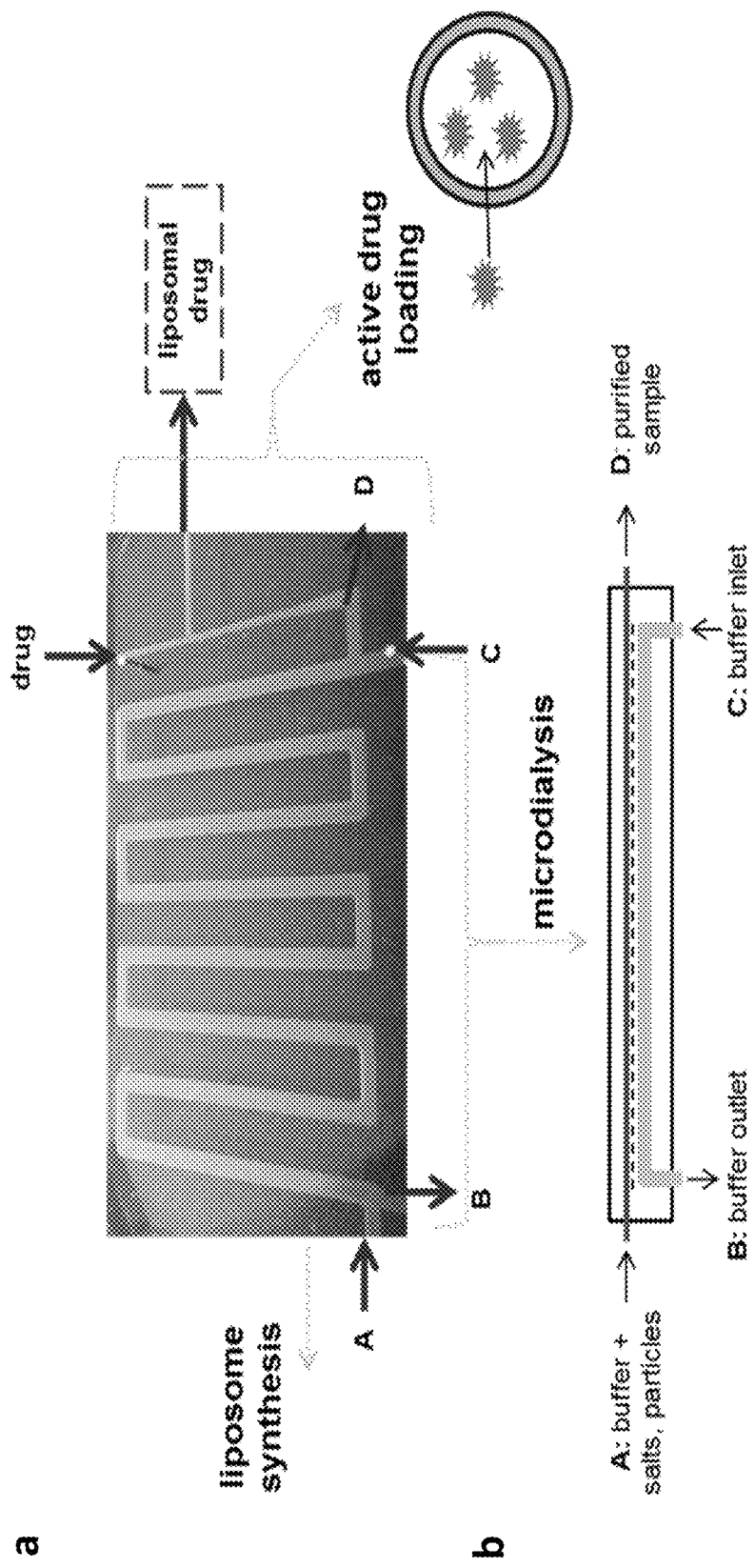
FIG. 4 illustrates schematic representations (FIG. 4, panel a, and FIG. 4, panel b) of a fabricated membrane dialysis chip according to an embodiment enabling rapid liposome purification and buffer exchange for pH adjustment and downstream active drug loading.

An exemplary configuration of a membrane dialysis element of a microfluidic device or chip is illustrated in FIG. 4. Upstream from and in fluid communication with the membrane dialysis element or region is a liposome formation and flow focusing region configured for liposome formation. Downstream from and in fluid communication with the membrane dialysis region is a mixing or loading region configured for receiving an agent (e.g., amphipathic drug) after pH adjustment in the dialysis region. The dialysis region includes an upper or liposome sample flow channel, and a lower or counterflow channel (FIG. 4, panel b).

Figure 5:
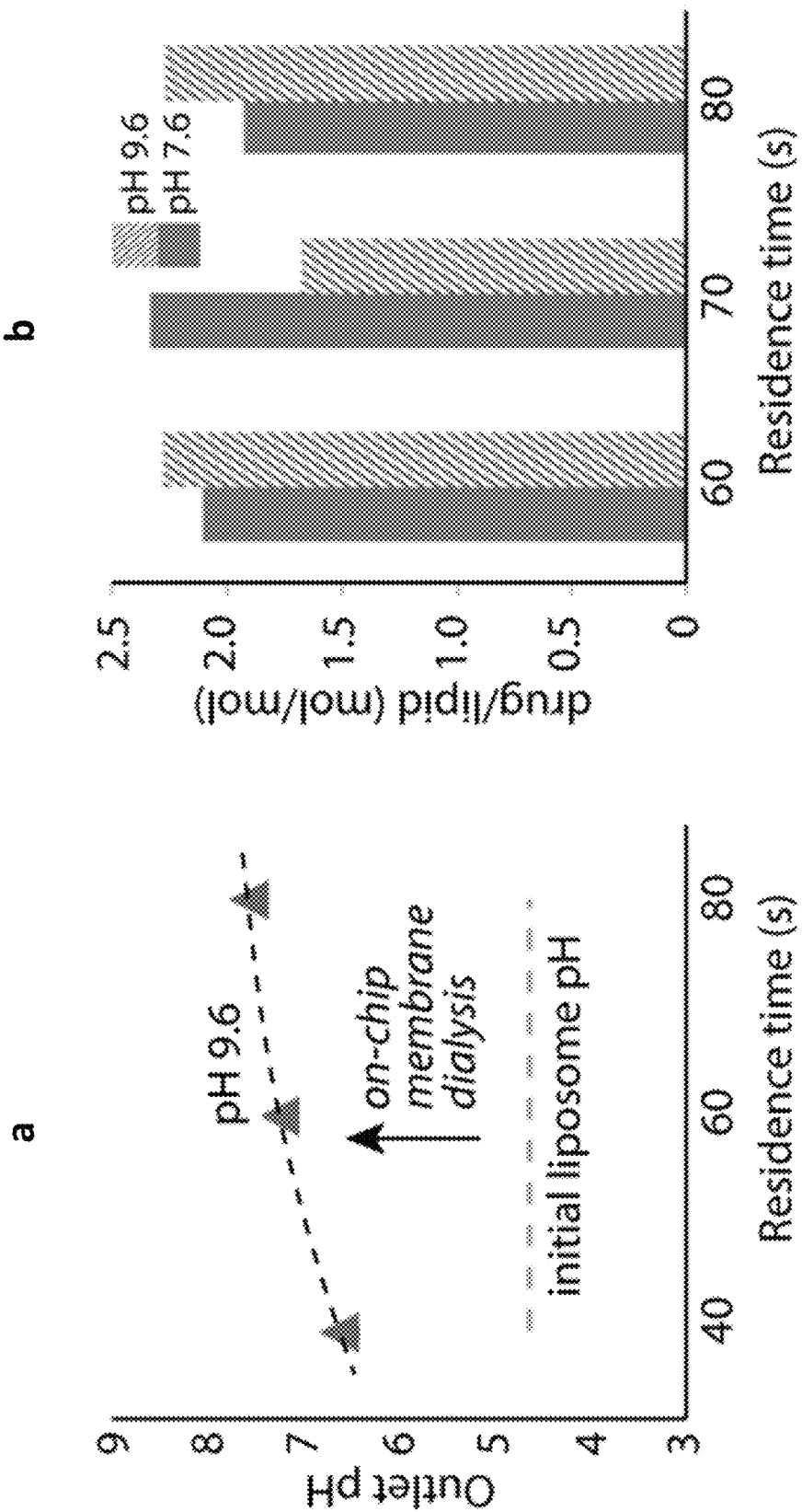
FIG. 5 illustrates graphically exemplary results of on-chip membrane dialysis for pH adjustment of ~3 pH units in under 1 min (FIG. 5, panel a), enabling rapid active loading of AO as an amphiphilic drug analog in a downstream drug/liposome mixing channel (FIG. 5, panel b). Drug:lipid molar ratios greater than 2 were achieved, which is significantly higher than D/L ratios exhibited by conventional bulk processes.

In one implementation, liposomes were formed in a buffer solution at pH 4.6. A counter-flow buffer at pH 9.6 was applied to the counterflow channel. Measurements of pH at the liposome sample flow channel outlet as a function of residence time within the dialysis zone revealed shifts of about 3 pH units in less than 1.5 min (FIG. 5, panel a), sufficient to enable active loading of a desired agent (e.g., acridine orange-HCL (AO; pKa 10.4) as an amphipathic drug analog) immediately after buffer exchange in the dialysis region. Optical absorption measurements revealed entrapment into the microfluidic-synthesized liposomes at drug:lipid molar ratios ranging from 1.6 to 2.3 (FIG. 5, panel b), far exceeding typical D/L ratios of below 0.4 exhibited by conventional bulk active loading methods which require significantly longer processing times (e.g., on the order of several hours or longer).

Because transmembrane pH gradients are unstable, loading efficiency is substantially improved by the disclosed methods by reducing the time between buffer exchange and introduction of the agent or drug (e.g., amphipathic compound). The inherently decreased diffusion lengths in microfluidics enable rapid microdialysis and significantly reduced incubation times for drug loading. To further enhance loading efficiency, a simple passive herringbone mixing zone (e.g., see Du, Y. et al. (2010) "A simplified design of the staggered herringbone micromixer for practical applications," Biomicrofluidics 4:1-13) may be added downstream of the membrane dialysis region to promote effective drug/vesicle interactions. The high loading efficiency of the disclosed techniques obviates the need for post-entrapment purification (e.g., see Fenske, D. B. & Cullis, P. R. (2010) Liposome Technology, Vol. II Entrapment of Drugs and Other Materials into Liposomes), achieving exceptionally high efficiency as compared to conventional bulk processing methods. However, if further purification is desired, a secondary membrane dialysis region may be added to the system following the initial loading region.

Liposome Concentration Enhancement

The resulting drug-loaded liposomes prepared in accordance with disclosed embodiments exhibit clinically-useful drug concentration levels. For doxorubicin, a concentration of 2 mg/mL was targeted, corresponding to a requirement of between $10^{14}$~$10^{15}$ liposomes/mL assuming monodisperse 30-100 nm vesicles with crystallized doxorubicin filling 50% of the aqueous core.

The flow-focusing process operates at typical bulk flow rates of up to ~100 µL/min, with average flow velocities approaching 10 cm/s. While the corresponding Reynolds numbers tend to be small, on the order of Re~$10^{-2}$, the flows are characterized by high Peclet numbers which are well outside the Taylor dispersion regime for even the smallest liposomes of interest. Thus, longitudinal convection dominates vesicle transport, and the stream of liposomes remains tightly focused at the center of the channel over long length scales relative to the lateral channel dimensions. This characteristic of the system is leveraged to improve liposome concentration by reducing the width of the outer sheath flow at the liposome formation site. This enables a proportional reduction in the total volumetric buffer flow rate without impacting liposome formation rate, thereby leading to an equivalent increase in vesicle concentration.

In preliminary studies, flow-focusing elements with 100 µm wide sheath channels yielded vesicle concentrations on the order of $10^{13}$ liposomes/mL, below the target concentration. However, reducing the channel width to 10 µm provided a ten-fold increase in downstream liposome concentration to $10^{14}$ liposomes/mL. In preliminary studies, experiments were performed using lipid concentrations more than an order of magnitude below critical micelle concentration limits, thus indicating that significantly higher concentrations of solvated lipids may be used in the flow-focusing process. In further studies, the final liposome concentration was increased by another order of magnitude to $10^{15}$ liposomes/mL by modifying the flow-focusing geometry while also using higher initial lipid concentrations.

Process Scale-Up

Whether targeted for point-of-care application or industrial drug production, the disclosed pharmacy-on-a-chip systems and methods demonstrate the ability to generate sufficient quantities of drug-laden nanoliposomes for clinical use. For the case of liposomal doxorubicinm, a single 50 mg dose requires ~$10^{15}$ liposomes. Using prior flow-focusing geometry and flow conditions, typical liposome production rates are on the order of $10^{12}$ liposomes/min. Thus, such conventional methods would require $10^3$ minutes (about 16 hours) to produce sufficient drug-loaded liposomes for a single drug dose.

Figure 6:
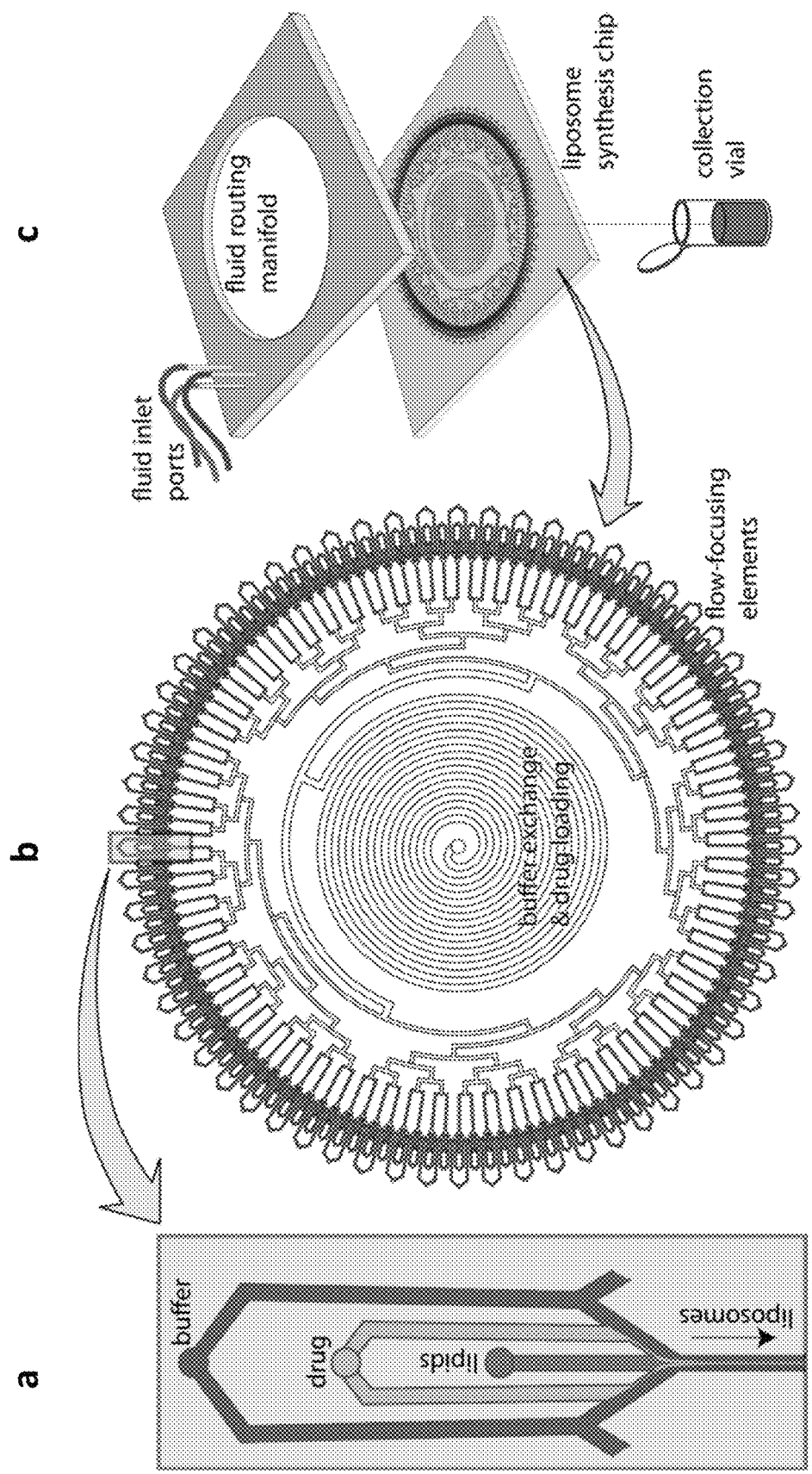
FIG. 6 illustrates schematic representations of a high-throughput nanoliposome drug synthesis chip according to an embodiment of the present invention, comprising a radial array (FIG. 6, panel b) of 128 flow-focusing elements (FIG. 6, panel a). The synthesis chip includes a spiral element supporting buffer exchange, active drug loading, and purification downstream of the parallel liposome formation zones. A fluid routing manifold containing flow splitters is aligned to the flow-focusing chip to connect fluid input lines to the array elements, and a single liposome output port delivers purified liposomal drugs to a collection vial (FIG. 6, panel c).

In order to generate sufficient quantities of liposomes for clinical applications, throughput may be increased by over two orders of magnitude via the parallel operation of array elements. An exemplary high-throughput nanoliposome drug synthesis chip in accordance with an embodiment of the present invention is shown in FIG. 6. The microfluidic chip contains a radial array of 128 individual flow-focusing elements, with inlets connected to a set of single fluid ports through flow splitter networks. Two of the flow splitters, feeding the lipid and lipophilic drug inlets, are fabricated in an upper routing manifold and connected to the flow-focusing array through vertical feedthroughs, while a third flow splitter feeding the buffer inlets is fabricated in the same substrate as the flow-focusing array. In some implementations, all flow splitters and flow-focusing elements are integrated in a single substrate, using a thermoplastic fabrication process that employs a dry film photoresist molding template that can create up to 8 individual fluidic layers with photolithographically-patterned vertical passages for multilayer interconnection. Flow-focusing channel dimensions may be selected to support vesicle concentrations on the order of $10^{14}$-$10^{15}$ liposomes/mL. The outlets of the parallel flow-focusing elements are coupled with a downstream spiral channel supporting sequential buffer exchange to introduce ammonium salt surrounding the vesicles, followed by active drug loading driven by the resulting transmembrane pH gradient, and (if desired) a secondary dialysis region to remove any remaining free amphipathic drug (or other agent) and yield ultra-purified drug-laden liposomes suspended in PBS buffer suitable for in vivo use.

Parallel operation of the array elements allows the time scale for single dose preparation to be reduced to less than 1 hour, preferably less than 30 minutes, more preferably less than 10 minutes, including vesicle formation, membrane functionalization, lipophilic drug loading, purification, buffer exchange, and active loading of amphipathic drug. Throughput may be further increased to industrial-scale preparation levels by operating multiple synthesis chips in tandem.

Having described features and embodiments of the present invention, the same will be further understood through reference to the following additional examples and discussion, which are provided by way of further illustration and are not intended to be limiting of the present invention.

Device Fabrication

Microchannels were fabricated in polydimethylsiloxane (PDMS) substrates by soft lithography techniques using dry film photoresist molds (Stephan, K. et al. (2007) "*Fast prototyping using a dry film photoresist: microfabrication of soft-lithography masters for microfluidic structures,*" J. Micromech. Microeng., 17:N69-N74) produced in a multilayer lamination process. Dry film photoresist (Riston MM115i, DuPont, Research Triangle Park, N.C.) was laminated onto a clean glass slide at 110° C. using a feed rate of 0.02 m s$^{-1}$ and placed on a hot plate at 110° C. for 20 min to promote adhesion. The substrate was patterned by contact photolithography using a UV flood exposure instrument (PRX-1000; Tamarack Scientific Co., Corona, Calif.) at a dose of 72 mJ cm$^{-2}$ for a single layer of photoresist. Multiple photoresist layers were processed sequentially using this approach, with a 1.2× increase in UV dose per layer. Each layer of the dry film photoresist is approximately 37 μm, as measured by stylus profilometry. Following UV exposure, the multilayer substrate was developed using a 1 wt % sodium carbonate solution. The resulting molds feature three regions with three different channel heights (FIG. 7, panel a and panel b). Specifically, the flow focusing and liposome stabilization region was 30 μm wide and 112 μm deep, the buffer exchange region was 1.2 mm wide and 37 μm deep, and the drug loading and mixing region was 30 μm wide and 77 μm deep. Buffer counterflow channels were 1.2 mm wide and 37 μm deep.

The dry film photoresist molds were next used to create microchannels in PDMS. Two separate molds were used to form an upper substrate containing flow focusing, buffer exchange, and drug loading channels, and a lower substrate containing a buffer counterflow channel to assist in microdialysis. The molds were placed in plastic petri dishes and a 10:1 (w:w) mixture of pre-polymer PDMS elastomer and curing agent (Sylgard 184, Dow Corning Corp. Midland, Mich.) was poured on top. Vacuum was applied to remove air bubbles, and the petri dish was placed in a convection oven at 80° C. for 4 h to ensure complete curing of the PDMS. The PDMS substrates were removed from the molds and sectioned using a fresh scalpel. Holes for inlet and outlet interfacing were made using a microbore biopsy punch (Harris Uni-Core, Ted Pella, Inc., Redding, Calif.). All PDMS surfaces were cleaned with isopropanol and DI water.

Figure 8:
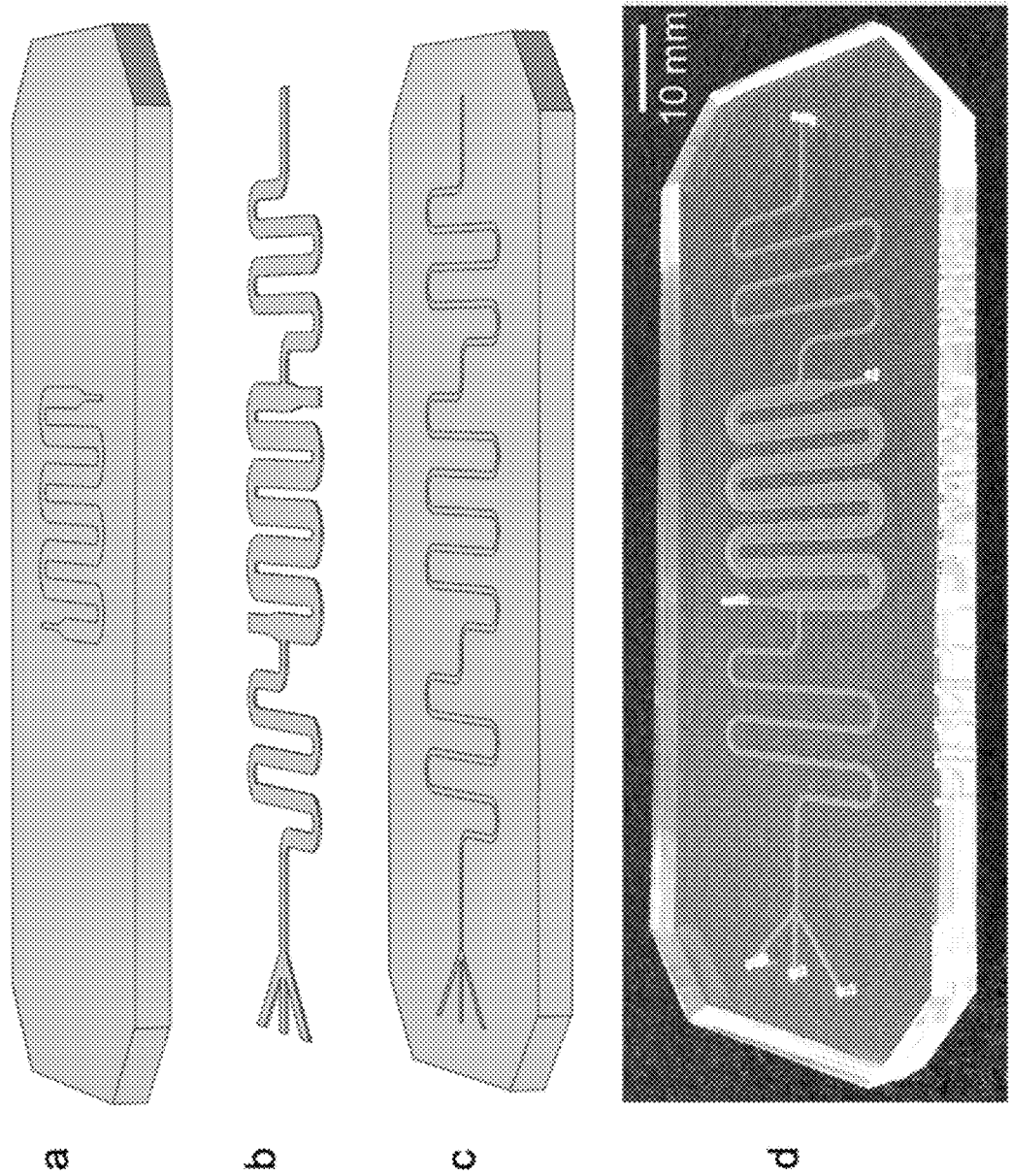
FIG. 8 illustrates schematic representations of components of a PDMS/cellulose hybrid microfluidic device in accordance with embodiments of the present invention, with a channel for buffer counterflow (FIG. 8, panel a), patterned nanoporous regenerated cellulose dialysis membrane (FIG. 8, panel b), and sample channel for liposome synthesis, buffer exchange, and remote drug loading (FIG. 8, panel c). A photograph of an exemplary fabricated device is shown in FIG. 8, panel d.

To form the microdialysis elements, (12 to 14) kDa molecular weight (Mw) cutoff regenerated cellulose (RC) membranes (Spectra/Por 4, Spectrum Laboratories Inc., Rancho Dominguez, Calif.) were placed between the upper and lower PDMS substrates. The membranes were selected to ensure that the nominal pore size (<4 nm) was below the minimum liposome size but large enough to allow all individual chemical species and buffer salts to transport efficiently through the membrane. The RC membranes were cut into patterns similar to the microchannel geometries using an automated craft cutter (Cameo Digital Craft Cutting Tool, Silhouette America, Inc., Orem, Utah), allowing space between adjacent channels for direct PDMS-PDMS contact in these regions. The patterned membranes were flattened using a hydraulic hot press (Carver, Wabash, Ind.) at 0.7 MPa for 10 min at 110° C. prior to chip integration. To enhance sealing between the PDMS substrates, a 10:1 (w:w) mixture of pre-polymer PDMS elastomer and curing agent was poured over a glass slide and spin coated at 3500 rpm for 60 s. The bottom piece of PDMS containing the counterflow channels was stamped onto the thin layer of PDMS, which served as a sealing agent for the microchannels. The patterned RC membrane was aligned with the microchannels on the top piece of PDMS containing the flow focusing, dialysis, and drug loading regions. The two substrates were aligned and pressed together by hand, then placed in a convection oven at 80° C. overnight to cure the intermediate PDMS bonding layer. A schematic of an exploded view of the device components is shown in FIG. 8, panel a, panel b, and panel c, and a photograph of the actual device is shown in FIG. 8, panel d.

Lipid Film and Buffer Preparation

Dimyristoylphosphatidylcholine (DMPC), cholesterol, and dipalmitoylphosphatidylethanolamine-PEG 2000 (PEG2000-PE) (Avanti Polar Lipids Inc., Alabaster, Ala.) were combined in chloroform (Mallinckrodt Baker Inc., Phillipsburg, N.J.) at a molar ratio of 55:35:10. The lipid mixture was prepared in a glass scintillation vial then stored in a vacuum desiccator for at least 24 h for complete solvent removal. The desiccated lipid mixture was re-dissolved in anhydrous ethanol (Sigma Aldrich, St. Louis, Mo.) for a total lipid concentration of either 40 mmol $L^{-1}$ or 20 mmol $L^{-1}$, as noted.

Ammonium sulfate (250 mmol $L^{-1}$, adjusted to pH 4.6) and isosmotic 4-(2-hydroxyethyl)-1-piperazineethanesulfonic acid (HEPES) (10 mmol L–1 with 140 mmol L–1 sodium chloride, adjusted to pH 7.6) were prepared for microdialysis and remote loading experiments (both from Sigma-Aldrich). In some cases, trisodium 8-hydroxypyrene-1,3,6-trisulfonate (pyranine) (Invitrogen, Carlsbad, Calif.) was added to the buffers for pH measurements (1 μmol L–1). Acridine Orange hydrochloride (AO) at an initial concentration of 10 mg $mL^{-1}$ (Sigma-Aldrich) was further diluted in deionized water as noted and used for remote loading experiments. Doxorubicin hydrochloride (DOX) (Sigma-Aldrich) was diluted to 1.4 mg $mL^{-1}$ for in-line synthesis and remote loading experiments. All solvents and buffers were passed through 0.22 μm filters (Millipore Corp., New Bedford, Mass.) before being introduced to the microfluidic device.

Numerical Simulation of Ion Exchange Via Microdialysis

Exchange of ammonium sulfate ions during microdialysis was investigated via numerical simulations with a two-dimensional model using COMSOL Multiphysics 4.1 (COMSOL, Inc., Burlington, Mass.). The Transport of Diluted Species (chds) physics interface was applied for the simulation to depict the concentration profiles of the ammonium sulfate salt within the microchannels. Microchannel dimensions from the actual devices fabricated and RC membranes were used to build the model, as well as the known value of the diffusion coefficient of ammonium sulfate in water at room temperature ($D=8.0 \times 10^{-6}$ $cm^2$ $s^{-1}$).

Buffer Exchange and Remote Drug Loading

Microfluidic devices comprising only the 27 cm long buffer exchange zone (sample channel and buffer counterflow channel) were first used to characterize performance of the microdialysis element for rapid ion exchange and remote drug loading. To evaluate buffer exchange, ammonium sulfate (pH 4.6) was injected into the sample inlet, and isosmotic HEPES (pH 7.6 or pH 9.6) was injected into the buffer counterflow inlet with the resulting sample collected for analysis. Sample and counterflow flow velocities were kept equal to one another, and varied from 0.3 cm $s^{-1}$ to 0.6 cm $s^{-1}$ (approximately 7 μL $min^{-1}$ to 14 μL $min^{-1}$, respectively). Pyranine was used as a pH-sensitive molecular probe to determine the pH of the sample and counterflow buffer eluents. Fluorescence intensity maxima of pyranine at 400 nm and 450 nm is strongly dependent on hydrogen ion concentration, and thus measuring the ratio of the 510 nm fluorescence signal at these excitation wavelengths allows solution pH to be determined (Kano, K. & Fendler, J. H. (1978) "*Pyranine as a sensitive pH probe for liposome interiors and surfaces. pH gradients across phospholipid vesicles*" Biochim. Biophys. Acta, 509(2):289-299). Off-chip samples as well as standard curves for calibration over the range from pH 3 to pH 12 were measured using a SpectraMax plate reader (Molecular Devices, Sunnyvale, Calif.).

To analyze AO concentrations, liposome samples were collected following AO loading and placed into 7 kDa Mw cutoff dialysis units (Slide-A-Lyzer MINI; Pierce, Rockford, Ill.) with isosmotic HEPES as the exchange buffer. The samples were dialyzed for a total of 4 h with 3 buffer exchanges to ensure complete purification of free AO. Absorbance measurements of the purified samples as well as a serial dilution of AO in buffer at $\lambda_{max}=495$ nm were taken using a plate reader (SpectraMax; Molecular Devices, Sunnyvale, Calif.) to determine encapsulated AO concentration. The drug-to-lipid ratio of each resultant sample was obtained through these absorbance measurements together with theoretical final lipid concentration, as determined by the initial lipid concentration and given flow rate ratio. The estimate for the final lipid concentration was based on the assumption that all lipids were incorporated into vesicles in the final solution. In practice, some portion of these lipids may be excluded from the liposomes and remain in solution as small micelles or aggregates, and thus the calculated D/L values reflect conservative estimates for this parameter.

To assess the remote drug loading process following buffer exchange, liposomes were first prepared in a separate microfluidic chip by hydrodynamic flow focusing. Briefly, hybrid PDMS-glass devices with 50 μm wide and 300 μm deep microchannels were fabricated, and lipid-ethanol mixture (40 mmol $L^{-1}$) was injected into the microfluidic device between two sheath flows of ammonium sulfate buffer (250 mmol $L^{-1}$, pH 4.6). The flow rate ratio, defined as the ratio of the volumetric flow rate of the aqueous buffer to the flow rate of lipids in ethanol, was set to 20. Total linear flow velocity was set to 12.5 cm $s^{-1}$, or an equivalent volumetric flow rate of 112 μL $min^{-1}$. To reduce vesicle size, the microfluidic device was operated on a hot plate at 50° C. throughout synthesis (Zook, J. M. & Vreeland, W. N. (2010) "*Effects of temperatures, acyl chain length, and flow-rate ratio on liposome formation and size in a microfluidic hydrodynamic focusing device,*" Soft Matter, 6:1352-1360). The resulting liposome size distributions (volume weighted) were characterized via dynamic light scattering (Nano ZSP, Malvern Instruments Ltd., UK). Volume weighted distributions, i.e. sizes weighted proportionally to their volume, were chosen to represent sample diameters to avoid signal seen by any large aggregates or dust present within the sample.

The liposomes in ammonium sulfate buffer were injected into the inlet of the microdialysis chip with isosmotic HEPES (pH 7.6) as the buffer counterflow. AO, an amphipathic dye used as a drug analog for remote loading experiments, was introduced through a secondary channel immediately after buffer exchange at a ratio of 1:3 relative to the sample channel volumetric flow rate. Liposome sample velocity was varied from 0.17 cm $s^{-1}$ to 0.44 cm $s^{-1}$ with AO concentration constant at 0.25 mg $mL^{-1}$ to investigate the effect of flow velocity and residence time on loading concentration and efficiency. AO concentration was varied from 0.125 mg $mL^{-1}$ to 2.5 mg $mL^{-1}$ (corresponding to D/L values of 0.22 to 4.35, respectively) with the flow velocity held constant at 0.26 cm $s^{-1}$ to demonstrate the effect of AO concentration on loading efficiency and maximum D/L levels in the resulting drug-laden liposomes.

In-Line Liposome Synthesis and Drug Loading

An integrated device containing a liposome formation region, microdialysis buffer-exchange region, and drug-loading region was used to evaluate the overall process. For liposome formation, lipid-ethanol solution (20 mmol $L^{-1}$) was injected into the flow-focusing element between two sheath flows of aqueous ammonium sulfate buffer (250 mmol L$^{-1}$, pH 4.6). The total volumetric flow rate was 6 µL min$^{-1}$ (corresponding to 0.26 cm s$^{-1}$ in the dialysis region) with a flow rate ratio of 10. The microdialysis counterflow buffer flow rate was matched to the primary flow rate to minimize the average pressure gradient across the RC membrane. The drug:liposome sample flow rate ratio was 1:3 for all experiments. For drug loading, both AO (0.5 mg mL$^{-1}$ and 1.0 mg mL$^{-1}$, corresponding to initial D/L values of 0.22 and 0.44, respectively) and DOX (1.4 mg mL$^{-1}$, corresponding to an initial D/L of 0.44) were investigated. Multiple samples were collected (n=3) for each test.

To ensure that free drug remaining in the collection buffer following remote loading did not affect concentration measurements, collected liposome samples were further dialyzed off chip with isosmotic HEPES as the exchange buffer. Two aliquots of each sample, one off-chip and one two-fold dilution, were dialyzed for 4 h with 3 buffer exchanges for complete purification of free DOX or AO. Absorbance measurements of the purified samples as well as a serial dilution of DOX or AO in buffer were compared with standard curves to determine final encapsulated drug concentration. Size distributions of collected samples were further characterized by dynamic light scattering (Nano ZSP, Malvern Instruments).

Discussion

Figure 9:
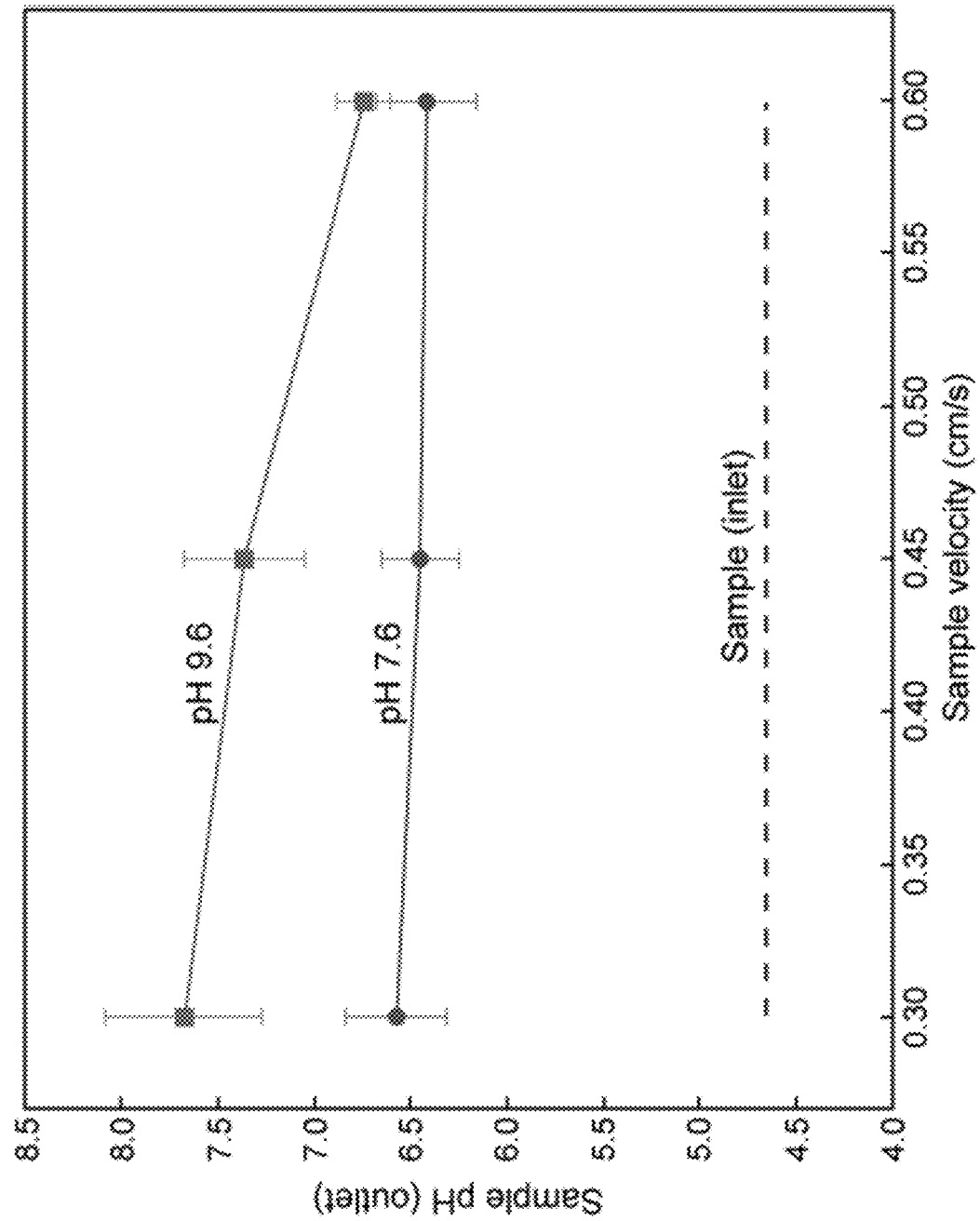
FIG. 9 is a graphical representation of exemplary data for on-chip microfluidic buffer exchange via membrane dialysis at various counterflow pH and flow velocities. Residence times varied from 40 s to 80 s, resulting in a ΔpH of 1.7 to 3.0. Total flow rates varied from approximately 7 µL min$^{-1}$ to 14 µL min$^{-1}$ (with average linear velocities from 0.6 cm s$^{-1}$ to 0.3 cm s$^{-1}$, respectively).

Counterflow microdialysis provides an efficient method for on-chip buffer exchange, enabling rapid transport and removal of free ions from the sample buffer while preventing loss of nanoparticles during the exchange of small ions across the microdialysis membrane. To evaluate performance of this approach for establishing transmembrane ion gradients in a rapid flow-through format, a PDMS-RC device consisting solely of the counterflow microdialysis zone was fabricated. Characterization of the device for ion exchange was first evaluated by introducing buffers at different pH values through the sample and counterflow ports. Rapid pH change of the sample flow was observed, as revealed through pyranine fluorescence measurements, with the level of pH shift roughly proportional to residence time as determined by the applied flow rate (FIG. 9). As expected, microdialysis performance was also found to be dependent on counterflow buffer pH, with a greater difference in pH between the sample and counterflow buffers resulting in a larger pH shift at the sample buffer outlet. For the experimental conditions tested, a maximum shift of 3 pH units was achieved using pH 9.6 counterflow buffer and a residence time within the dialysis channel of 83 s. This is substantially faster than bulk scale microdialysis, which can take hours for complete buffer exchange to occur.

A prediction for the transport of ammonium sulfate ions during microdialysis can be made by considering simple diffusion within the system. Using a value of $8.0 \times 10^{-6}$ cm$^2$ s$^{-1}$ for the diffusion coefficient of ammonium sulfate in water at room temperature (Leaist, D. G. & Hao, L. (1992) J. Solution Chem., 21:345-350), the diffusion time for a characteristic length scale given by the microchannel height (37 µm) is 1.71 s, significantly smaller than the residence times explored in this work which ranged from 42 s to 83 s. To verify this prediction, ammonium ion transport was evaluated through a two dimensional numerical simulation of the device. The model indicates that the extra-liposomal ammonium ion content is reduced by more than 100 times from the initial concentration sequestered within the vesicles (FIG. 10, panel a, and panel b), a desired condition for effective remote loading.

A potential issue with the continuous flow microdialysis element is potential alteration of liposome size during dialysis. Prior to buffer exchange, the microfluidic-synthesized liposomes were found to be 80.8 nm in diameter with a very low polydispersity index (PDI) of 0.049. Size distributions measured before and after on-chip microdialysis revealed only a slight increase in mean vesicle size to 91.5 nm, confirming that the on-chip counterflow microdialysis element did not significantly affect the liposome size. Buffer counterflow eluent was also collected and examined via light scattering. No detectable signal was observed, revealing that intact liposomes do not escape the membrane and enter the counterflow during microdialysis.

As noted above, anthracyclines represent an important class of drugs for liposomal encapsulation. Received by nearly every patient undergoing systemic cancer chemotherapy, anthracyclines are among the most utilized and effective antitumor drugs developed to date (Hortobágyi, G. N. (1997) "*Anthracyclines in the treatment of cancer. An overview.* Drugs, 54:1-7). Liposomal forms of anthracyclines can provide increased efficacy with significantly reduced toxicity (Minotti, G. et al. (2004) "*Anthracyclines: molecular advances and pharmacologic developments in antitumor activity and cardiotoxicity.*" Pharmacol. Rev., 56(2):185-229) enhancing the overall clinical value of the drugs (Allen, T. M. & Martin, F. J. (2004) "*Advantages of liposomal delivery systems for anthracyclines,*" Semin. Oncol. 31:5-15). Liposomal encapsulation of the anthracycline doxorubicin (DOX) has proven particularly successful for treatment of a range of cancers (Barenholz, Y. C. (2012) "*Doxil®—the first FDA-approved nano-drug: lessons learned.*" J. Controlled Release, 160:117-134). Accordingly, DOX was targeted as a model drug encapsulant to investigate the potential for continuous flow remote drug loading using the disclosed microfluidic process.

Figure 11:
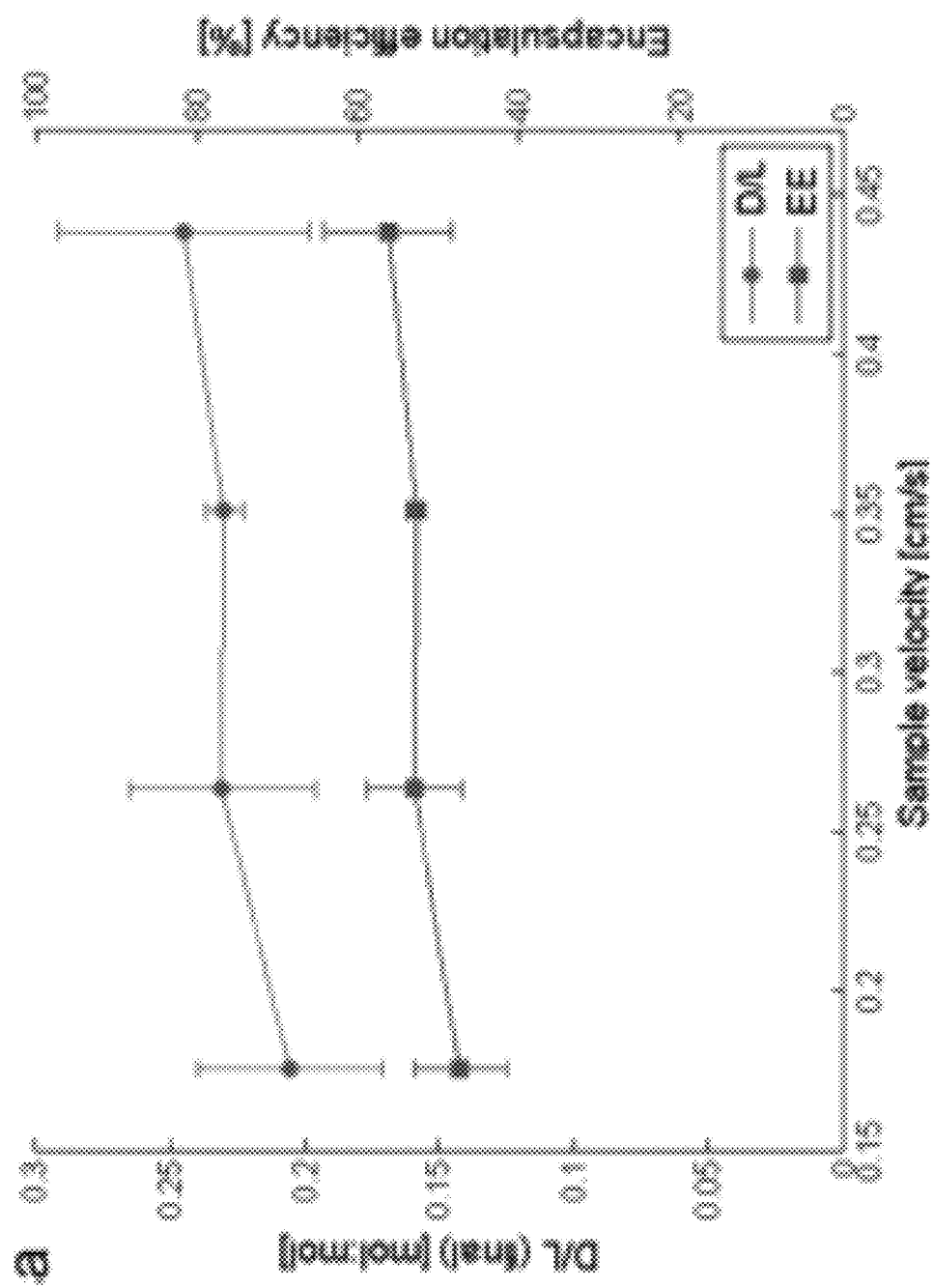
FIG. 11 illustrates graphically the relationships between sample velocity (FIG. 11, panel a) and initial AO concentration (FIG. 11, panel b) on final encapsulated concentration and loading efficiency. Microfluidic-generated liposomes, 80.8 nm in diameter, were formed in a separate chip for this experiment.
Figure 11:
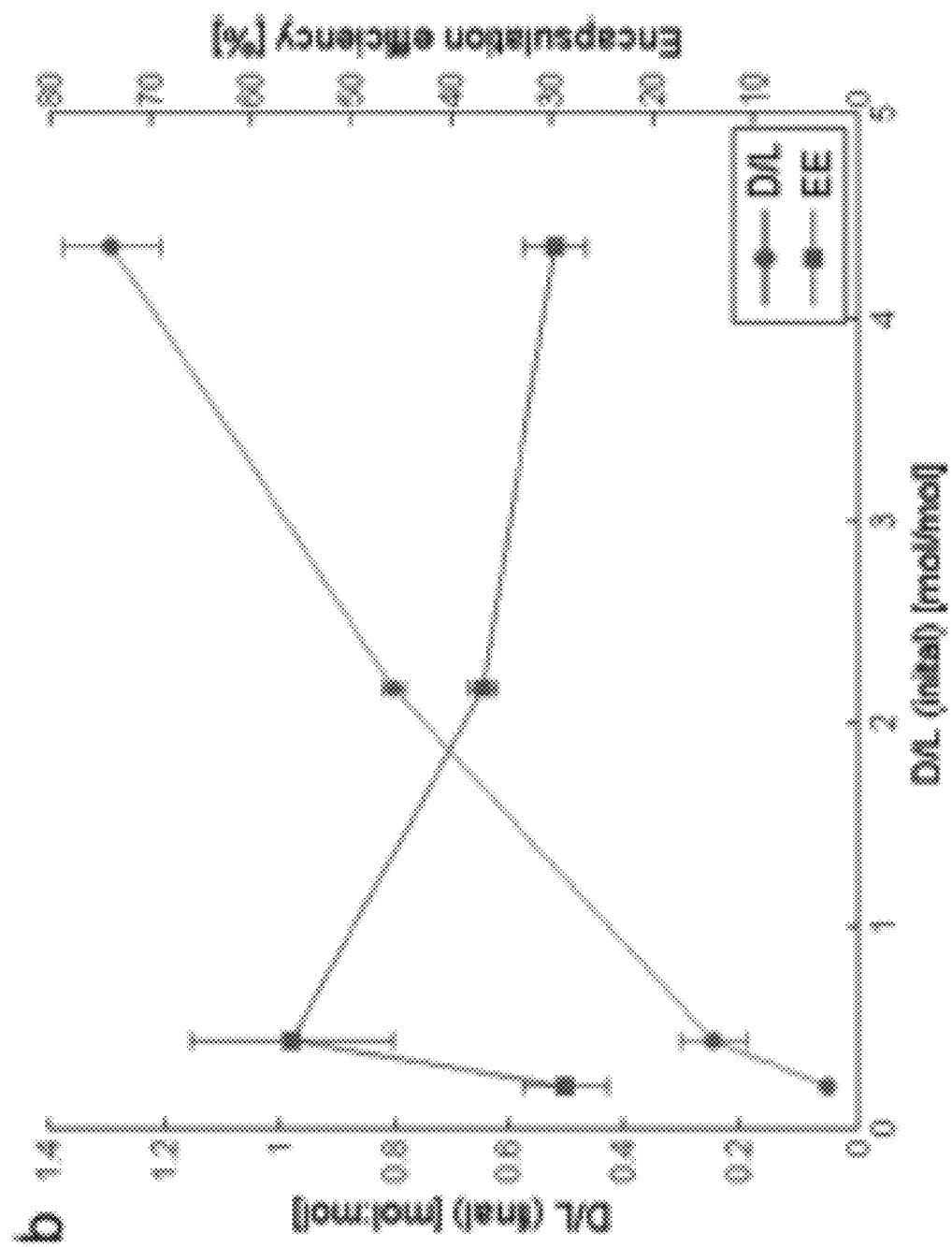

Initial testing was performed using preformed liposomes injected into the counterflow microdialysis chip to form the desired transmembrane ion gradient, followed by on-chip introduction of AO as a suitable analog to DOX. AO is an amphipathic weak base with similar properties to DOX, and is known to behave similarly to DOX during remote loading with ammonium sulfate gradients (Clerc, S. & Barenholz, Y. (1998) "*A quantitative model for using acridine orange as a transmembrane pH gradient probe,*" Anal. Biochem., 259: 104-111; Zucker, D. et al. (2009) "*Liposome drugs loading efficiency: a working model based on loading conditions and drug's physiochemical properties,*" J. Controlled Release, 139:73-80). FIG. 11, panel a presents the measured final D/L and encapsulation efficiency (EE) for AO-loaded liposomes prepared using an initial D/L of 0.44 when varying the sample velocity from 0.18 cm s$^{-1}$ to 0.45 cm s$^{-1}$, for a total residence time within the mixing channel ranging from 4.25 min to 1.7 min, respectively. While a slight increase in both final D/L and EE was observed with increasing flow rate, overall remote loading using the microfluidic approach exhibited little dependence on flow velocity. In contrast, the initial concentration of drug compound introduced following ion exchange had a substantial effect on the final D/L (FIG. 11, panel b). By increasing the initial D/L level, final D/L values up to 1.3 were achieved. This effect is believed to be due to the significantly decreased diffusion lengths with increasing AO concentration, and thus a greater quantity of AO may be loaded when the initial concentration is higher. Reported D/L values for liposomal anthracyclines produced via conventional bulk-scale remote loading are typically below 0.25 (Drummond, D. C. et al. (1999) "*Optimizing liposomes for delivery of chemotherapeutic agents to* solid tumors," Pharmacol. Rev., 51:691-743), significantly less than the levels achieved using the disclosed microfluidic process of the present invention.

The higher optimal D/L observed for the microfluidic platform can be explained by the rapid introduction of AO following buffer exchange, together with the use of a high initial D/L and effective on-chip mixing between liposomes and encapsulant for decreased diffusion lengths during drug loading in the presence of a stable and steep ion gradient. Encapsulation efficiency of the resulting liposomes was observed to increase with initial D/L, and then began to diminish for initial D/L values exceeding 2.17. This result is in accordance with studies based on bulk-scale loading based on longer loading periods (hours to days), which suggest EE peaks at an initial D/L of 0.95 and decreases at higher ratios (see Zucker, D. et al. (2009) "*Liposome drugs loading efficiency: a working model based on loading conditions and drug's physiochemical properties,*" J. Controlled Release, 139:73-80). This behavior is due to insufficient intravesicular loading capacity above some limiting D/L level, resulting in a lower EE as drug concentration is further increased. The higher optimal D/L observed for the microfluidic platform is believed to result from the highly efficient formation of a transmembrane ion gradient due to rapid microfluidic buffer exchange, followed by immediate interactions between the vesicles and the amphipathic molecules to be loaded. The steep transmembrane ion gradient achieved through rapid buffer exchange enables higher D/L ratios to be achieved through microfluidic remote loading versus bulk scale processes.

Figure 12:
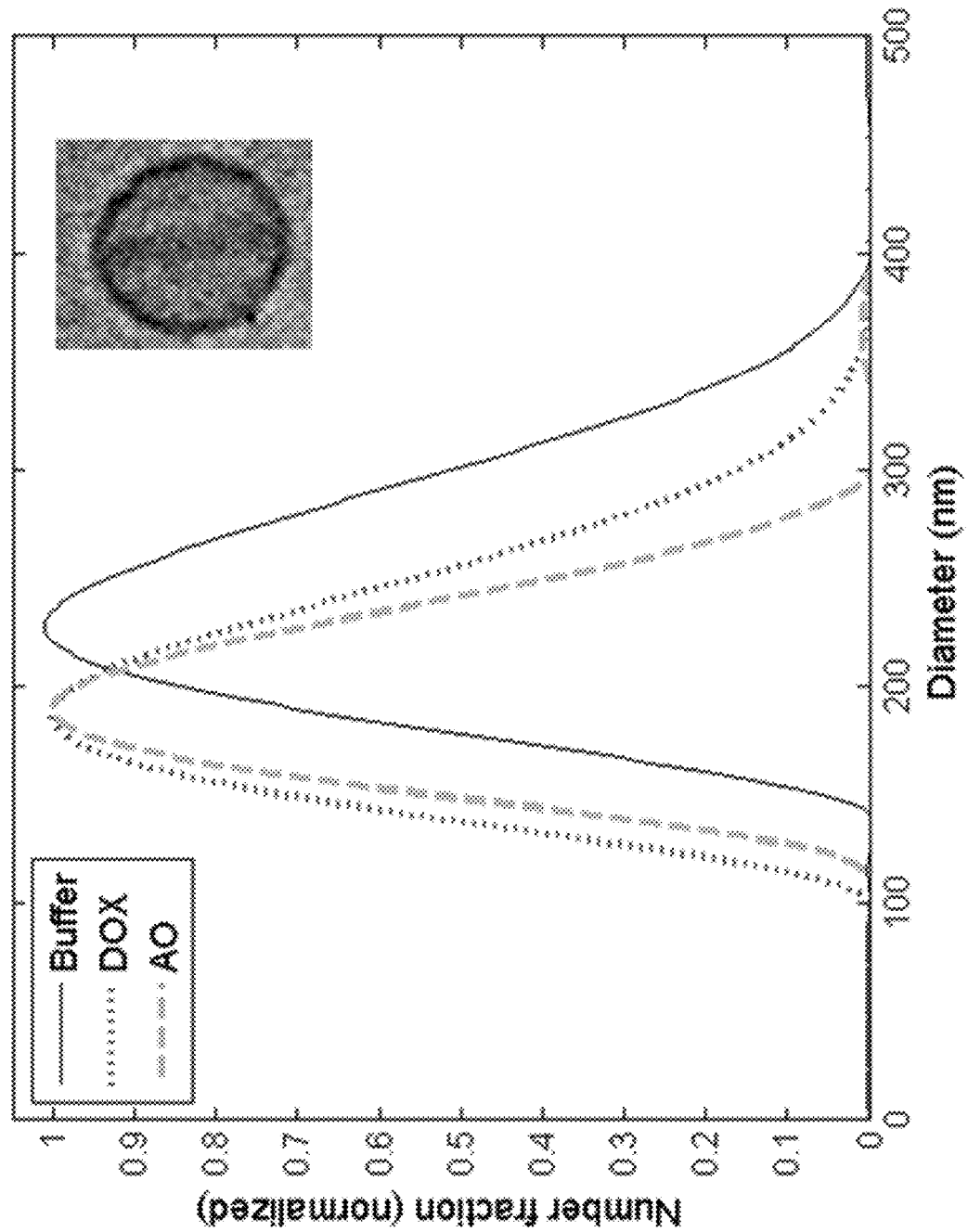
FIG. 12 depicts graphically volume-weighted size distributions from remote loading of DOX and AO into liposomes in-line with synthesis and microdialysis for buffer exchange in comparison to unloaded liposomes (buffer only) generated by the microfluidic device. A cryoTEM image of a DOX-loaded liposome formed in-line with synthesis is shown inset.

After demonstrating buffer exchange, pH adjustment, and remote loading of AO into preformed vesicles using the microfluidic approach, liposome synthesis in-line with microdialysis and remote loading of both AO and DOX was performed using an integrated device combining all of the process steps in a single flow-through chip. The resulting liposomes were first characterized for diameter when AO, DOX or buffer was alternately injected as the drug loading phase (FIG. 12). Under the flow conditions used in these experiments, the resulting liposomes exhibited an average diameter of 225.5 nm±44.8 nm for the case of buffer without amphipathic encapsulant, while a reduction in liposome size to 190.9 nm±43.0 nm for DOX-loaded liposomes and 191.5 nm±33.4 nm for AO-loaded liposomes was observed. The reduction in liposome size of approximately 15% after remote loading may reflect a change in morphology to a characteristic "coffee bean" shape resulting from drug crystallization within the vesicles, leading to altered signals during dynamic light scattering. Confirmation of drug crystallization was verified through cryogenic transmission electron microscopy (cryoTEM) imaging. A cryoTEM image of a DOX-loaded liposome is shown inset in FIG. 12.

Figure 10:
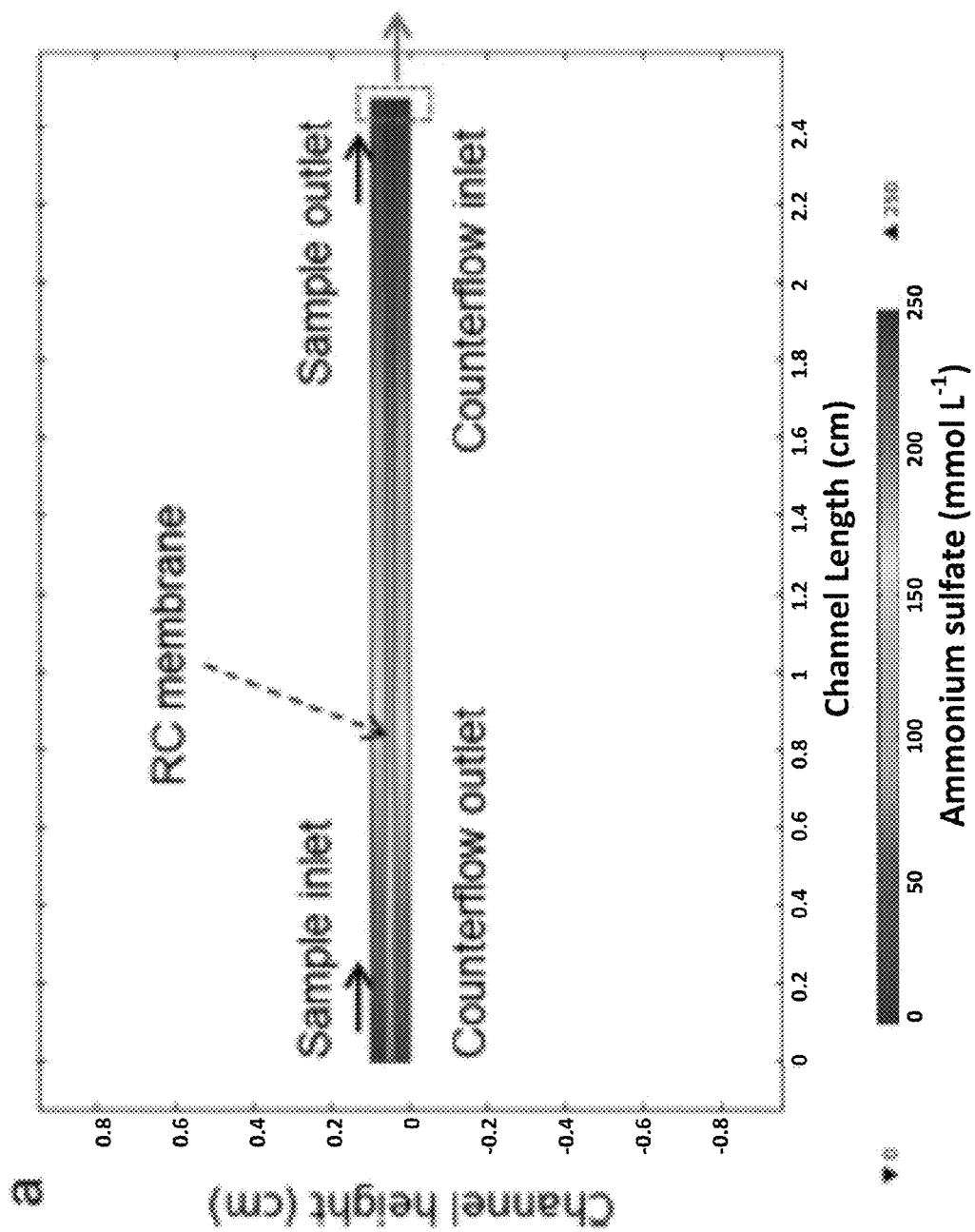
FIG. 10 illustrates graphically a numerical simulation of ammonium sulfate (initial concentration 250 mmol L$^{-1}$) transport in the microfluidic device to verify adequate ion removal.
Figure 10:
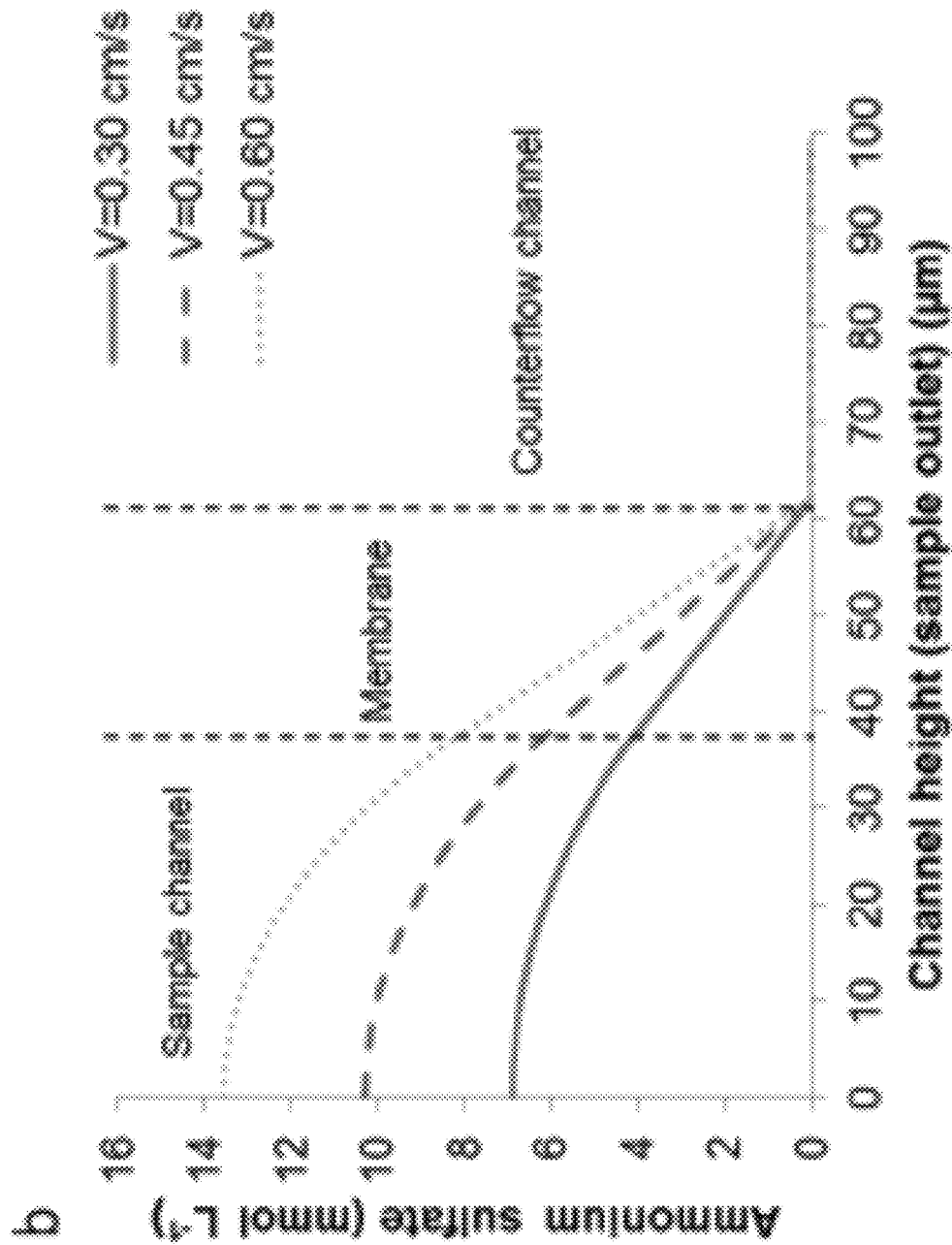

A summary of measured final D/L values following AO and DOX loading within the integrated microfluidic device is presented in Table 1 below. Prior results for the case of AO loading using preformed liposomes generated in a separate chip are also shown for comparison. An initial D/L of 0.44 was selected for DOX, as this ratio was found to maximize loading efficiency in initial experiments using AO (FIG. 10). The DOX loaded liposomes generated by the microfluidic device had a final D/L of 0.32±0.03 (standard deviation), which exceeds the typical D/L of 0.25 or less achieved by conventional bulk remote loading employing overnight incubation. The total on-chip residence time within the microfluidic device was less than 3 min. In addition, initial D/L values of 0.22 and 0.44 were used for testing AO loading, resulting in final D/L values of 0.06±0.01 and 0.32±0.11, respectively.

TABLE 1

Summary of D/L and EE measurements for AO loaded liposomes (preformed liposomes produced in a separate chip) and DOX and AO loaded liposomes (formed in-line with synthesis in a single integrated chip). Similar results were achieved for DOX and AO loading within the integrated device. Slightly higher final D/L and EE values were observed when remote loading was performed in-line with liposome synthesis. The in-line remote loading process achieves D/L levels exceeding typical values of 0.25 or below achieved by day-long bulk incubation, but with only a 3 minute on-chip residence time.

| Loading case | Liposome diameter (nm) | Drug/agent | D/L (initial) | D/L (final) | EE (%) |
|---|---|---|---|---|---|
| Preformed | 80.8 ± 17.9 | AO | 0.22 | 0.05 ± 0.01 | 23.5 ± 4.2 |
|  |  |  | 0.44 | 0.24 ± 0.06 | 55.9 ± 10.0 |
| In-line | 191.5 ± 33.4 | AO | 0.22 | 0.06 ± 0.01 | 26.9 ± 2.2 |
|  |  |  | 0.44 | 0.32 ± 0.11 | 69.8 ± 18.0 |
|  | 190.9 ± 43.0 | DOX | 0.44 | 0.32 ± 0.03 | 71.8 ± 4.2 |

Encapsulation efficiency using the integrated system was also evaluated. Referring to Table 1 above, the DOX-loaded liposomes yielded an EE of approximately 72%, lower than typical values for conventional remote loading which can exceed 99% (Lewrick, F. & Süss, R. (2010) "*Remote loading of anthracyclines into liposomes,*" Methods Mol. Biol., 605:139-145). Lower encapsulation efficiency compared to bulk-scale remote loading is not surprising, since the incubation time is up to 300 times lower within the microfluidic system. If desired, EE may be increased by implementing an additional on-chip region for capturing and recycling drug following initial remote loading (e.g., such as a secondary dialysis region). Optimizing loading conditions eliminates the need for off-chip purification, enabling real-time production of stably encapsulated, highly concentrated liposomal drugs at or near the point of care.

Direct comparison of in-line system performance with the previous results from remote loading using preformed liposomes is hampered by the different sizes of each liposome population. When performing in-line remote loading, fluidic coupling between the upstream liposome formation zone and downstream microdialysis and drug loading zones demands careful design of the channel dimensions, together with appropriate selection of inlet flow rates. Liposome size and polydispersity are both impacted by the buffer:lipid flow rate ratio, overall volumetric flow rate, and microchannel dimensions selected for effective liposome self-assembly during hydrodynamic flow focusing. However, these same parameters also affect microdialysis and remote drug loading performance. While channel dimensions for each functional element in the system can be designed independently, allowing a degree of decoupling between these constraints, conventional microfabrication processes used for device manufacture present some limitations. For example, to avoid sagging of the microdialysis membrane, a maximum channel width of 1.2 mm was used for the buffer exchange zone. Similarly, total volumetric flow rates were minimized to prevent delamination of the hybrid microfluidic device due to excessive internal fluid pressure. As a result of these constraints, liposomes formed using the on-line system were approximately twice the diameter of their preformed counterparts. Although residual pH gradients decrease with decreasing vesicle size due to decreased intravesicular volumes, it has been shown that this effect can be circumvented by including a buffering capacity greater than 300 mmol $L^{-1}$ (Mayer, L. D. et al. (1990) "*Characterization of liposomal systems containing doxorubicin entrapped in response to pH gradient,*" Biochim. Biophys. Acta 1025:143-151). Additionally, given the significantly larger volume of the in-line liposomes, it is notable that both the final D/L and EE values for in-line encapsulation were comparable to the case of preformed liposome loading, with slight increases in both values for the larger liposomes. This further emphasizes the observation that the initial D/L is an important parameter of encapsulation performance during remote loading within the continuous flow microfluidic system.

Further, liposome concentrations achieved by the microfluidic system were typically in the range of $10^{10}$-$10^{12}$ liposomes $mL^{-1}$, depending on experimental parameters including lipid concentration and flow rate ratio. For comparison, reported concentration levels generated by typical bulk production methods range from $10^7$-$10^{12}$ liposomes $mL^{-1}$ (Chen, H. et al. (2010) "*Construction of supported lipid membrane modified piezoelectric biosensor for sensitive assay of cholera toxin based on surface-agglutination of ganglioside-bearing liposomes,*" Anal. Chim. Acta, 657(2): 204-209; Hitchcock, K. E. (2010) "*Ultrasound-enhanced delivery of targeted echogenic liposomes in a novel ex vivo mouse aorta model,*" J. Controlled Release, 144:288-295), indicating that the microfluidic technique is an effective and viable alternative for liposomal drug preparation without requiring additional steps to further concentrate the vesicles following on-chip processing.

Thus, by combining liposome synthesis via microfluidic flow focusing, membrane microdialysis for buffer exchange, and in-line introduction of amphipathic weak bases for remote loading within a single microfluidic device, the conventional multi-step bulk-scale processes requiring hours to days of labor are replaced by the microscale process of the present invention, which requires a total on-chip residence time of less than 10 minutes, and in some embodiments less than 5 minutes (e.g., approximately 3 minutes or less).

By taking advantage of the reduced diffusive length scales characteristic of microscale flows, the microfluidic method implements remote loading as a seamless continuous flow process, thereby simplifying yet increasing the robustness of remote loading in naniloposomal drug production. The further ability to perform integrated liposome formation using hydrodynamic flow focusing prior to formation of a transmembrane ion gradient for remote drug loading allows the entire sequence of steps required for liposomal drug production to be performed as a single in-line and continuous flow process. The microfluidic methods and systems demonstrated herein enable exceptionally high drug loading levels, with D/L values above unity easily achieved, enabling point-of-care production of purified liposomal drug formulations with minimal drug waste.

HAR-MHF Methods and Comparisons

Microfluidic devices enabling high throughput production of liposomal nanoparticles were demonstrated utilizing high aspect ratio microfluidic hydrodynamic flow-focusing (HAR-MHF) methods. HAR-MHF devices featured microchannels having extremely wide channel widths and narrow channel heights. Lipid and buffer microchannels were arranged in multiple layers such that the lipid stream was focused into a thin sheet parallel to the plane of the device, unlike prior MHF methods in which the lipid stream is focused perpendicular to the plane of the device. Microfluidic liposome synthesis for large scale applications (e.g. in vivo experiments, preclinical studies, and point-of-care applications) and at unparalleled production rates was achieved, while retaining the benefits of effective liposome size control (such as demonstrated using MHF) and reduced levels of polydispersity.

HAR-MHF Device Fabrication

Figure 13:
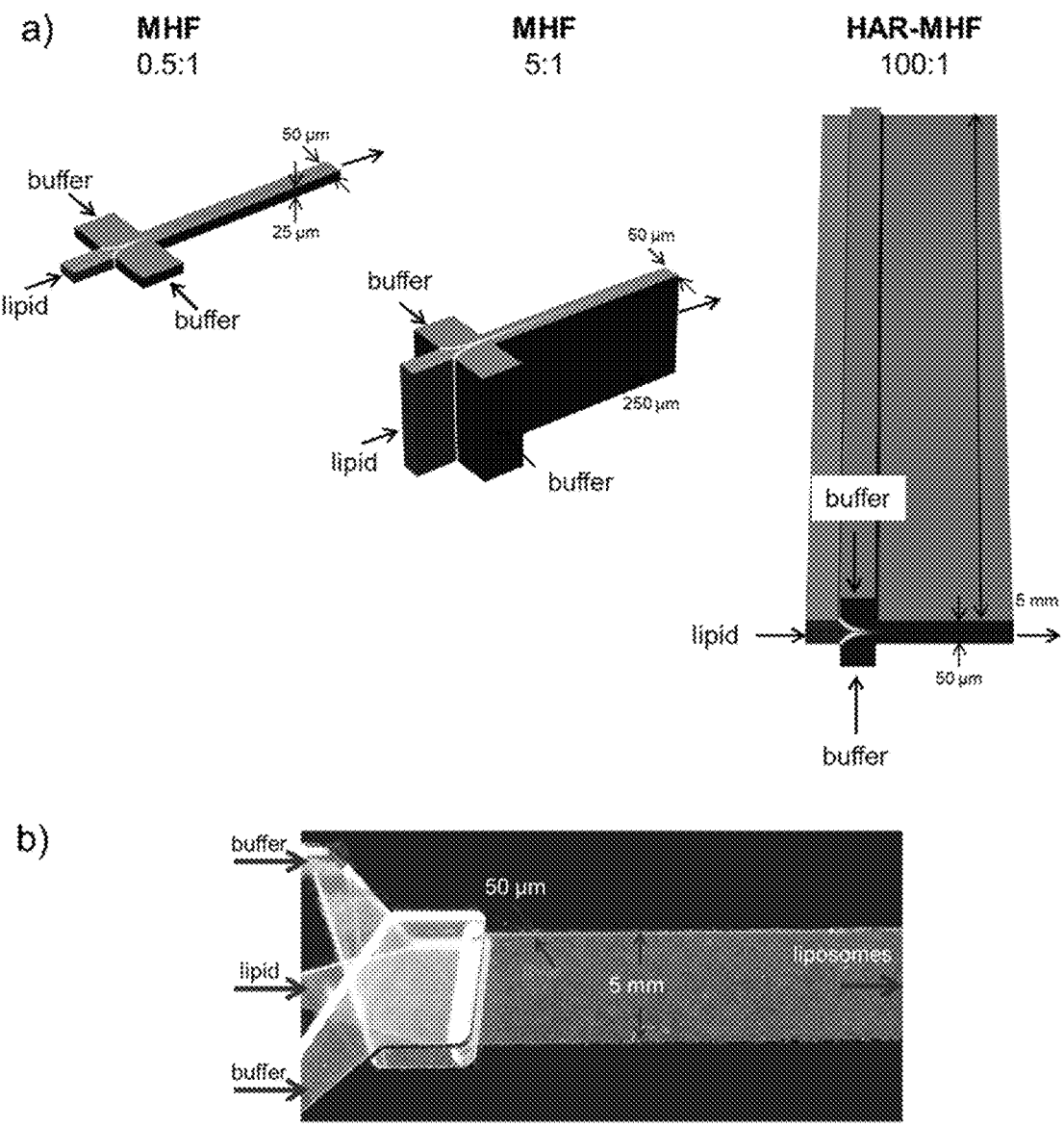
FIG. 13 illustrates schematically a comparison of two MHF devices and an HAR-MHF device (FIG. 13, panel a). Numerical simulations (COMSOL) were conducted comparing ethanol concentration profiles within MHF and HAR-MHF systems with increasing microchannel aspect ratios, and consequently increasing ethanol concentration profile uniformities. In HAR-MHF, the focusing axis is perpendicular to that of typical MHF, providing the benefits of an extremely high aspect ratio system with decreased back pressure and simple fabrication processes for robust high-throughput synthesis of liposomes.

Microfluidic devices were created using a combination of cyclic olefin copolymer (COC) plaques and thin COC films to produce high aspect ratio microchannels using simple fabrication techniques without the need for photolithographic methods or clean room processing. Buffer routing channels were fabricated in 1 mm thick COC plaques (6013 grade; Topas Advanced Polymers, Inc., Florence, Ky.) through a precision computer numerical control (CNC) milling machine (MDX-650A; Roland, Lake Forest, Calif.). Thin (50 μm) COC films (6013 grade; Topas Advanced Polymers, Inc.) were used to define a highly uniform channel height throughout the entire width of the mixing channel. The COC films were patterned using an automated craft cutter (Cameo Digital Craft Cutting Tool, Silhouette America, Inc., Orem, Utah) to be 5 mm in width, resulting in microfluidic devices with an effective 100:1 aspect ratio in the focusing channel. The resulting intersection between the buffer and lipid phases featured channels which were 100 μm and 50 μm in width (FIG. 13).

Traditional MHF devices were also fabricated using soft lithographic techniques for comparison to the HAR-MHF device, with the flow focusing intersection between the buffer and lipid-ethanol channels designed to be identical to the HAR-MHF device. Briefly, SU-8 negative photoresist (MicroChem Corp., Newton, Mass.) was spin-coated onto a 4-inch silicon wafer (University Wafer, South Boston, Mass.), exposed to ultraviolet light through a photomask on an automated EVG 620 mask aligner (EV Group, Germany), and developed to create master molds with raised features which were used to define microchannel features. The SU-8 mold was placed in a plastic petri dish and poly(dimethylsiloxane) (PDMS) elastomer (Sylgard 184, Dow Corning Corp. Midland, Mich.) was poured over the mold. Upon curing, the PDMS was carefully removed from the SU-8 mold and inlet and outlet holes were made using a biopsy punch (Harris Uni-Core, Ted Pella, Inc., Redding, Calif.). The bonding surfaces of the PDMS and a glass slide were cleaned using isopropanol and DI water, then exposed to oxygen plasma in a March Jupiter III Reactive Ion Etcher (Nordson Corp., Concord, Calif.). Final microfluidic device channel dimensions were 50 μm wide and either 25 μm or 250 μm high in the mixing region, resulting in devices with 0.5:1 and 5:1 aspect ratios (FIG. 13).

Lipid Film and Buffer Preparation

Dimyristoylphosphatidylcholine (DMPC), cholesterol (Avanti Polar Lipids Inc., Alabaster, Ala.) and dihexadecyl phosphate (DCP) (Sigma Aldrich, St. Louis, Mo.) were combined in chloroform (Mallinckrodt Baker Inc., Phillipsburg, N.J.) at a molar ratio of 5:4:1. The lipid mixture was prepared in a glass scintillation vial then stored in a vacuum desiccator for at least 24 h for complete solvent removal. The desiccated lipid mixture was re-dissolved in anhydrous ethanol (Sigma Aldrich) for a total lipid concentration of 20 mmol $L^{-1}$ unless otherwise noted. To assist in visualization during flow focusing experiments, a lipophilic membrane dye, 1,1'-dioctadecyl-3,3,3',3'-tetramethylindocarbocyanine perchlorate (DiI-C18; DiI) (Life Technologies, Carlsbad, Calif.) was included into the lipid mixtures (1 wt %).

Numerical Simulation of Ethanol Concentration Profiles & Fluid Velocity

A computational fluid dynamics simulation was produced to illustrate the variations in physicochemical properties between the distinctive microchannel aspect ratios. The ethanol-water concentration and fluid velocity profiles of a center stream of ethanol focused by an exterior sheath of water was represented in a three-dimensional model created using COMSOL Multiphysics 4.2 software (COMSOL Inc., Burlington, Mass.). For objective comparison, the flow rate ratio (FRR) in each simulation was set to 20:1 and the total flow velocity was set to 0.1 m/s (corresponding to volumetric flow rates of 1.5 mL/min, 75 µL/min, and 7.5 µL/min for aspect ratios of 100:1, 5:1, and 0.5:1, respectively).

Microfluidic Liposome Synthesis

Liposomes were synthesized through MHF for comparison. A center stream of lipid solvated in ethanol was injected between two streams containing aqueous hydration buffer (FIG. 13, panel a). The FRR, defined as the volumetric flow rate of the aqueous buffer to that of the solvent, was set to 10, 15, 20, 30, 40, 50, and 100 for each set of HAR-MHF and MHF experiments, with linear flow velocity held constant at 0.1 m/s in each device.

In the HAR-MHF device, the FRR was set to 20 with linear flow velocity at 0.1 m/s (corresponding to volumetric flow rates of 1.5 mL/min, 75 µL/min, and 7.5 µL/min for aspect ratios of 100:1, 5:1, and 0.5:1, respectively). Liposome populations were characterized through dynamic light scattering (Nano Z S, Malvern Instruments Ltd., UK).

Results & Discussion: HAR-MHF vs. MHF

Microfluidic processes benefit from high aspect ratio microchannels due to the diminishing effect of sidewall interaction which presents a no-slip boundary condition and thus disturbs flow profile and chemical species homogeneity (Ismagilov, R. F. et al. (2000) "*Experimental and theoretical scaling laws for transverse diffusive broadening in two-phase laminar flows in microchannels,*" Appl. Phys. Lett., 2000, 76:2376-2378; Hertzog, D. E. et al. (2004) "*Femtomole mixer for microsecond kinetic studies of protein folding*" Anal. Chem. 76:7169-78). However, microscale features become increasingly difficult to achieve as aspect ratio increases (Ito, H. (2005) "*Chemical amplification resists for microlithography,*" Adv Polym Sci 172:37-245), requiring sophisticated equipment and still failing to exceed values of about 20:1 (Becker, H. & Heim, U. (2000) "*Hot embossing as a method for the fabrication of polymer high aspect ratio structures,*" Sensors Actuators A Phys. 83:130-135; Hung, P. J. et al. (2005) "*A novel high aspect ratio microfluidic design to provide a stable and uniform microenvironment for cell growth in a high throughput mammalian cell culture array,*" Lab Chip, 5:44-8).

HAR-MHF offers a method which achieves unprecedentedly high aspect ratios as well as providing the advantages of simplified fabrication methods used for low aspect ratio features by rotating or reorienting the axis of diffusion perpendicular to the focusing axis as compared to configurations in traditional MHF. Here we demonstrate a HAR-MHF device for liposome synthesis within microchannels which have an aspect ratio of 20:1 or greater, more preferably 50:1 or greater, more preferably 100:1 or more. Devices having such aspect ratios which would be virtually impossible to produce through traditional microchannel fabrication techniques. Indeed, devices including microchannels with aspect ratios exceeding 200:1 may be provided in accordance with the disclosed fabrication techniques, thus providing an alternative method for MHF in microchannels with remarkably high aspect ratios.

Populations of liposomes were generated within both HAR-MHF and traditional MHF devices with varying channel aspect ratios in order to demonstrate how the high aspect ratio affects the resulting liposome populations. The microchannel dimensions at the intersection of the lipid and buffer channels and the mixing channel width were identical for all 3 devices tested, with the variation being that flow focusing occurred in the vertical plane within HAR-MHF microchannels which featured an aspect ratio of 100:1, while the focusing axis was in the horizontal plane in the two traditional MHF devices which featured microchannel aspect ratios of 0.5:1 and 5:1.

Figure 14:
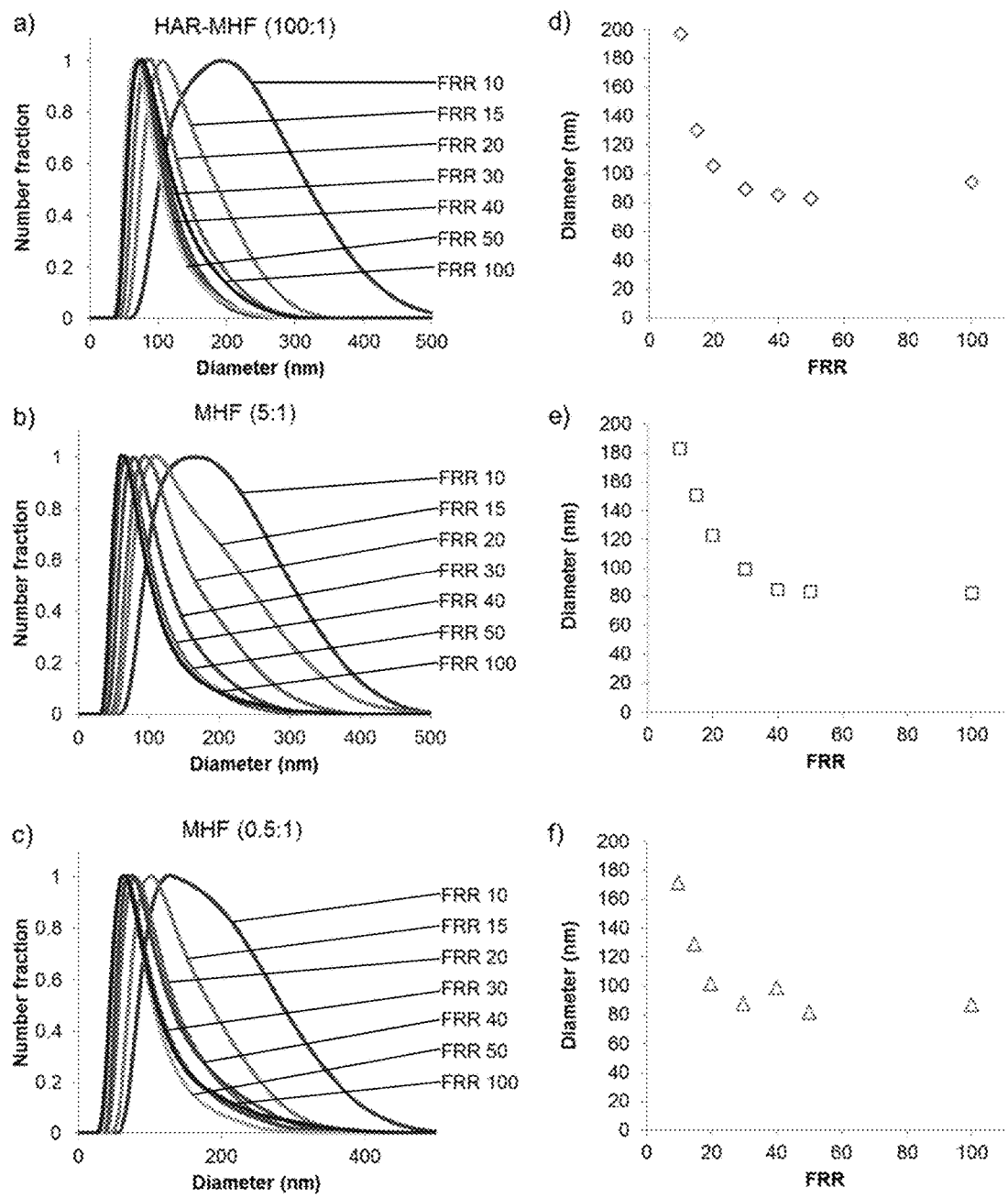
FIG. 14 illustrate graphically size distributions (FIG. 14, panel a, panel b, and panel c) and modal diameters (FIG. 14, panel d, panel e, and panel f) of liposomes produced within an exemplary HAR-MHF device in accordance with the present invention, with microchannel aspect ratio 100:1 (FIG. 14, panel a, and panel d) as compared to liposomes produced through traditional MHF using devices with microchannel aspect ratios of 5:1 (FIG. 14, panel b, and panel e) and 0.5:1 (FIG. 14, panel c, and panel f) at various FRRs. HAR-MHF upholds the established advantage of microfluidics to produce narrowly distributed populations of liposomes with tunable diameters.

Similar to traditional MHF, HAR-MHF produced narrowly distributed populations of liposomes in addition to providing the ability to control liposome size with FRR (FIG. 14). The capacity to inflict major change in liposome size with varying FRR decreased at FRRs above 30 for all devices, which is in accordance with previous studies of MHF for liposome production (e.g., Jahn, A. et al. (2007) "*Microfluidic Directed Self-Assembly of Liposomes of Controlled Size,*" Langmuir 23:6289-6293; Jahn, A. et al. (2008) "*Preparation of nanoparticles by continuous-flow microfluidics,*" J. Nanoparticle Res. 10:925-934; Jahn, A. et al. (2010) "*Microfluidic mixing and the formation of nanoscale lipid vesicles,*" ACS nano 4:2077-2087). The various microfluidic systems produced repeatable results, with modal diameters of the populations of liposomes produced under a particular FRR remaining consistent (<17% variation) between the HAR-MHF and MHF devices. This comparison study therefore exhibits the ability of HAR-MHF to generate nearly monodisperse liposomes of tunable size as previously demonstrated with traditional MHF.

Figure 15:
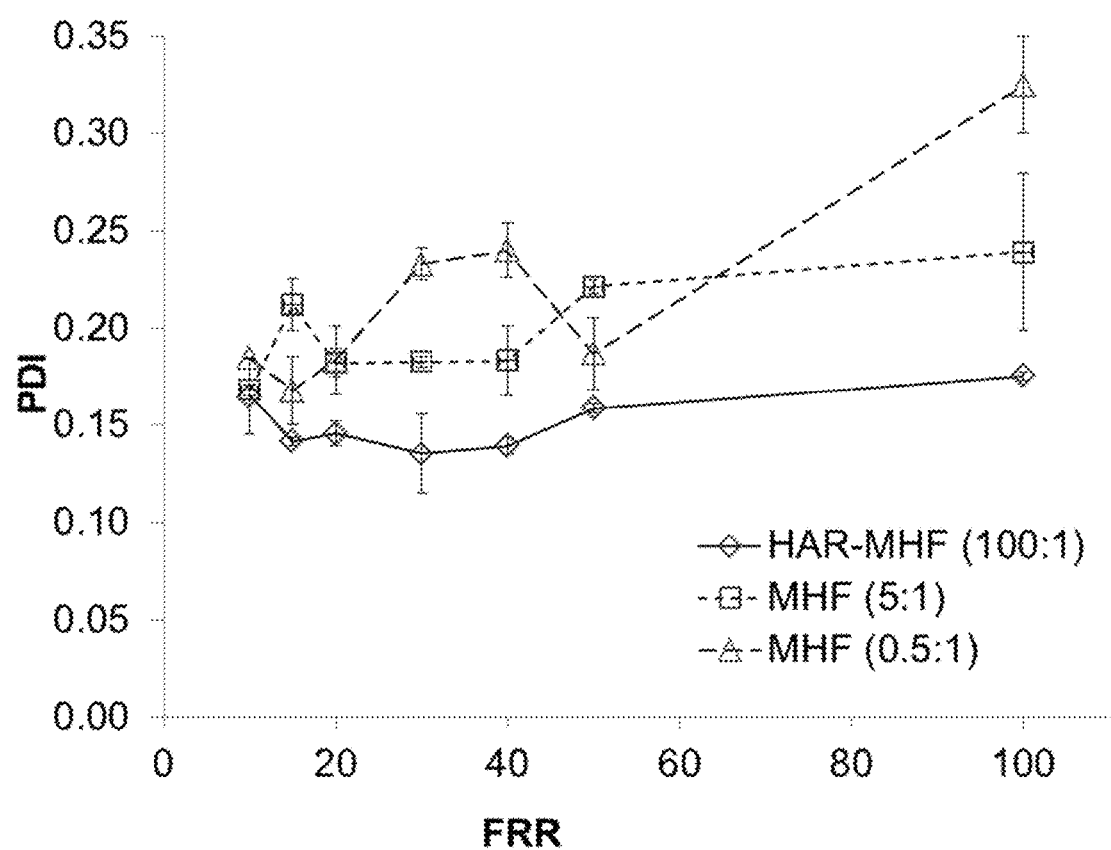
FIG. 15 illustrates graphically the polydispersity index (PDI) of each liposome sample produced within the HAR-MHF device with aspect ratio 100:1 compared to liposomes produced through traditional MHF devices with aspect ratios of 5:1 and 0.5:1 at various FRRs. Under each flow condition tested, HAR-MHF produced liposomes with a lower PDI than either of the MHF devices.

In addition to modal diameter, the quality of the liposomes produced through the various microfluidic flow focusing methods was assessed through the comparison of the polydispersity indices (PDIs) of each population (FIG. 15). Under each FRR tested, the PDI of the population of liposomes produced through HAR-MHF was lower than the corresponding population produced through traditional MHF, other than FRR 10 in which HAR-MHF produced a similar value to MHF (5:1). However, lower FRR have previously shown higher levels of polydispersity and lower levels of size control, so it is not surprising that the PDI was relatively unchanged despite the varying microchannel aspect ratios.

The lower PDI seen in HAR-MHF-generated vesicles demonstrates that a higher aspect ratio, and thus more uniform fluid velocity across the width of the mixing region, enables the production of more narrowly distributed populations of liposomes. Moreover, due to the microchannel dimensions, HAR-MHF (aspect ratio 100:1) supported the production of liposomes at rates 200 times and 20 times faster than the MHF devices with aspect ratios of 0.5:1 and 5:1, respectively. Therefore, HAR-MHF presents a method which enables the generation of microfluidic-enabled liposomes of tunable size with unprecedentedly low levels of polydispersity and exceedingly high rates of production as compared to traditional MHF methods.

Figure 16:
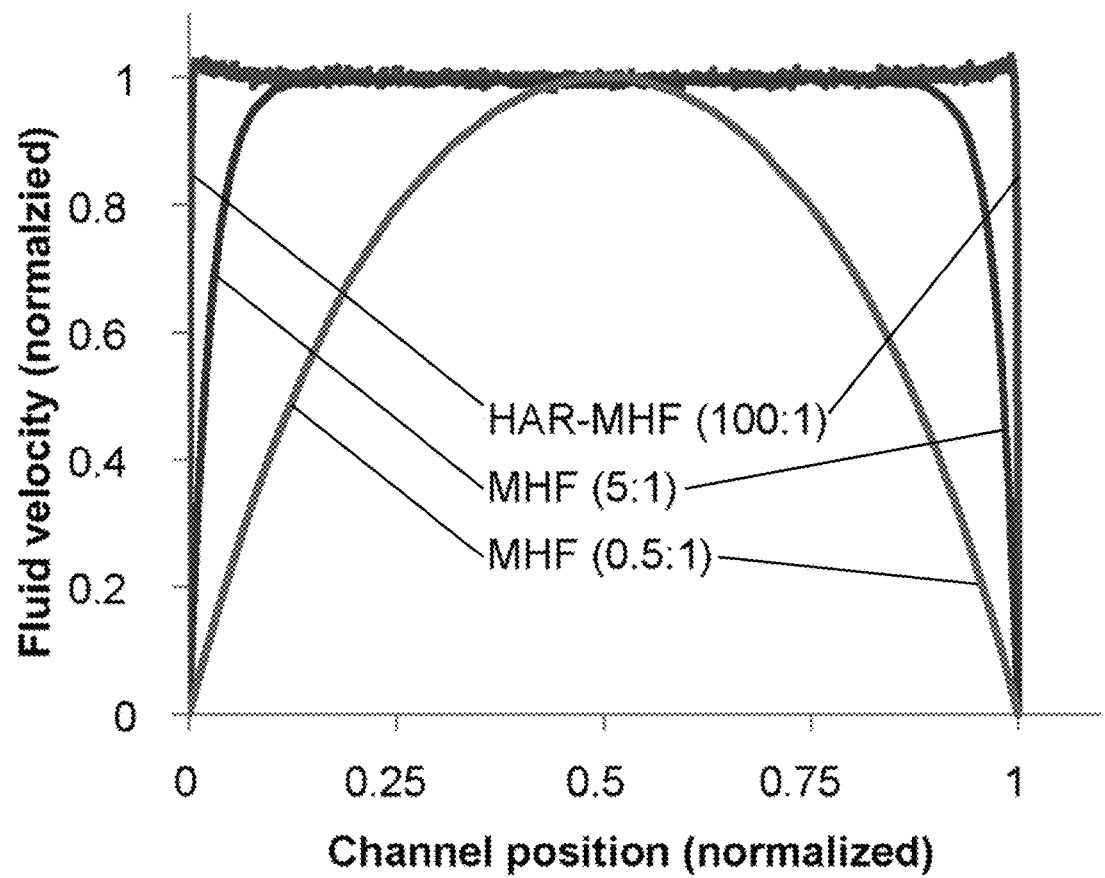
FIG. 16 are COMSOL simulations illustrating the fluid velocity at the midpoint of the channel width within the HAR-MHF and traditional MHF microfluidic devices at FRR 20. As the aspect ratio increases, flow velocity becomes more uniform across the width of the channel (all profiles normalized to effective channel height and maximum flow velocity).

Three-dimensional numerical simulations further demonstrate the varying flow conditions within each microfluidic device (FIG. 16). Simulations of fluid velocity at the midpoint of each channel width was normalized to distance along the channel height for comparison. As microchannel aspect ratio increases, the effect of the no-slip boundary condition (zero velocity at the channel walls) diminishes, and thus the flow velocity becomes more homogenous throughout the mixing region and results in more uniform concentration profiles of the ethanol-lipid throughout the mixing channel. This feature may explain the observed decrease in PDI for HAR-MHF versus both MHF microchannel geometries which generate more parabolic velocity profiles.

HAR-MHF: Initial Lipid Concentration

Figure 17:
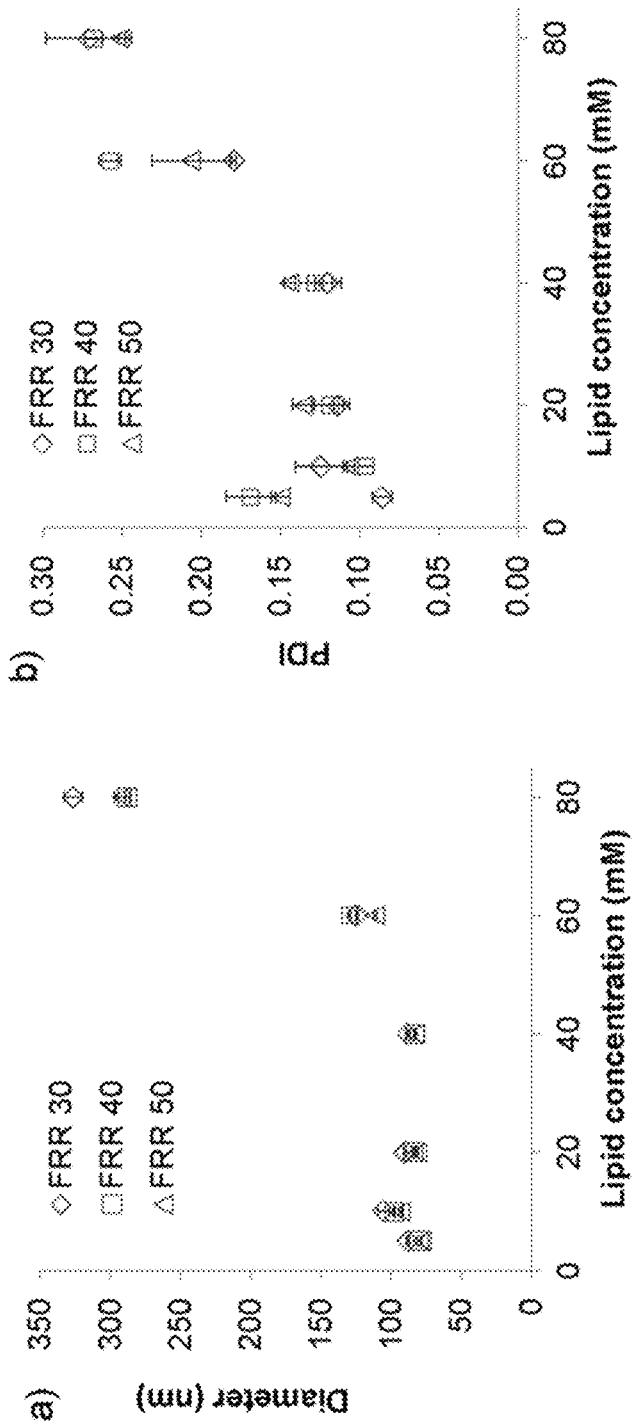
FIG. 17 illustrates graphically modal diameters (FIG. 17, panel a) and PDI (FIG. 17, panel b) of liposomes produced through the HAR-MHF device with the initial lipid concentration varying from 5 mM to 80 mM. An increase in initial lipid concentration, increase in final liposome concentration and production rate, does not largely affect liposome modal diameter or PDI when increasing from 5 mM up to 40 mM. Higher concentrations (60 mM and 80 mM) cause an increase in both liposome size and polydispersity.

One way to control final liposome concentration, which is important for reaching relevant dose levels for in vivo and preclinical studies, within MHF methods for liposome production is to control the initial lipid concentration. The effect of the initial lipid concentration on the resulting populations of liposomes produced through HAR-MHF was examined by varying the lipid concentration incrementally from 5 mmol $L^{-1}$ to 80 mmol $L^{-1}$ (FIG. 17). As demonstrated, increasing the initial lipid concentration (and thus final volumetric fraction of liposomes) did not result in any substantial changes to the resulting liposome populations as the concentration varied from 5 mmol $L^{-1}$ to 40 mmol $L^{-1}$ in terms of both modal diameter (FIG. 17, panel a) or PDI (FIG. 17, panel b). Rather, increasing the initial lipid concentration to 60 mmol $L^{-1}$ and 80 mmol $L^{-1}$ caused liposome modal diameter to increase in addition to resulting in higher PDIs. Therefore, the final liposome concentration may be increased by increasing the initial lipid concentration up to 40 mmol $L^{-1}$, or 8 times higher than initial traditional MHF studies, without impinging on the quality of vesicles produced.

HAR-MHF: Fluid Velocity

Liposome production rates within MHF techniques may be tweaked somewhat by altering overall flow velocities. However, devices used for traditional MHF contain microscale channel dimensions which do not support high volumetric flow rates due to back pressure. In contrast, HAR-MHF devices contain one dimension which is an order of magnitude higher than traditional MHF, and therefore back pressure is significantly reduced and unprecedentedly high flow rates are achieved.

Figure 18:
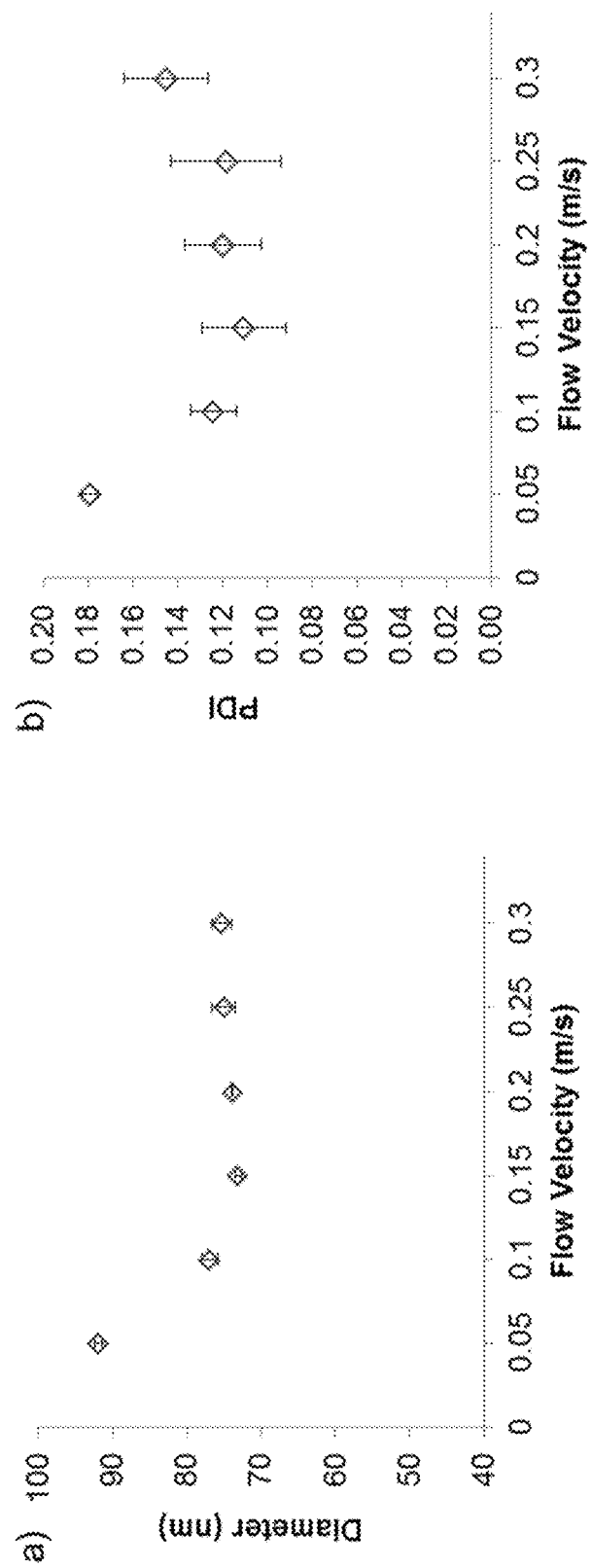
FIG. 18 illustrates graphically modal diameter (FIG. 18, panel a) and PDI (FIG. 18, panel b) of populations of liposomes generated via HAR-MHF at FRR 20 and total linear flow velocities ranging from 0.05 m/s to 0.3 m/s (0.75 mL/min to 4.5 mL/min, respectively). For flow velocities higher than 0.1 m/s, liposome diameter and PDI are both nearly constant, demonstrating that higher throughput for the HAR-MHF system may be achieved by increasing total flow velocity without causing significant changes in the resulting liposome populations.

The effect of overall flow velocity on liposome production in HAR-MHF was assessed (FIG. 18). A decrease in flow velocity from 0.1 m/s to 0.05 m/s resulted in an increase in modal diameter (~19% larger) as well as an increase in polydispersity (~30% increase in PDI). However, an increase in flow velocity from 0.1 m/s to 0.3 m/s (1.5 mL/min to 4.5 mL/min) did not significantly affect liposome quality, with the modal diameter fluctuations within 5% over these velocities. In addition, the PDI fluctuated slightly across the various flow conditions, but no trend was observed between flow velocity and polydispersity. Thus, as demonstrated, liposome production through HAR-MHF is not affected by flow velocity and therefore the primary limitation regarding throughput from a single HAR-MHF element is back pressure from the device and tubing inlets.

Comparison of Methods: Liposome Production Rate

Figure 19:
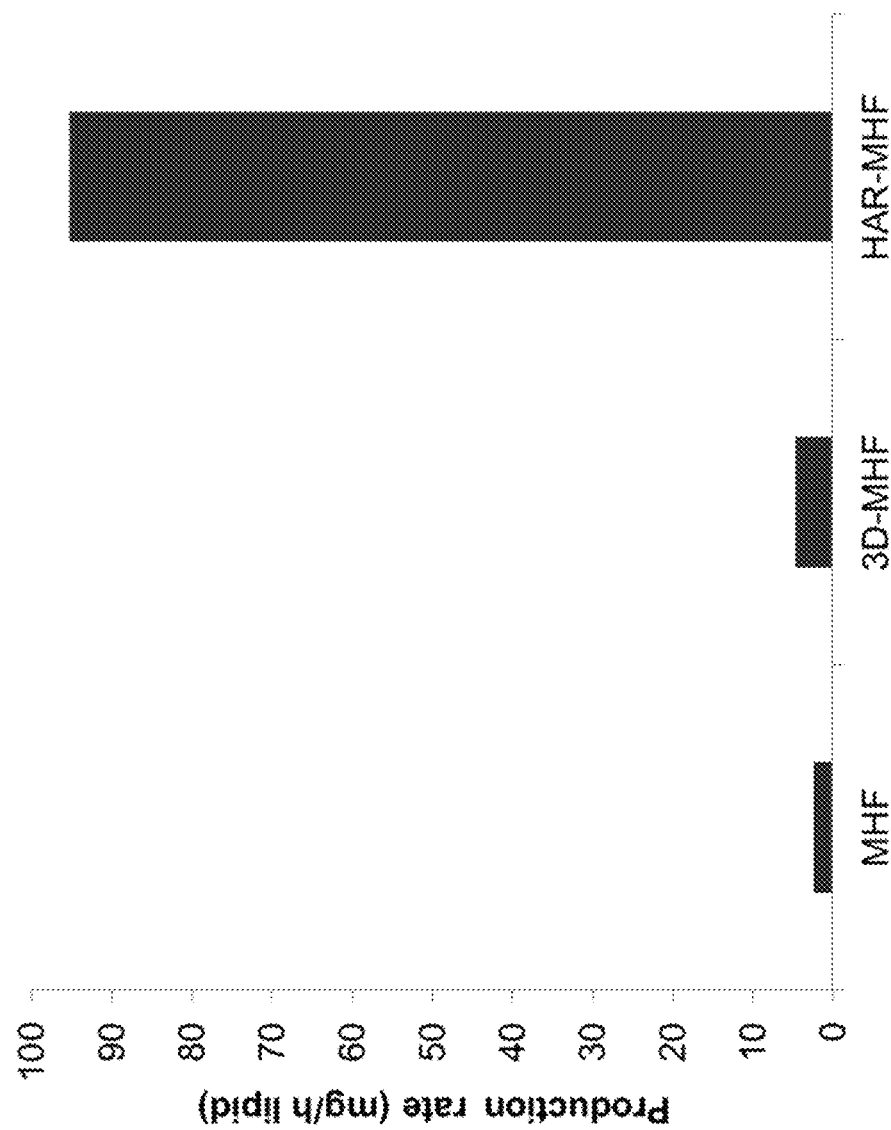
FIG. 19 illustrates graphically a comparison of liposome production rates across tested microfluidic methods, using a consistent 20 mM starting lipid concentration. HAR-MHF enables the generation of liposomes at ~100 mg/h lipid, two orders of magnitude higher than traditional MHF, without sacrificing any of the benefits provided by microfluidic liposome synthesis. Similarly, HAR-MHF produces liposomes one order of magnitude faster than a capillary-based 3D-MHF method, while providing approximately $10^2$~$10^3$ times higher vesicle concentration than the capillary system.

An advantage of HAR-MHF is its ability to generate nearly monodisperse populations of liposomes at extraordinary rates as compared to prior microfluidic systems. To demonstrate this advantage, typical values for liposome production rates utilizing HAR-MHF were compared to the various demonstrated methods of traditional MHF-directed liposome synthesis, including traditional MHF and 3D-MHF (Hood, R. R. et al. (2014) "*A facile route to the synthesis of monodisperse nanoscale liposomes using 3D microfluidic hydrodynamic focusing in a concentric capillary array,*" Lab Chip 14:2403-2409), maintaining a constant initial lipid concentration of 20 mmol $L^{-1}$ (FIG. 19). HAR-MHF enables the generation of liposomes at ~100 mg/h lipid, two orders of magnitude higher than traditional MHF, without sacrificing any of the benefits provided by microfluidic liposome synthesis (e.g., controlled size and low polydispersity). Similarly, HAR-MHF also produces liposomes nearly two orders of magnitude faster than the demonstrated capillary-based 3D-MHF method, while also providing approximately $10^2 \sim 10^3$ times higher vesicle concentration than the capillary system due to necessary flow conditions to achieve particular sizes. The data confirmed that HAR-MHF was about two orders of magnitude faster in microfluidic liposome generation as compared to prior microfluidic techniques. Further, HAR-MHF systems in accordance with disclosed embodiments are capable of producing nanoparticles faster than other prior devices utilizing parallelization for high-throughput nanoparticle production due to the increased channel dimensions.

Thus, the disclosed systems and data demonstrate HAR-MHF devices are extremely effective for high throughput continuous flow synthesis of self-assembled nanoscale liposomes. HAR-MHF methods enable the production of nearly monodisperse liposomes with tunable diameters, and at unprecedented speeds with further reduced levels of polydispersity as compared to prior microfluidic systems. HAR-MHF techniques in accordance with the present invention embody significant implications for drug delivery applications as it renders microfluidic-synthesized liposomes more practical for in vivo studies, preclinical trials and point-of-care applications as compared to other previously demonstrated techniques.

All publications mentioned in this specification are herein incorporated by reference to the same extent as if each individual publication was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A microfluidic device for synthesis of liposomes, comprising:
   a sample flow channel;
   a first inlet channel in fluid communication with said sample flow channel;
   second and third inlet channels in fluid communication with said sample flow channel, said first, second and third inlet channels converging at a flow focusing region within said sample flow channel, wherein said sample flow channel has an aspect ratio (height:width) exceeding 20:1 at said flow focusing region;
   a counterflow channel adjacent to said sample flow channel and downstream from said flow focusing region; and
   a membrane in between said sample flow channel and said counterflow channel, said membrane configured to permit buffer exchange between said sample flow channel and said counterflow channel.

2. The microfluidic device of claim 1, wherein said aspect ratio is 50:1 or greater.

3. The microfluidic device of claim 1, wherein said aspect ratio is 100:1 or greater.

4. The microfluidic device of claim 1, wherein said first, second and third inlet channels are vertically oriented relative to each other.

5. The microfluidic device of claim 1, wherein said membrane is configured to prevent selected particles from passing between said sample flow channel and said counterflow channel.

6. The microfluidic device of claim 1, further comprising a fourth inlet channel in fluid communication with said sample flow channel, said fourth inlet channel configured to direct a first agent into said sample flow channel.

7. The microfluidic device of claim 6, wherein said fourth inlet channel converges with said sample flow channel at said flow focusing region.

8. The microfluidic device of claim 6, wherein said fourth inlet channel converges with said sample flow channel downstream of said flow focusing region.

9. The microfluidic device of claim 7, further comprising a fifth inlet channel in fluid communication with said sample flow channel, said fifth inlet channel configured to direct a second agent into said sample flow channel.

10. The microfluidic device of claim 9, wherein said fifth inlet channel converges with said sample flow channel downstream of said flow focusing region.

11. The microfluidic device of claim 1, further comprising a lipid solution flowing through said first inlet channel and into said sample flow channel, and a buffer solution flowing through said second and third inlet channels and into said sample flow channel, wherein said lipid solution and said buffer solution interact at said flow focusing region and form a population of liposomes.

12. The microfluidic device of claim 11, wherein said population of liposomes have a median diameter of between about 20 nm and about 500 nm.

13. The microfluidic device of claim 12, wherein said population of liposomes have a median diameter of between about 20 nm and about 100 nm.

14. The microfluidic device of claim 11, wherein said population of liposomes have a percent polydispersity of less than about 10%.

15. The microfluidic device of claim 14, wherein said population of liposomes have a percent polydispersity of less than about 5%.

16. A microfluidic device for synthesis of liposomes, comprising:
   a sample flow channel;
   a first inlet channel in fluid communication with said sample flow channel;
   second and third inlet channels in fluid communication with said sample flow channel, said first, second and third inlet channels converging at a flow focusing region within said sample flow channel, wherein said sample flow channel has an aspect ratio (height:width) exceeding 20:1 at said flow focusing region;
   a lipid solution flowing through said first inlet channel and into said sample flow channel, and a buffer solution flowing through said second and third inlet channels and into said sample flow channel, wherein said lipid solution and said buffer solution interact at said flow focusing region and form a population of liposomes;
   a counterflow channel adjacent to said sample flow channel and downstream from said flow focusing region; and
   a membrane in between said sample flow channel and said counterflow channel, said membrane permitting buffer exchange between said sample flow channel and said counterflow channel and establishing a transmembrane ion gradient in said population of liposomes.

17. The microfluidic device of claim 16, further comprising a fourth inlet channel throughout which a first agent flows and in fluid communication with said sample flow channel, said fourth inlet channel downstream of said counterflow channel, wherein said first agent is actively loaded within intravesicular spaces of said liposomes to form agent-loaded liposomes.

18. The microfluidic device of claim 17, wherein said first agent is a therapeutic or diagnostic agent.

19. The microfluidic device of claim 18, wherein said agent-loaded liposomes exhibit a drug-to-lipid molar ratio of greater than 0.5.

20. The microfluidic device of claim 19, wherein said agent-loaded liposomes exhibit a drug-to-lipid molar ratio of greater than 2.0.

* * * * *